(12) United States Patent
Hay et al.

(10) Patent No.: US 6,419,638 B1
(45) Date of Patent: Jul. 16, 2002

(54) OPTICAL RECOGNITION METHODS FOR LOCATING EYES

(76) Inventors: Sam H. Hay, 310 Clinton Ave. W., Huntsville, AL (US) 35801; David L. Guice, 230 Haden Rd., Brownsboro, AL (US) 35741

( * ) Notice: Subject to any disclaimer, the term of this patent is extended or adjusted under 35 U.S.C. 154(b) by 0 days.

(21) Appl. No.: 09/630,178

(22) Filed: Aug. 1, 2000

Related U.S. Application Data

(63) Continuation-in-part of application No. 09/150,000, filed on Sep. 8, 1998, now Pat. No. 6,095,989, which is a continuation-in-part of application No. 08/932,036, filed on Sep. 17, 1997, now abandoned, which is a continuation-in-part of application No. 08/863,801, filed on May 27, 1997, now abandoned, which is a continuation-in-part of application No. 08/324,884, filed on Oct. 18, 1994, now Pat. No. 5,632,282, which is a continuation-in-part of application No. 08/093,685, filed on Jul. 20, 1993, now Pat. No. 5,355,895.

(51) Int. Cl.$^7$ ................................................. A61B 5/00
(52) U.S. Cl. ..................................................... 600/558
(58) Field of Search ........................ 600/558; 351/200, 351/221

(56) References Cited

U.S. PATENT DOCUMENTS

| | | | | |
|---|---|---|---|---|
| 4,569,354 A | * | 2/1986 | Shapiro et al. | 128/665 |
| 5,139,030 A | * | 8/1992 | Seay | 128/745 |
| 5,303,709 A | * | 4/1994 | Dreher et al. | 128/665 |
| 5,355,895 A | * | 10/1994 | Hay | 128/745 |
| 5,632,282 A | * | 5/1997 | Hay et al. | 128/745 |

* cited by examiner

*Primary Examiner*—Max Hindenburg
(74) *Attorney, Agent, or Firm*—Mark Clodfelter

(57) ABSTRACT

A method for processing an image of eyes of a subject is provided. The image is divided into two halves, each containing an eye of the subject. The halves are then processed to determine at least a position of a pupil within the first half and second half. After positions of the pupils are determined, horizontal and vertical histograms are developed from the pupil in each of the halves. Several ways of plotting the respective histograms are disclosed, these plots provided with various indicators for detecting abnormal conditions of the eyes.

30 Claims, 63 Drawing Sheets

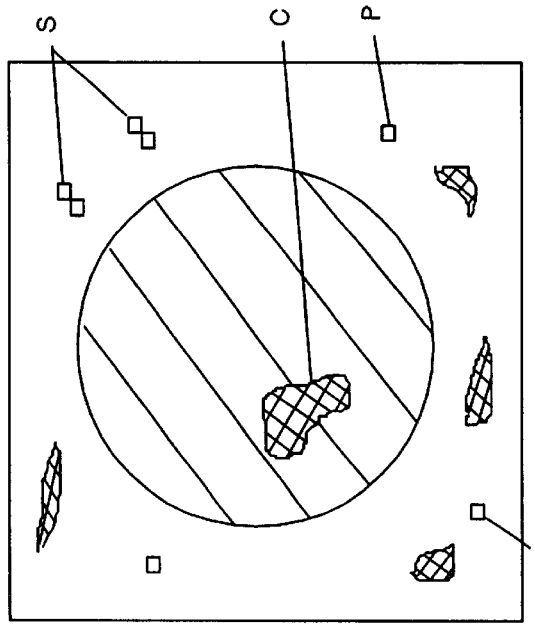
FIG. 5c
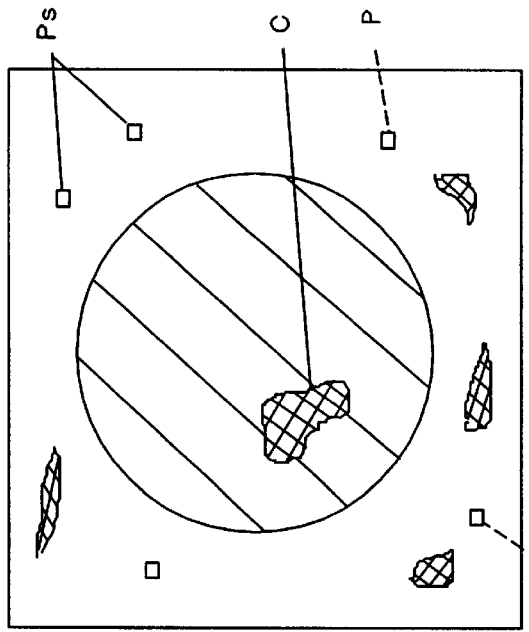
FIG. 5d
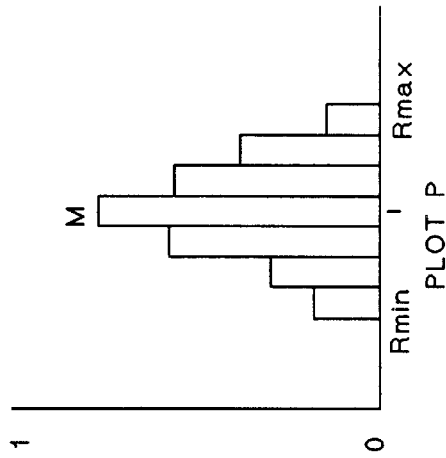
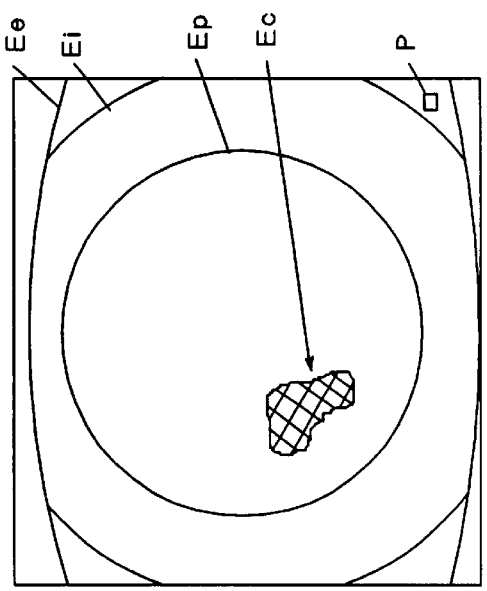
FIG. 5e

96 PIXELS
96 PIXELS
PUPIL

RADIUS
COUNT

LOW THRESHOLD

MEAN THRESHOLD

CROWN THRESHOLD

POSITION

OPTICAL RECOGNITION METHODS FOR LOCATING EYES

CROSS REFERENCES TO RELATED APPLICATIONS

This application is a continuation-in-part application of patent application Ser. No.: 09/150,000, filed Sep. 8, 1998 now U.S. Pat. No. 6,095,989, which is a continuation-in-part of patent application Ser. No. 08/932,036, filed Sep. 17, 1997 now abandoned, which is a continuation-in-part of patent application Ser. No. 08/863,801, filed May 27, 1997 now abandoned, which is a continuation-in-part of patent application Ser. No. 08/324,884, filled Oct. 18, 1994, now U.S. Pat. No. 5,632,282, which is a continuation-in-part of patent application Ser. No. 08/093,685, filed Jul. 20, 1993, now U.S. Pat. No. 5,355,895.

STATEMENT REGARDING FEDERALLY SPONSORED RESEARCH OR DEVELOPMENT

Not applicable.

FIELD OF THE INVENTION

This invention relates generally to methods of optical examination of eyes of a subject through the use of a reflex photometer, and particularly to methods implemented by a general purpose computer for locating eyes and pupils of a subject and determining a variety of parameters therefrom.

BACKGROUND OF THE INVENTION

The pupillary reflex, which occurs when light is reflected by the retina out through the pupil of an eye of a human or animal is a well known phenomenon, and has been the subject of considerable research. Through this research, it has been found that diagnosis of some abnormal conditions and disease processes of the eye may be made by observing the pupillary reflex. For instance, where a slightly off-axis light source with respect to an observation point directly in front of the eyes is directed into eyes of a subject, a reflex from an eye with normal refractive properties will not return the reflex to the observation point. Rather, a faint, general illumination of the pupil will be observed due to scattering of light within the eye. However, in an eye with abnormal refractive properties, a portion of the reflex will be observed at the observation point, with the extent of the reflex and position of the reflex about the circumference of the pupil being indicative of various abnormal conditions in the eye. Additionally, cataracts, occlusions, foreign objects and other opaque or semitransparent matter may be observed due to light being blocked by these objects or opacities. Additional information that may be ascertained includes binocular status of the eyes.

In U.S. Pat. No. 5,632,282, filed Oct. 18, 1994 by Dr. S. Hutson Hay et. al., and which is incorporated herein by reference in its entirety, a reflex photometer and method is disclosed for observing the retinal reflex from eyes of a subject. In this patent, a camera having a CCD array is mounted directly in front of eyes of a subject, and a slightly off-axis light source directs a strobed, collimated beam of light into eyes of the subject. An image of the eyes is received by the CCD array and processed by a general purpose computer to locate the eyes and identify a number of disease or other conditions that may be present.

While the algorithms of the referenced patent worked well, there were some situations wherein the eye could not be located. Accordingly, it is one object of this invention to provide methods of locating the eye which are inherently more robust, locating the eye in a higher percentage of trials. As an additional object of the invention, algorithms are disclosed herein that are also more accurate, being more computationally intensive due to recent developments that have increased computational power of microcomputers.

BRIEF DESCRIPTION OF THE SEVERAL VIEWS OF THE DRAWINGS

FIGS. 5c, 5d, 5e, 5f, 5g and Plot P illustrate particular steps of the processes of FIG. 5b.

FIG. 10e is a flowchart of a categorizing process for categorizing disease processes.

FIGS. 15*k*, 15*l*, 15*m* and 15*n* are flowcharts illustrating particulars of the flowchart of FIG. 15*j*.

DETAILED DESCRIPTION OF THE INVENTION

Figure 1:
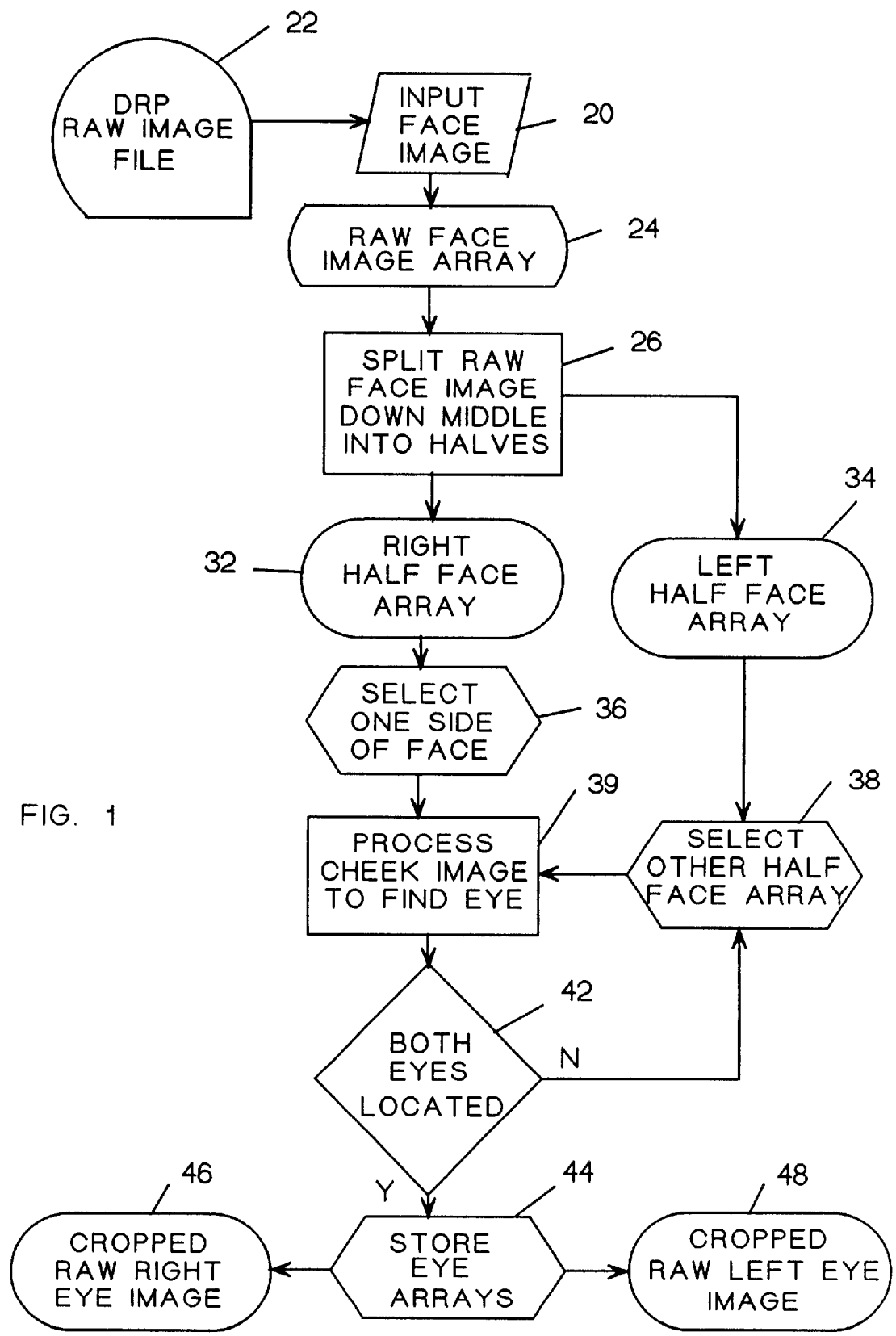
FIG. 1 is a high level flowchart of a first method for identifying eyes of a subject.

A general purpose computer is used in this invention to perform a variety of processing operations on an image of eyes of a subject, the eyes including a retinal reflex developed by apparatus such as disclosed in U.S. Pat. No. 5,632,282, which is incorporated herein by reference in its entirety. Programming languages suitable for this application include Fortran and versions of C, by Borland, although selection of a programming language applicable to the algorithms disclosed herein should be apparent to one skilled in the art.

One improvement to the apparatus disclosed in U.S. Pat. No. 5,632,282 is with respect to referencing brightness of light directed into eyes of a subject. As a feature of the invention disclosed in the referenced patent, bright and dark reference values are provided by a small reflective surface and a small dark surface, respectively, that are consistently registered by the same groups of pixels in the CCD array. As such, since the ratio of reflectance between the bright reference surface and dark reference surface is constant, information from these pixels may be used in a calibration capacity by scaling intermediate intensity values to these brightest and darkest intensity values, eliminating inaccuracies due to accumulation of dust on optical components of the apparatus and variances in intensity of the light source and sensitivity of the CCD focal plane array. Another type of light intensity referencing may be done by mounting a synthetic ruby sphere, as obtainable from EDMOND SCIENTIFIC COMPANY, the sphere being on the order of about 3–4 millimeters or so in diameter. This sphere may be mounted in an opening, blind or otherwise, in a stabilizer bar for the forehead of a subject just above a lower edge thereof so that the ruby sphere is generally vertically positioned between the eyes of the subject. The area around the ruby sphere may be of a contrasting character, such as being painted flat black or some other dark color. Here, the sphere serves a calibration means to determine whether the flash and camera are operating within normal parameters. The sphere may also serve as a reference means by establishing a point in the image that provides a point of essentially constant reflectance against which brighter light intensities may be scaled. The dark area around the sphere may also be used as a reference against which darker intensities of light may be scaled. Lastly, where the ruby sphere is simply bonded in place, it has been found that the reflex from the sphere generates a distinctively unique spectral signature that may be used for identification purposes or for determining if tampering or disassembly and reassembly of the device has occurred. Here, any shift of components of the device due to disassembly and reassembly will alter the spectral signature of the reflex from the ruby sphere. Also, where records of the spectral signatures of the ruby spheres are maintained, it is possible to readily ascertain as to whether a device of the instant invention is a copy produced by an infringing entity. While a ruby sphere is specifically disclosed, other similar articles of different construction and shape may be used, such as a half-sphere of transparent or semi-transparent material bonded or otherwise directly attached to the stabilizer bar.

The following algorithms disclose additional methods for locating pupils of a subject and for analyzing the pupil data registered by the CCD array in camera 72 of the referenced patent. These algorithms may be used in any combination with those disclosed in the referenced patent and parent case to this application. Additionally, any of the algorithms disclosed herein may be used together in any combination, as should be evident to one skilled in the art.

Initially, a bit map from the CCD camera representing the face of a subject including the eyes, hereinafter denoted as a full face array, or where the full face array is divided vertically in half so that each half contains one of the eyes of the subject, hereinafter denoted as a half face array, is parsed into a file which may be stored in conventional nonvolatile memory for retrieval and examination at a later time or placed directly into RAM memory of the computer. These full face and half face arrays may be copied by the various routines as many times as needed to accomplish the various operations as disclosed herein. A routine is then called to generally locate pupils of the eyes and provide a graphical representation for confirmation by the user that the eyes have been located. This and other routines disclosed herein, due to the linear nature of computer instructions and operation, is caused to operate first on one portion of the field of view containing one eye, and then the routine is caused to operate on the other portion of the field of view containing the other eye. Alternately, where parallel processing is undertaken, simultaneous operations may occur where feasible.

Figure 1A:
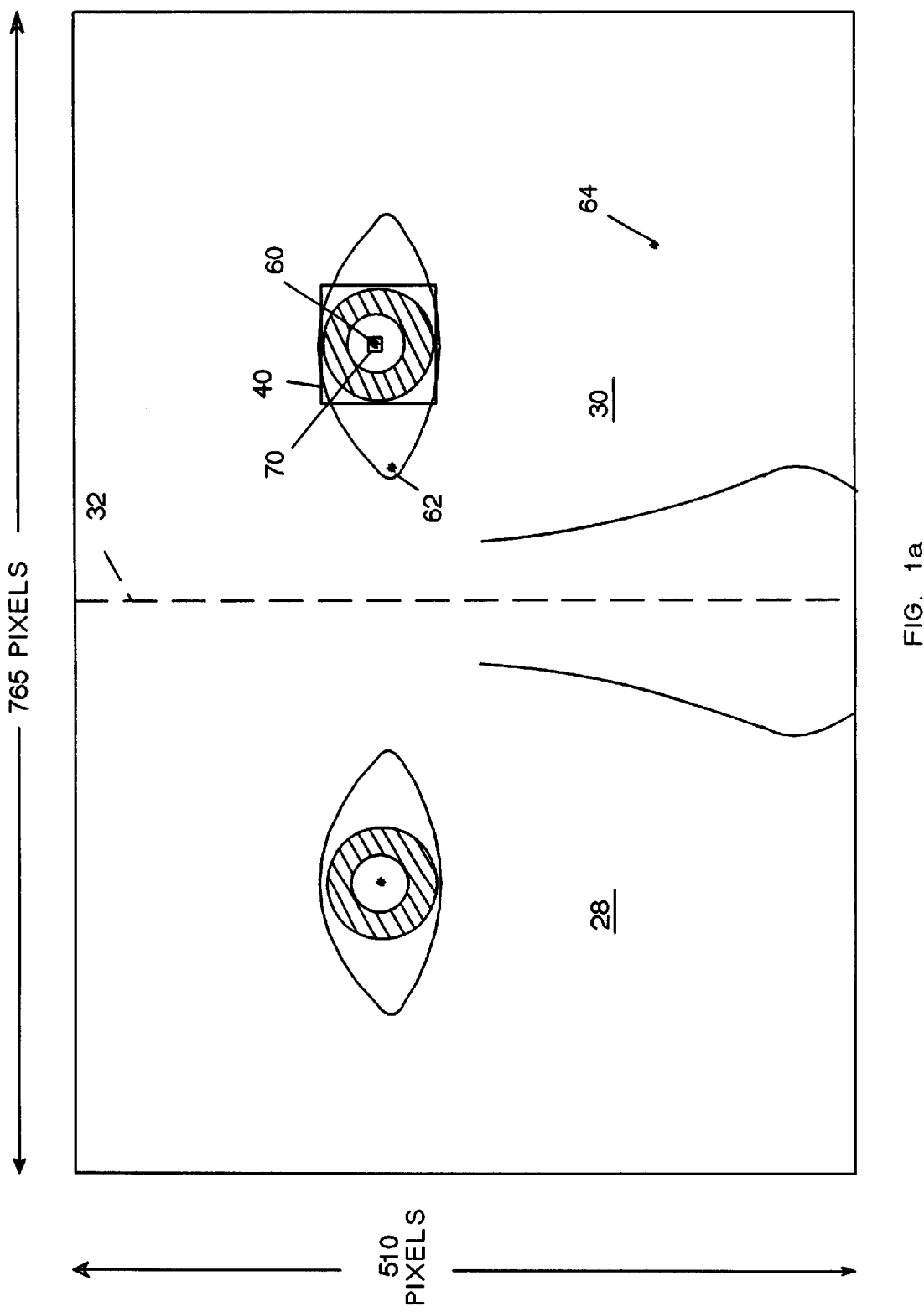
FIG. 1a is a diagram illustrating particular details relating to the flowchart of FIG. 1.

Referring initially to the flowchart of FIG. 1 and the accompanying FIG. 1*a*, a flowchart and drawing illustrating high level operation of one method is shown. At box 20 the raw data image of the eyes and adjacent area of the face imaged by the camera is retrieved from memory 22 and parsed into the computer memory at box 24. As described in the referenced patent, the pixel image, or array, from the CCD array of the camera is 510 pixels high and 765 pixels long, as shown in FIG. 1*a*, although other size and resolution arrays may be used, as should be apparent to those skilled in the art. Each pixel in the image is represented by a 16 bit integer, or 2 bytes, these output bytes arranged in a mapped format stored in memory accessible by the computer. At box 26 the pixel image of the face is divided vertically into two halves 28 and 30 (FIG. 1*a*), as indicated by dashed line 32, with one of these halves being about 382 pixels long and the other half being about 383 pixels long. By dividing the pixel image vertically into closely approximate halves, it is assured that half 28 will contain the right eye and half 30 will contain the left eye. Each of halves 28 and 30 is selected in turn and processed to locate the pupil, as indicated at boxes 32 and 34, with boxes 36 and 38 selecting one or the other sides of the face. Initially, processing to locate the eyes includes cropping those portions from the left and right images 28 and 30 that include the iris and an area just around the iris of the eyes, as shown by box 40 in FIG. 1a and by box 39 in FIG. 1. At box 42 the query is made as to whether both eyes have been located. If the answer is NO, as where one or the other or both of the eyes have not been located, then the program loops back in further attempts to locate the eye or eyes that were not found. In the rare instance where one or both eyes cannot be located, a flag is set to communicate this status to the operator, permitting the eyes of the subject to be reimaged if desired. In some instances, where only one eye is located, the program may be configured to set the flag indicating that only one eye can be located, and process data from the located eye. If both eyes have been located, as indicated by a YES answer at box 42, then both left and right pixel image arrays 28 and 30 are retained for processing at box 44 as indicated by boxes 46 and 48. As stated, after the eyes are located at box 39, cropped right and left eye images are retained at boxes 46 and 48, respectively, for further processing to determine whether abnormalities or disease conditions exist in the transparent media of the eyes. Alternately, the operator may use a pointing device, such as a mouse, to position crosshairs or other indica over imaged pupils of the subject, after which the computer would be instructed to process the retinal reflex.

Figure 2:
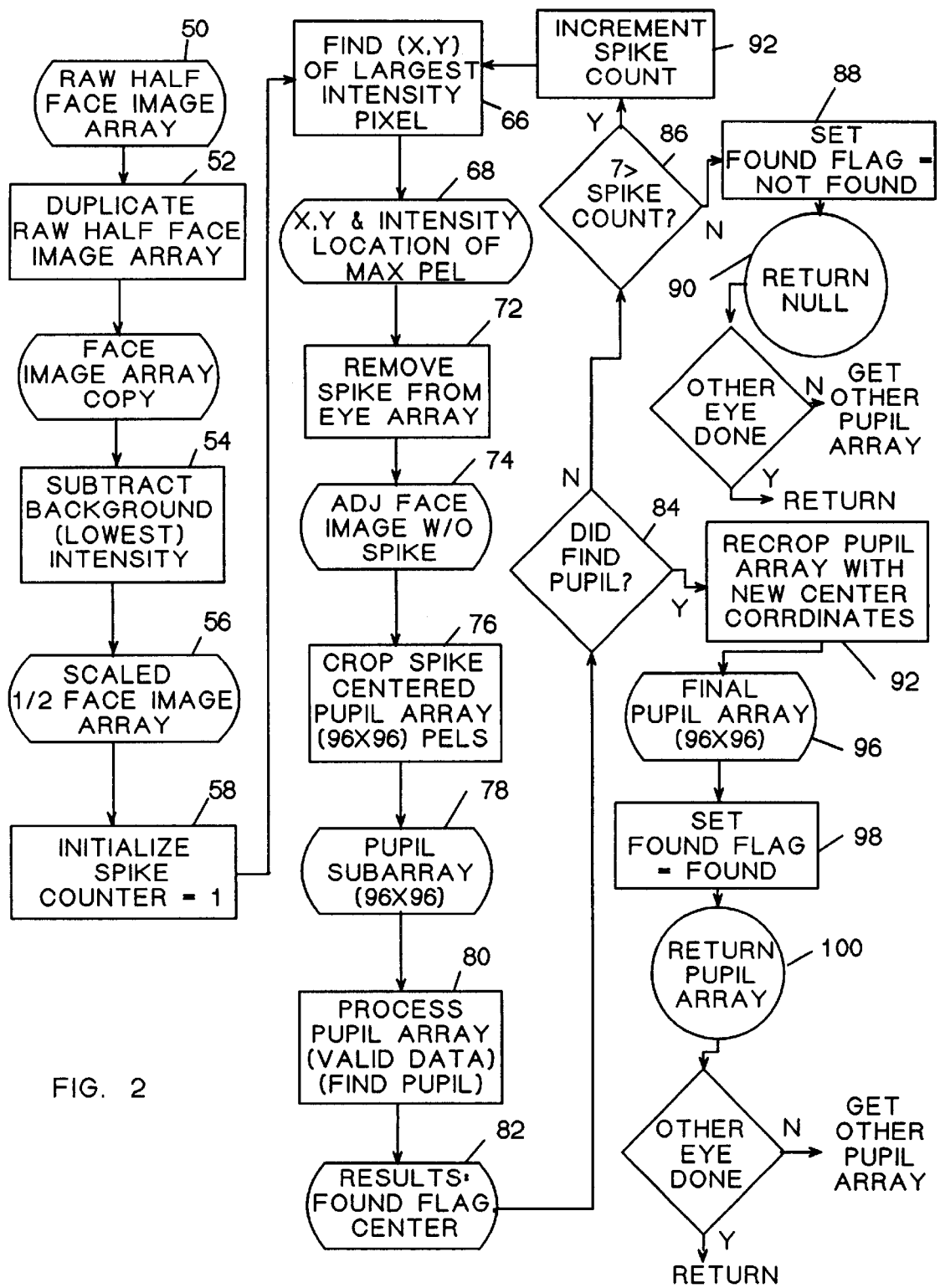
FIG. 2 is a flowchart of a method for processing half face pixel arrays.

Turning now to the flowchart of FIG. 2, processing of the left and right pixel arrays is shown. Here, processing of one of the pixel arrays 28 and 30 is illustrated, it being understood that such processing is applicable to both the left and right arrays. At box 50, one of the half face pixel images of the eye and face is accessed, and a copy of the selected half face image made at box 52. At box 54 a scaling background value is subtracted from all pixels in the array. This scaling background value is generally obtained from automated or set background values in the camera hardware. Alternately, it may be obtained by selecting the lowest light intensity value in the image and setting it equal to a value of 0. The resulting scaled pixel image is retained at box 56. At this point, a spike counter is initialized to a lowest count, such as 1, as indicated at box 58. These spikes are small groups of pixels registering relatively high intensity levels of light, generally the brightest of which being the corneal reflection 60 (FIG. 1a), also known as the corneal spike, and reflections from areas on or around a tear duct, such as spike 62. Additionally, there may be "hot pixels", such as pixel 64, which are pixels that are malfunctioning and providing an abnormally high intensity output. The counter of box 58 serves to keep a running count of the number of spikes selected for testing to determine if the selected spike is the corneal spike. While this algorithm will test up to 7 spikes, this value being determined empirically to give a high chance of finding the eyes, the corneal spike will typically be located by the second or third spike tested.

For testing these spikes, at box 66 the X and Y coordinates of a pixel registering a greatest light intensity in the pixel array is located, and the intensity and X and Y coordinates of this pixel stored at box 68. As shown in FIG. 1a, a 13 by 13 pixel array 70 is formed centered about spike 60. At box 72 (FIG. 2) array 70 is removed or clipped from pixel array 30, as will be further explained, so that the particularly high intensity pixel and surrounding pixels of the spike will not be reconsidered if it is determined that this pixel and surrounding pixels are not registering the corneal spike. The pixel array 30 minus the 13 by 13 array 70 is stored at box 74, and at box 76 a 96 by 96 pixel subarray that forms box 40 encompassing the iris as described above is formed centered about the 13 by 13 array which was subtracted. Subarray 40 is stored at box 78, and at box 80 subarray 40 is processed to determine whether subarray 40 registers the pupil. If the algorithm of box 80 determines that the pupil is located within subarray 40, then a flag or other indication is set at box 82. At box 84 an inquiry is made as to whether the pupil was located by the algorithm of box 80, and if not, then the program proceeds to box 86, where the test is made as to whether the spike counter is at its maximum count, which as stated is empirically set at 7 attempts. Here, if the pupil is not located by the time the spike counter reaches its maximum count of 7, then the program returns an indication that the pupil cannot be located. This may be due to jewelry or eyeglasses over or around the eye that generates reflections greater than the corneal spike, or the pupil/cornea may be so grossly abnormal or misshaped that the pupil simply cannot be located by the program. In the former instance, the jewelry or eyeglasses may be removed and the subject retested. In the latter instance, physical examination by a qualified individual may be indicated. If the spike counter reaches its maximum count without the pupil being located, then a flag indicative of such is set at box 88. This causes the program to return a null indication, or an indication that the pupil has not been located at box 90. If the spike count is not at its maximum count, as indicated by a YES at box 86, then the spike count is incremented by 1 at box 92 and the processes of boxes 66 through 84 repeated, and during each iteration thereof selecting the pixel registering a new highest intensity value. During these iterations, if the pupil is located at box 84, a new 96 by 96 array is cropped from the original half face image, this new 96 by 96 array being centered on the pupil, as indicated at box 92. The corneal spike in the new image is removed in a like manner as described for boxes 66, 68, and 72, and the new 96 by 96 pupil array is stored at box 96. A flag is set at box 98 indicating that the pupil array has been located, and the new pupil array is returned to the program at box 100 for processing to determine if diseased or abnormal conditions exist.

Figure 3:
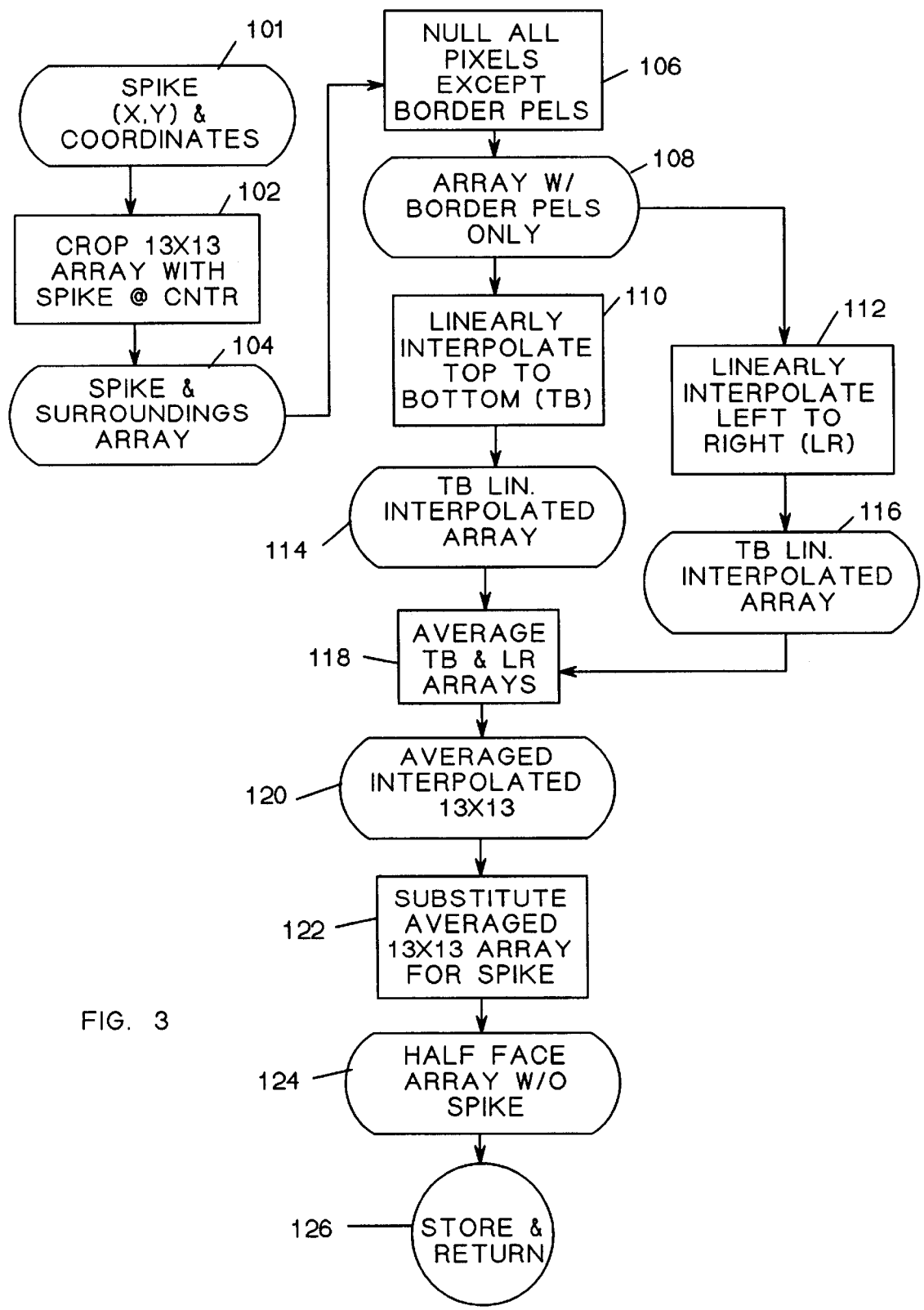
FIG. 3 is a flowchart showing a method for removing an intensity spike.
Figure 3A:
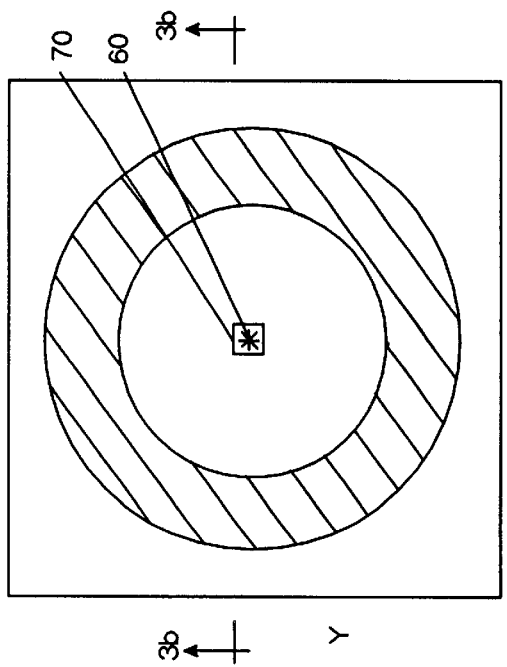
FIGS. 3a, 3b, 3c, 3d, and 3e illustrate particulars related to the flowchart of FIG. 3.
Figure 3D:
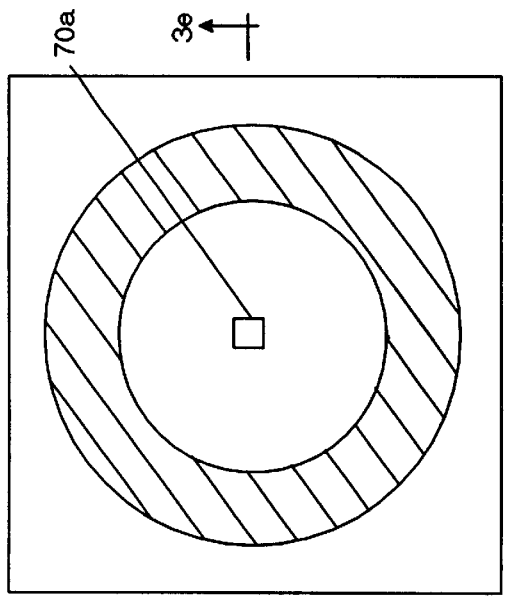
Figure 3B:
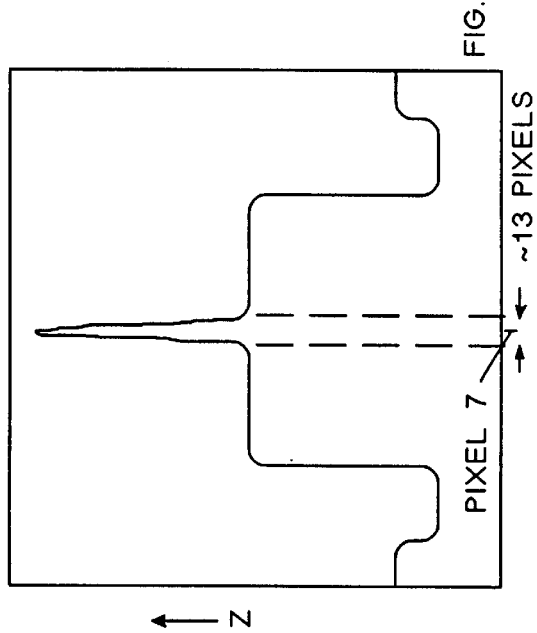
Figure 3E:
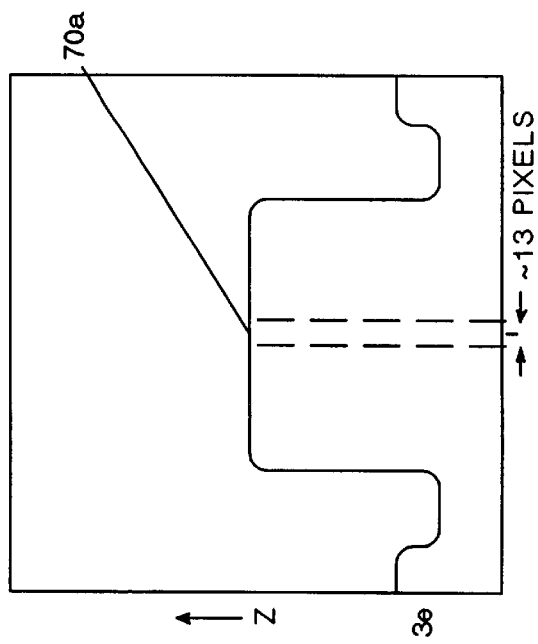
Figure 3C:
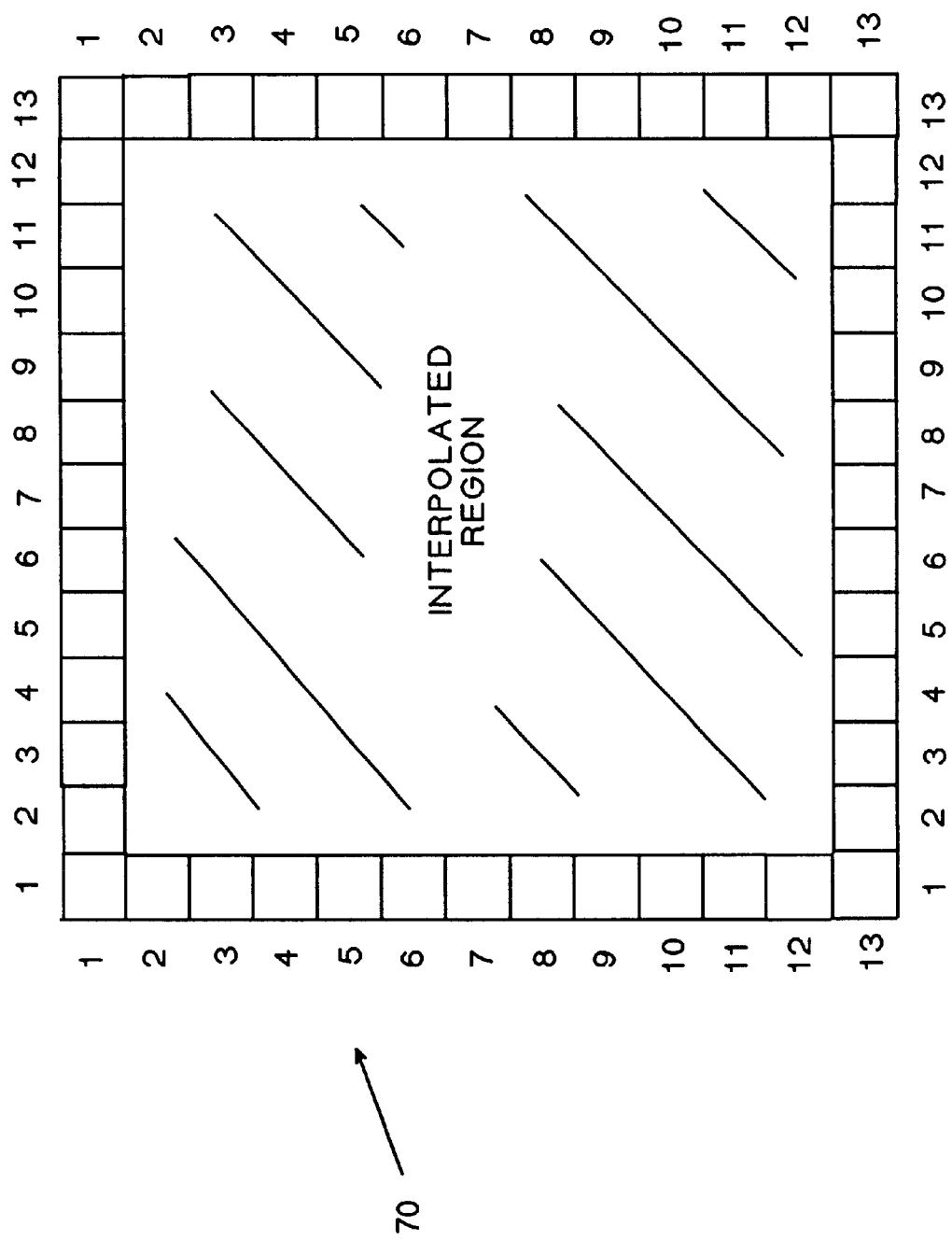

Referring now to the flow chart of FIG. 3 and FIGS. 3a, 3b and 3c, the algorithm for removing a spike at box 72 of FIG. 2 is shown. This algorithm is performed on each located spike, after which a test is performed to determine if the pupil is generally centered about the spike. Typically, only 2 or 3 attempts are needed to locate the corneal spike and corresponding pupil. At box 101 (FIG. 3) the X and Y coordinates of the selected spike are recalled, and at box 102 the 13 by 13 pixel array 70 (FIGS. 3a, 3c) as described above is centered about the located pike 60. In the graph of FIG. 3b, intensity values are plotted along the vertical axis and pixel position along horizontal axis line 3b—3b taken in FIG. 3a, which line extending through the center pixel registering the highest intensity. Array 70 is stored in memory at box 104, and at box 106 all pixels in the array are set to a null value except pixels bordering array 70, as shown in FIG. 3c. Here, rows 1 and 13 and columns 1 and 13 retain their intensity values, while interior pixels are set to the null value. At box 108 array 70 is stored in memory, and at box 110 light intensity values of pixels between the vertically opposed pixels of rows 1 and 13 are linearly interpolated between the vertically opposed values of the pixels in rows 1 and 13, generating a vertically interpolated array. At box 112 light intensity values of pixels between horizontally opposed pixels in columns 1 and 13 are linearly interpolated between the horizontally opposed values of the pixels in columns 1 and 13, generating a horizontally interpolated array of the same dimensions as array 70. At boxes 114 and 116 these interpolated arrays are stored in memory. At box 118 the vertically and horizontally interpolated arrays stored at boxes 114 and 116 are averaged, and the averaged array stored at box 120. At box 122 the averaged interpolated 13 by 13 array from box 120 is substituted for the original 13 by 13 subarray 70 in FIG. 3a. This removes the intensity spike from the array and smoothes intensity values in the area from which the spike was clipped, with the resulting array saved at box 124. As shown in FIG. 3d, the smoothed 13 by 13 array 70a is shown replacing the clipped 13 by 13 array which contained the corneal spike. FIG. 3e shows an intensity graph of the pupil with the interpolated array 70a bridging the area from which the spike was clipped.

Figure 4:
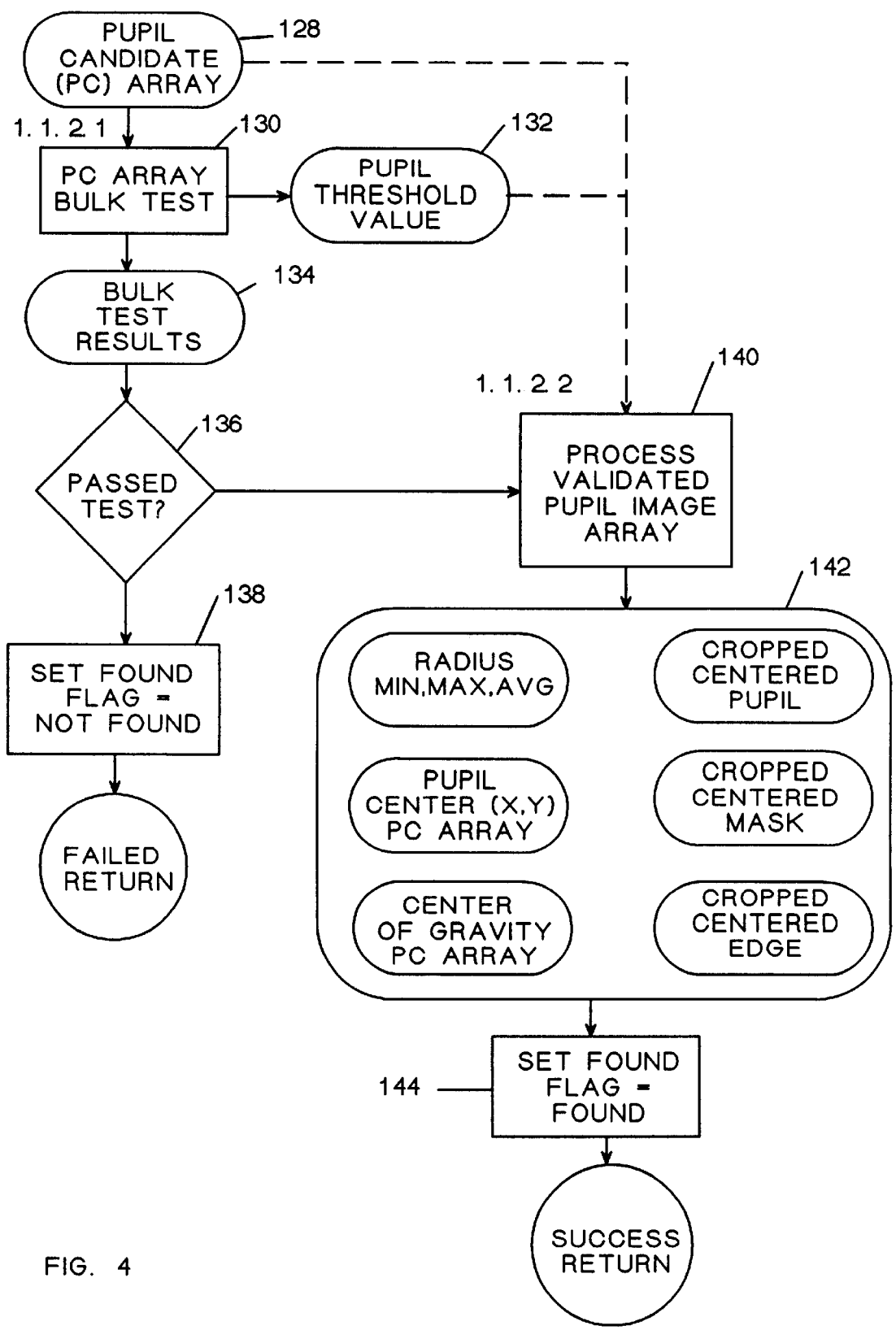
FIG. 4 is a flowchart showing a method for determining whether a pupil was located in the method of FIG. 3.

In the flowchart of FIG. 4, the process for determining whether the 96 by 96 pixel subarray saved at box 96 of the flowchart of FIG. 2 actually contains a pupil is shown. As stated earlier, this array may or may not contain the pupil of the subject eye. In this flowchart, the 96 by 96 array without the corneal spike which was generate at box 92 of FIG. 2 is retrieved at box 128, labeled PUPIL CANDIDATE ARRAY. At box 130, labeled PC ARRAY BULK TEST, a bulk test is made wherein various statistical and geometric characterizations are performed on the PUPIL CANDIDATE ARRAY of box 128. From these characterizations, a series of tests are performed which determine whether the PUPIL CANDIDATE ARRAY of box 128 is an image that contains sufficient structure to contain a pupil, as will be described. A threshold value for a pupil mask is also generated from the bulk test of box 130 and stored at box 132, as will be further explained. At box 134 the bulk test results are stored, and at box 136 a query is made as to whether the candidate array retrieved at box 128 passed the bulk test at box 130. In the instance where the array did not contain a pupil, then the answer here is NO, and at box 138 a flag is set indicating that a pupil was not found. At this point, the program returns to box 82 of FIG. 2, where the program proceeds as described at the inquiry of box 84. If a pupil was found in the 96 by 96 array, then at box 136 the answer is YES, and the program proceeds to box 140, Where the pupil is analyzed as will be described and various parameters and results about the subject pupil derived, these parameters and results saved at box 142. At box 144 a flag is set indicating that a pupil was found and the parameters and results stored, after which the program proceeds as described at the inquiry of box 84 of FIG. 2.

Figure 5:
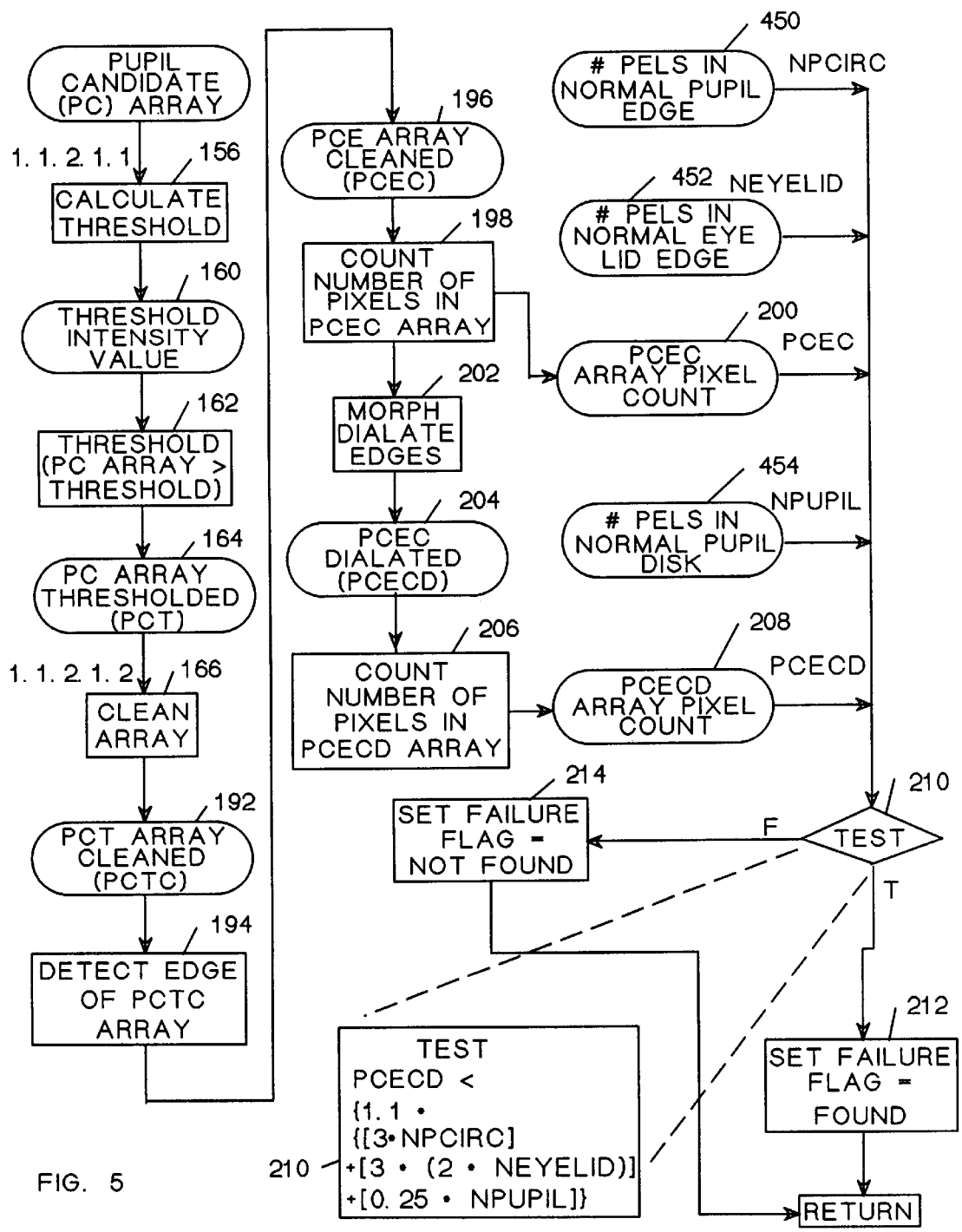
FIG. 5 is a flowchart showing particulars of the method of FIG. 4.
Figure 5A:
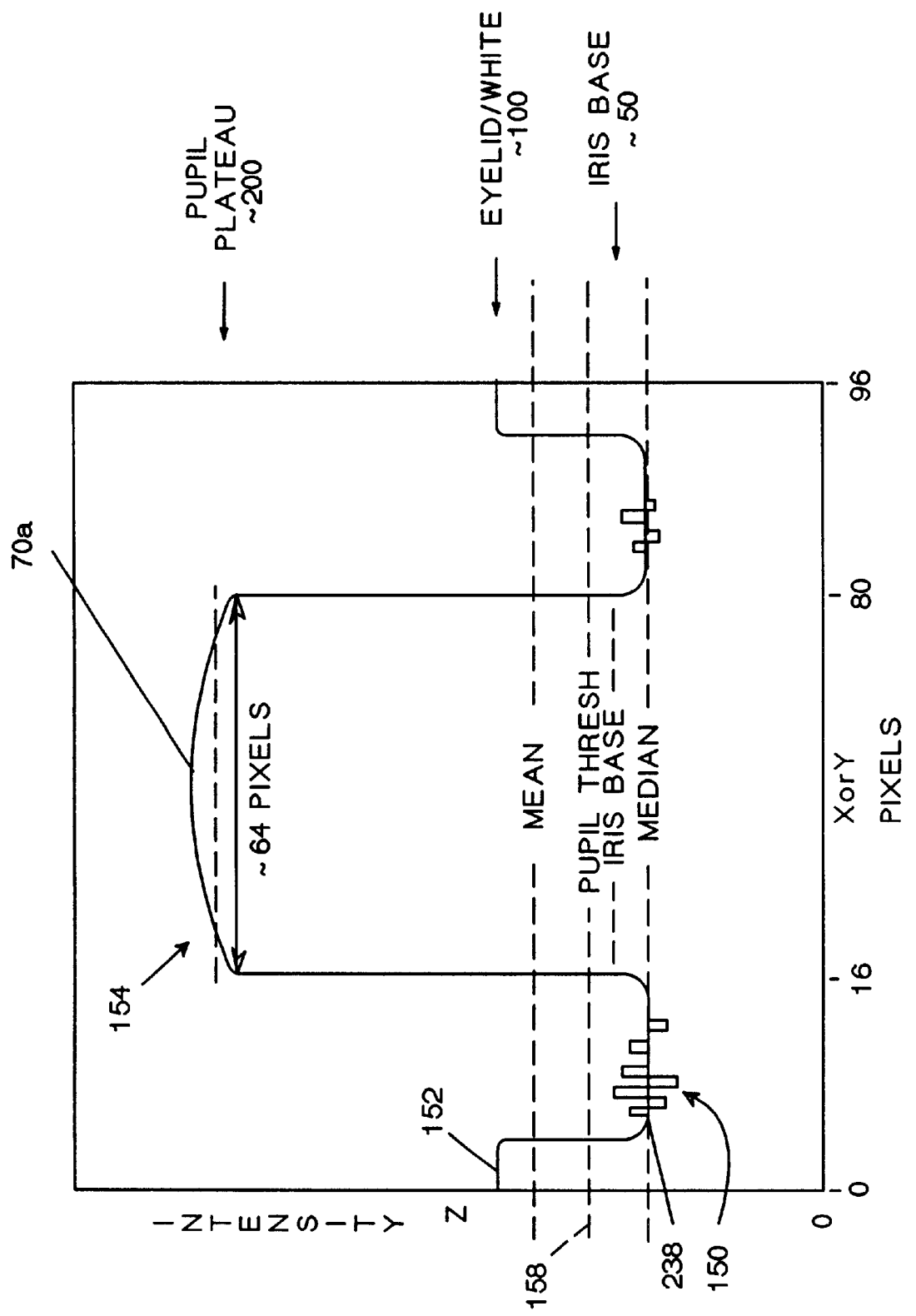
FIG. 5a is a graphical illustration of particulars relating to the flowchart of FIG. 5.

Referring now to the flowchart of FIG. 5, the bulk test of box 130 in the flowchart of FIG. 4 is shown. Here, the new 96 by 96 pixel array with the interpolated center region 70A where the spike otherwise would be and which was centered on where the spike was at box 96 of FIG. 2, is retrieved from memory. FIG. 5a shows a graphical representation of a typical 96 by 96 array of box 40 (FIG. 1a) containing a normal pupil. Here, in FIG. 5a intensity values of pixels are plotted on the vertical axis, and the X or Y axis of pixels extending through the center of the pupil array is plotted on the horizontal axis. After the scaling operation of box 54 of FIG. 2, the eye as a whole should register intensity values above 0, with pixels registering the iris generally indicating the lowest intensity values at 150 (FIG. 5a), these intensity values usually being around 50 or so. The next highest area 152 represents pixels that register either the whites of the eye or the eyelids, depending on the direction of the horizontal axis, these values being around 100 or so. Pixels registering the pupil, as indicated at 154, generally have values of about 200 or so. Where the pupil is centered in the 96 by 96 array, the first 16 or so pixels from the edge of the array register the whites of the eye and the iris, with the next 64 pixels or so registering light from the pupil. At about pixel 80, pixels again begin registering the iris and whites of the eye, as indicated along the horizontal axis of FIG. 5a.

A threshold of intensity values is calculated at box 156 18 (FIG. 5), which will be described hereinafter, this threshold being slightly higher than intensity values registering the iris, as indicated by threshold 158 (FIG. 5a). The threshold intensity value is stored at box 160, and at box 162 those pixels having light intensity levels greater than the threshold are assigned a value of 1, and those pixels having a light intensity value less than the threshold are assigned a value of 0. At this point, pixels registering the pupil have a value of 1, and pixels registering areas outside the pupil generally have a value of 0. At box 164 the thresholded array is stored, and at box 166 a process is begun that results in a mask array approximately the same size as the subject pupil.

Figure 5B:
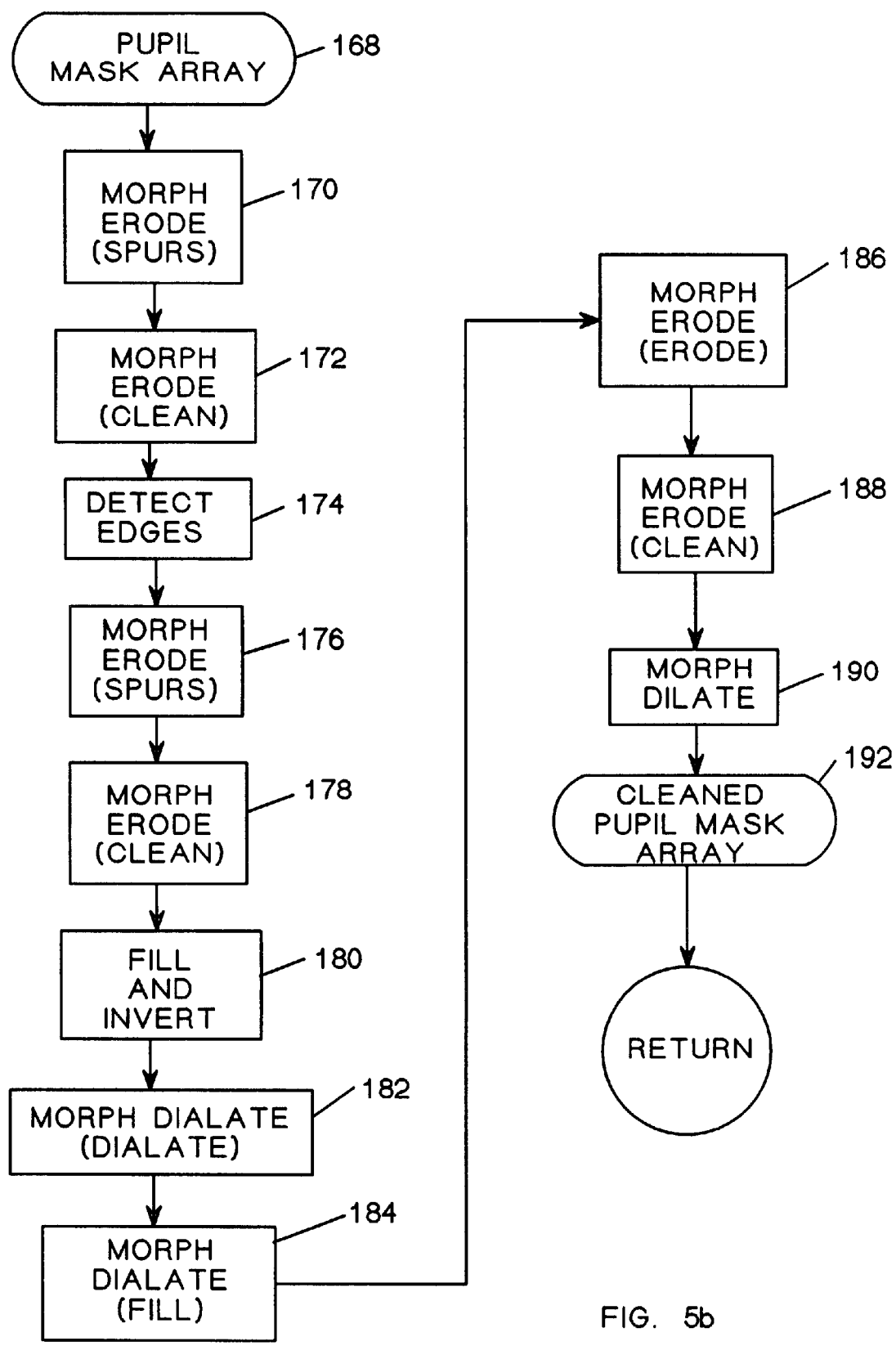
FIG. 5b is a flowchart of a "cleaning" process of FIG. 5.
Figure 5G:
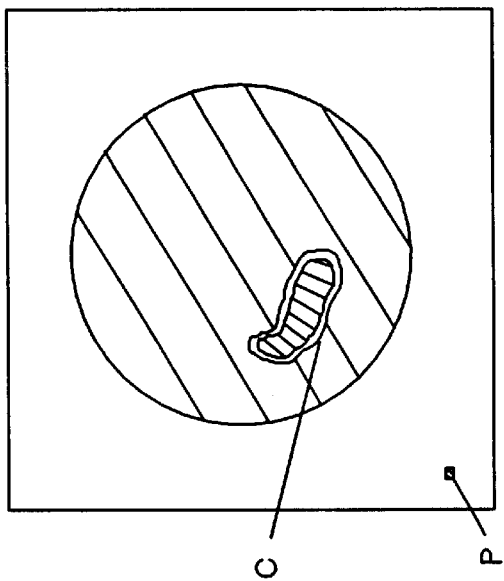
Figure 5F:
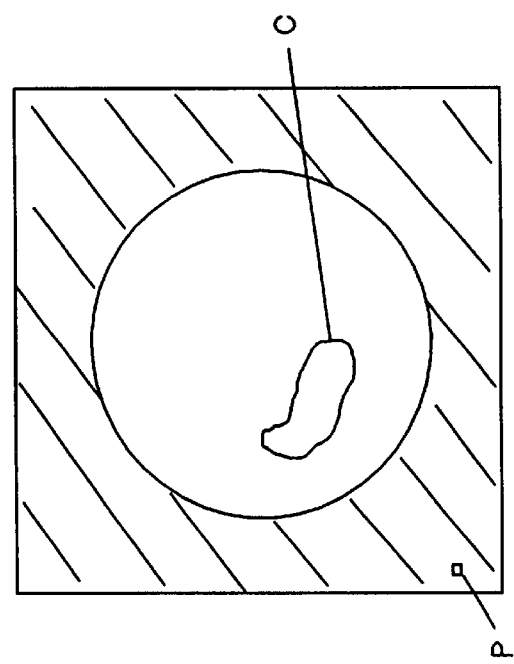

This process is facilitated by MATLAB™ and the MATLAB IMAGE PROCESSING TOOLBOX™, MATLAB™ being a program developed by MATHWORKS INCORPORATED™ of Cambridge, Mass., and which provides tools for advanced image processing and morphological operations. Particularly, a "cleaning" operation, such as that shown in the flowchart of FIG. 5b and put together using the MATLAB™ tools, serves to homogenize the thresholded pixel values inside the pupil to a value of 1 and outside the pupil to a value of 0. It is to be recalled that at this point the normal pupil in the thresholded array is indicated by a circular disk of pixels, most of which were above the threshold value and thus are assigned a value of 1. Areas outside the pupil have intensity values that generally were below the threshold value, and thus are assigned a value of 0. However, the areas inside and outside the pupil invariably contain a small number of pixels opposite the predominate value. As shown in FIG. 5c, groups of two adjacent pixels, designated S may exist, these groups known as "spurs". Larger groups of pixels of the opposite value may also exist, particularly where there is a cataract, as indicated at C. Of course, there may also be a scattering of single pixels and groups of pixels of the opposite value, as shown by pixels P. In the cleaning algorithm of FIG. 5b, and at box 168, the thresholded array from box 164 of the flowchart of FIG. 5 is retrieved, and at box 170 (FIG. 5b) a MORPH ERODE SPURS operation is performed. This converts one pixel of the spurs S from a 1 to a 0 value, leaving a single pixel of a value of 1, as shown by single pixels Ps in FIG. 5d. At box 172, a MORPH ERODE CLEAN operation is performed, this operation inverting the value of single pixels P in FIG. 5c having a 1 value in an area of pixels of 0 value, as shown in FIG. 5d by the reversed pixels P'. At box 174, an edge detection algorithm, such as the routine BWPERIM from MATLAB™, is performed, which as shown in FIG. 5e detects edges in the array, such as edge Ep of the pupil, edge Ee of the eyelid, edge Ei of the iris, and Ec of the cataract. The cataract C, when the edge detection algorithm is performed, may be detected as a series of relatively closely intertwined irregular lines. Edges are represented by contiguous lines of pixels of a value of 1, while non-edges are represented by pixels having a value of 0. As such, the edge detection algorithm changes most of the pixels in the cleaned and thresholded pupil image to a value of 0, with the exception of the pupil circumference, eyelid edges, obstructive cataracts or other artifacts that obstruct transmission of light through the pupil which as stated, may become evident as irregular intertwined edges. Small numbers of isolated pixels of the opposite value may have survived the process including box 174, such as pixel P. At box 176, the MORPH ERODE SPURS operation may again be performed, followed by a MORPH ERODE CLEAN operation at box 178. As described, these two last-named operations reverse the value of one of the pixels of a spur and reverses the value of the remaining pixel of the spur in the edge detected array. At box 180 a FILL AND INVERT operation is performed, the FILL operation beginning at the border of the array and serving to convert values of pixels of open areas from 0 to 1, and the INVERT operation serving to reverse the value of all pixels in the array (0 to 1 and 1 to 0). As such, pixels of non-edges of the eyelid Ee and iris Ei ( FIG. 5e) are filled in and thus reversed from a 0 value to a 1 value, as shown in FIG. 5f because they do not completely enclose an area, as is the case with the pupil. In the FILL AND INVERT operation, pixels which are of a value of 0 and that are not fully enclosed by a border of pixels having a border of 1 will be reversed to a 1, while pixels of a value of 1 and that are not fully enclosed by a border of pixels having a value of 1 are nonresponsive to the FILL operation. When inverted, the pixels of a 0 value prior to the FILL operation which are not fully enclosed by a border of pixels having a value of 1 assumes a value of 1, as shown for pixel P and the pupillary disk in FIGS. 5f and 5g. After the INVERT operation, as shown in FIG. 5g, pixels inside the pupil are reversed to a value of 1 and pixels outside the pupil are reversed to a value of 0. At box 182 a MORPH DIALATE DIALATE operation is performed, which expands the area of all objects in the array having a value of 1 by 1 pixel around the entire inner region and outer region of the perimeter of the objects. This has the effect of filling in spurious small groups of 0 value pixels that are still imbedded in the pupillary disk. This operation also returns the size of the pupil disk to occupy the same border as in box 174, the pupil having been reduced by 1 pixel at box 180. At box 184 a MORPH DIALATE FILL operation is performed, this operation reversing single pixels of a 0 value imbedded in the pupil disk to a value of 1. This fills in any residual single pixels having a value of 0 in the pupillary disk to a value of 1. At box 186 a MORPH ERODE ERODE operation is performed, this operation changing the value of pixels along all edges from value of 1 to a value of 0. This eliminates artifacts in the array up to 2 pixels thick, and reduces the radius of the pupillary disk by 1 pixel. At box 188 a MORPH ERODE CLEAN operation is done, which again locates single pixels of a 1 value and converts them to a 0 value. At box 190 a MORPH DILATE operation is performed, which adds a border of 1 pixel around every edge of objects in the array, returning the pixel to its original size after the dilation operation of box 182. This reverses the loss of radius and area of the pupillary disk due to the erode operation of box 186. This results in a cleaned pupil mask array where pixels inside the pupil are of a value of 1 and pixels outside the pupil have a value of 0, as shown in FIG. 5g, except without the presence of pixel P.

The cleaned pupil mask array is stored at box 192 (also 192 in FIG. 5), and the program returns to box 194 of the flowchart of FIG. 5, where the cleaned pupil mask array from box 192 is edge detected at box 194 and the cleaned edge detected array stored at box 196. At box 198 the number of pixels in the array from box 196 are counted, and the count of these pixels stored at box 200. At box 202 a DILATE operation is performed, this operation serving to thicken the pixel circumference by 1 pixel on the inside and outside of the circumference pixels. This expands the border or thickens the edge of the pupil by a margin of 2 pixels. At box 204 the dilated array from box 202 is stored, and at box 206 the number of pixels in the dilated array from box 204 are counted, and this count stored at box 208. The parameters as indicated at boxes 210, 212, and 214 are read, the parameter of box 210 being the number of pixels of a 1 value in a normal pupil circumference. This is found by taking an average of the number of pixels in the circumference of pupils from a database of pupils. Likewise, at box 212 the number of pixels in a normal eyelid edge is retried, this figure also determined by taking an average of the number of pixels of a 1 value in the edge of eyelids of a database of eyes. At box 214 the number of pixels in a normal pupil disk mask is retrieved, and which is also an average from a database of normal pupils. At box 200 the number of pixels in the cleaned pupil edge array of box 198 is retrieved, and at box 208 the number of pixels in the dilated pupil edge array from box 206 is retrieved. These parameters are applied to the test at box 210, which basically compares the number of pixels having a value of 1 in the candidate array against a count of the pixels expected to be 1 in a normal eye after having been put through the process of FIG. 5. In this comparison, and as illustrated at box 210*a*, the number of pixels in the circumference of the normal pupil is multiplied by 3 to account for the number of pixels in the subject pupil after the MORPH DILATE process of box 202, adds the number of pixels for 2 eyelids, which is roughly the number of pixels in a diagonal line through the array, which is also multiplied by 3 to compensate for the number of pixels added in the dilation process, and adds ¼ the number of pixels in the area of the pupil, this figure approximating the number of pixels occupied by a significant cataract after the dilation of box 202. The results of the above is multiplied by 1.1, which is representative of the factor of those noise pixels which may have eluded the cleaning processes. If the count of pixels stored at box 208 is less than the number of pixels obtained from the normal eye with the cataract factored in as calculated in box 210*a*, then the array is returned as containing a valid pupil and a flag indicating this is set at box 212. If the pixel count for the subject array is greater than the count for the normal eye, then the array is rejected as not containing a valid pupil and a flag indicating this is set at box 214. In this instance, the program is returned to box 138 of FIG. 4 and from there to the test at box 84 of the flowchart of FIG. 2, where the spike counter is incremented and the next brightest pixel in the half face image is selected to determine if it is part of the corneal spike.

Figure 6:
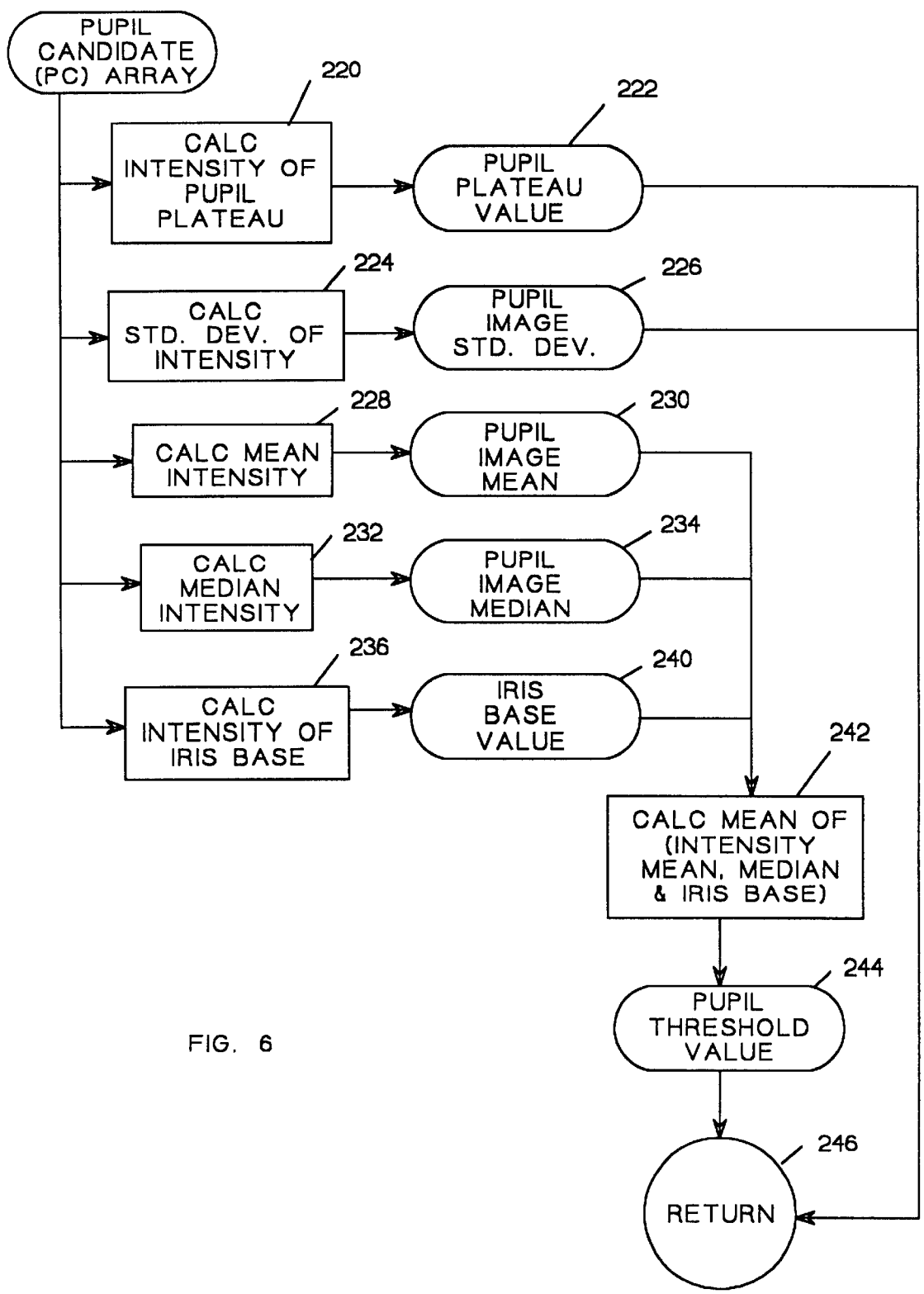
FIG. 6 is a flowchart illustrating particular details of the flowchart of FIG. 5.

The CALCULATE THRESHOLD algorithm used to calculate the threshold at box 156 of the flowchart of FIG. 5 is shown in greater detail in the flowchart of FIG. 6 and the graph of FIG. 5*a*. For this threshold, 5 parameters are calculated as shown in boxes 220–236, which are the average intensity of the pupil plateau, the standard deviation of all pixels in the array, the mean intensity of all pupils in the array, the median intensity of all pupils in the array and the average intensity of the iris base, respectively. At box 220, and beginning with a threshold intensity value of 1, the number of pixels in the pupil candidate array with a greater intensity value than 1 are counted. If this count exceeds the number of pixels expected in a normal pupillary disk as determined from a database of normal pupils, then the threshold intensity value is incremented by 1 and the process repeated until the number of pixels from the pupil array with a value greater than the threshold intensity value is less than the expected number of pixels in a normal pupil disk as determined from a database of normal eyes. The threshold at this point is stored as the pupil plateau value at box 222. At box 224 the standard deviation is calculated and the result stored at box 226. The mean intensity value of all intensity values in the 96 by 96 array is calculated, as shown at box 228, and the result stored at box 230. The median intensity of all pixels in the 96 by 96 array is calculated at box 232, and the result stored at box 234. The average value of the intensity of the iris base is calculated at box 236, which may be done in a similar manner as calculation of the pupil plateau at box 220. The only difference between the calculation of box 236 and the calculation of box 220 is that instead of using the number of pixels in a normal pupil disk, a value equal to the total number of pixels in the pupil array (nominally 96 by 96) minus the expected number of pixels in a normal iris (from a database of normal eyes) is substituted. This has the effect of finding the iris base (238 in FIG. 5a). The average intensity value of the iris base is stored at box 240, and at box 242 the average of the pupil image mean, the pupil image median, and the iris base value is calculated. This average is stored at box 244, and the program is returned at box 246 along with the values of the pupil plateau calculated at box 222 and the pupil standard deviation calculated at box 226 to box 160 of the flowchart of FIG. 5.

Figure 7:
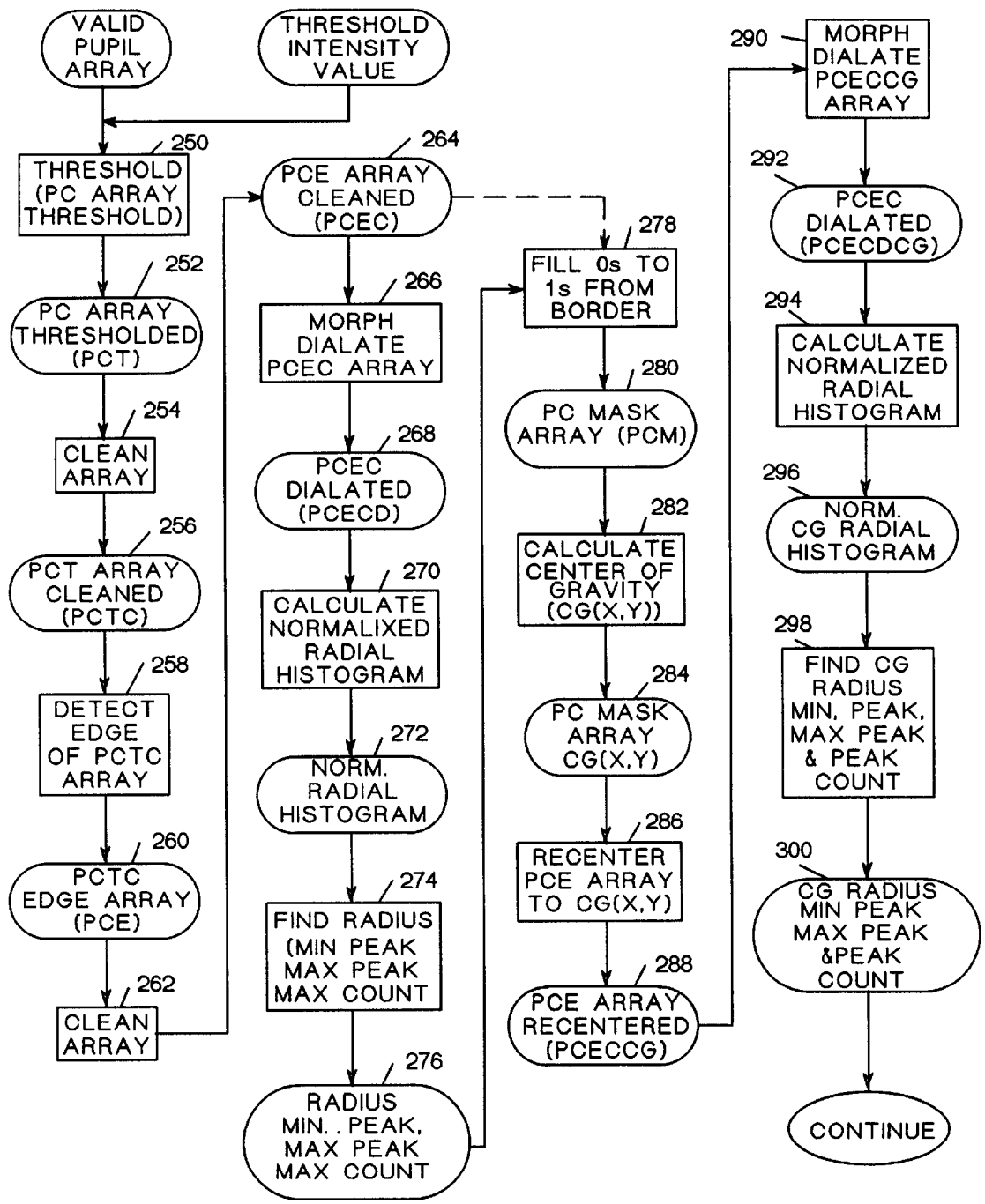
FIG. 7 is a flowchart illustrating processing of a pupil array.
Figure 7A:
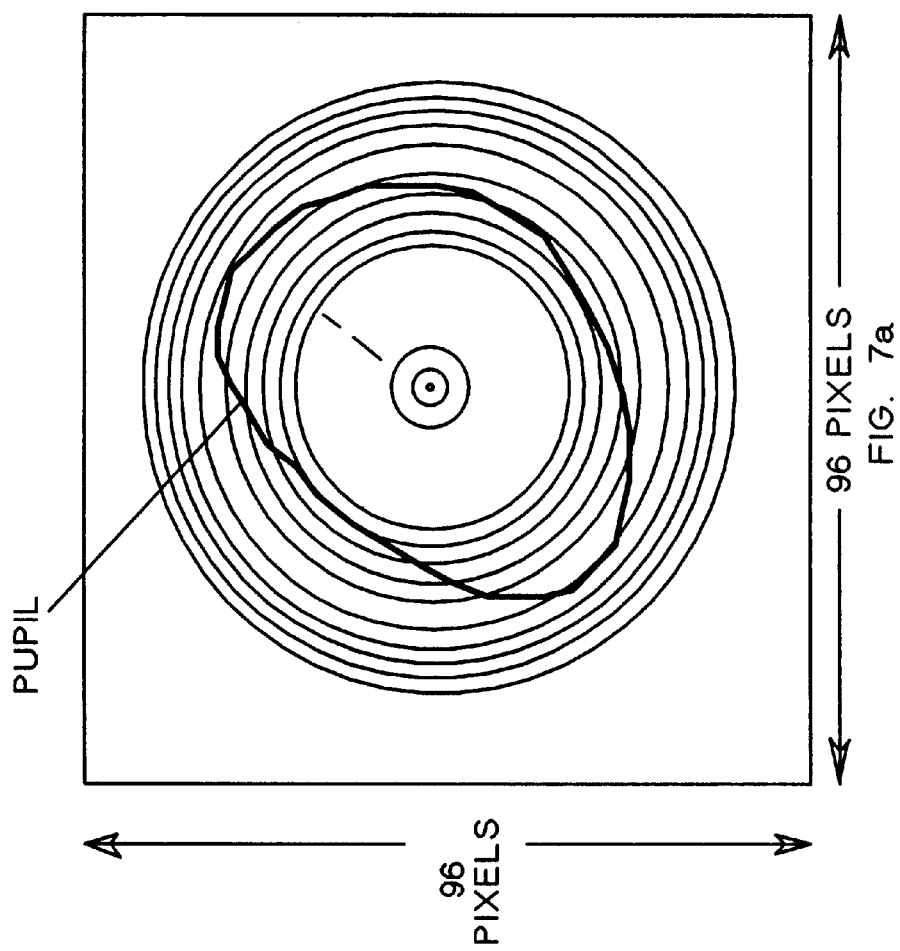
FIGS. 7a and 7b graphically illustrate particulars relating to the flowchart of FIG. 7.
Figure 7B:
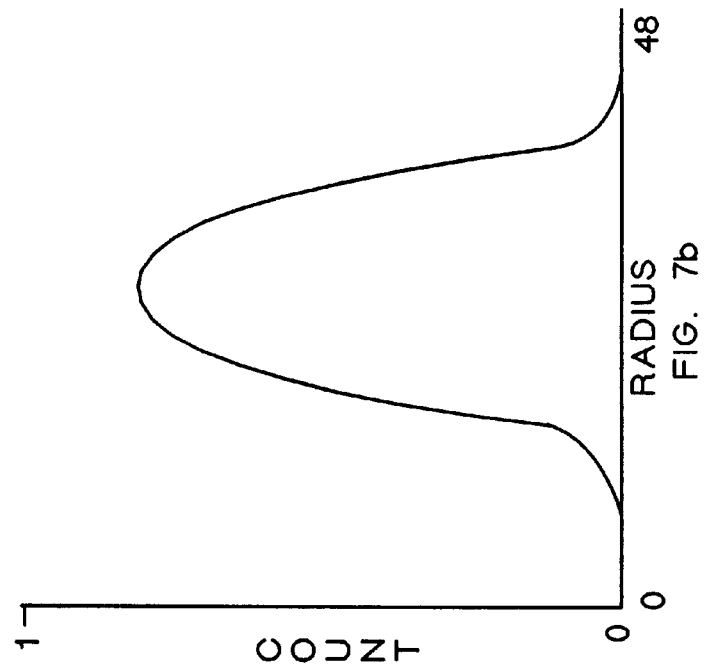

Referring now to the flowchart of FIG. 7 and associated drawings, processing of the validated pupil image array at box 140 of the flowchart of FIG. 4 is shown. In this process, the pupil array at box 128, along with the threshold value at box 132, is retrieved. It will be noted that boxes 250–264 are identical to boxes 156–196 of the flowchart of FIG. 5, and perform the same functions as described in the foregoing. At box 266 the two processes diverge, with the process of the flowchart of FIG. 7 indicating a MORPH DILATE operation of the pupil edge array, with the dilated array saved at box 268. This step thickens the pupil edge along with any artifacts that may be in the array, and has the effect of producing a single (as opposed to a double) peaked radial histogram for off-centered pupils in the following steps. Here, the MORPH DILATE operation of box 266, by expanding the circumference of the subject pupil, increases the available number of pixels that are counted. This has the effect of allowing greater misalignment of the center of the subject pupil with the origin of the histogram circles, which otherwise would develop the double peaks as described. The histogram is normalized by dividing the total number of corresponding pixels at each radius by 2a multiplied by radius R of the histogram radius. At box 270 a normalized radial histogram is calculated on the dilated pupil disk stored at box 268. As shown in FIG. 7a, the normalized radial histogram algorithm begins at the center of the 96 by 96 array and increments radially outward at a rate of 1 pixel or so per step. At each step, a circumference is defined for that radius, and the number of pixels in the defined circumference generated by the histogram that also corresponds to pixels registering the imperfect circumference of the pupil counted. The count of corresponding pixels, in fractions of the total number of pixels registering in the circumference of a perfect circle at that radius, is plotted along the vertical axis of the radial histogram plot of FIG. 7b, and the radius at which the fractional count is taken is plotted along the horizontal axis. Ideally, where the subject pupil is centered at the same center as the center of the pupil edge array (96 by 96) and coincidentally the radial histogram, most of the pixels registering the circumference of the subject pupil will coincide with one or two of the circumferences generated by the radial histogram process. When plotted, a sharp spike is thereby generated in this radial histogram for reasonably circular and co-centric pupil edges. Where the circumference of the subject pupil is irregular or not centered at the same center as the center of the histogram circles, as shown in FIG. 7a, then the plot spreads out as shown for plot P. The radial histogram plot data is saved at box 272, and at box 274 the minimum and maximum radii for the histogram and the highest count M are found. Here, the minimum radius is the radius of the smallest histogram circle that intersects some fraction of the circumference of the subject pupil edge and the maximum radius is the largest histogram circle that intersects some fraction of the outermost pixels of the subject pupil edge. The highest count occurs when the greatest number of pixels of the circumference of the histogram circle coincide with the most pixels in the imperfect circumference of the subject pupil edge. At box 276 the minimum and maximum radii and the peak count are stored.

At box 278 the cleaned array from box 264, which contains 28 an image of the subject pupil edge, is retrieved and a FILL operation beginning at the border of the array is performed. This Fill operation, beginning at the border of the array, changes pixels having 0 values to 1 values. Pixel values inside the pupil circumference, which predominately have a value of 0, are unchanged. This mask array is stored at box 280, and at box 282 the center of gravity (CG) of the mask image of the pupil is calculated, as should be apparent to those skilled in the art, and this array stored at box 284. At box 286 the edge mask image of the pupil stored at box 264 is centered, placing the calculated center of gravity of the pupil at the center of the 96 by 96 array. The resulting array is stored at box 288, and at box 290 a MORPH DILATE operation is performed, reversing the value of a layer of pixels on the inside surface and outside surface of the edge of the pupil to a value of 1. This dilated pupil array is stored at box 292, and at box 294 a normalized radial histogram is performed on the data of box 292 using the identical procedure as described for box 270. At box 296 the normalized radial histogram plot is stored, and at box 298 the minimum and maximum radii and the peak count are found as described for box 274. At box 300 the minimum and maximum radii and the highest count for the CG centered pupil edge array count (box 286) are stored, and the program proceeds to the flowchart of FIG. 8, where at box 302 the parameters stored at boxes 276 and 300 are retrieved. The best centered of these arrays is selected according to which has the highest normalized maximum count. In the event parameters from these two arrays are closely similar or the same, then the best centered array is selected according to which has the smallest difference between the minimum and maximum radius. At box 304 the array which was selected at box 302 is stored along with its center coordinates. At box 306 a Hough transform for circles is performed, which is well known to those skilled in the art of image processing, the Hough transform serving to develop a circle having a best match to the circumference of the pupil edge image in the array stored at box 264 (FIG. 7). This resulting circle from the Hough transform is used to determine a best fit radius of the circular shape of the pupil. Typically, a best fit circle developed by the Hough transform will match from about 30% to about 70% of he pixels of the circular shape of a normal pupil, the deviations from 100% resulting from minor imperfections in the circularity of a normal eye, and also from the digital nature of the image processing.

Figure 8A:
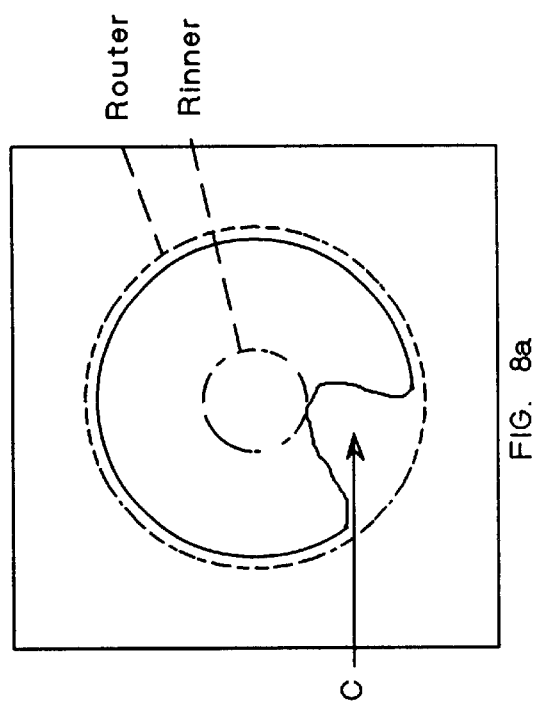
FIGS. 8a, 8b, 8c, 8d, and 8e graphically illustrate particulars of the flowchart of FIG. 8.
Figure 8:
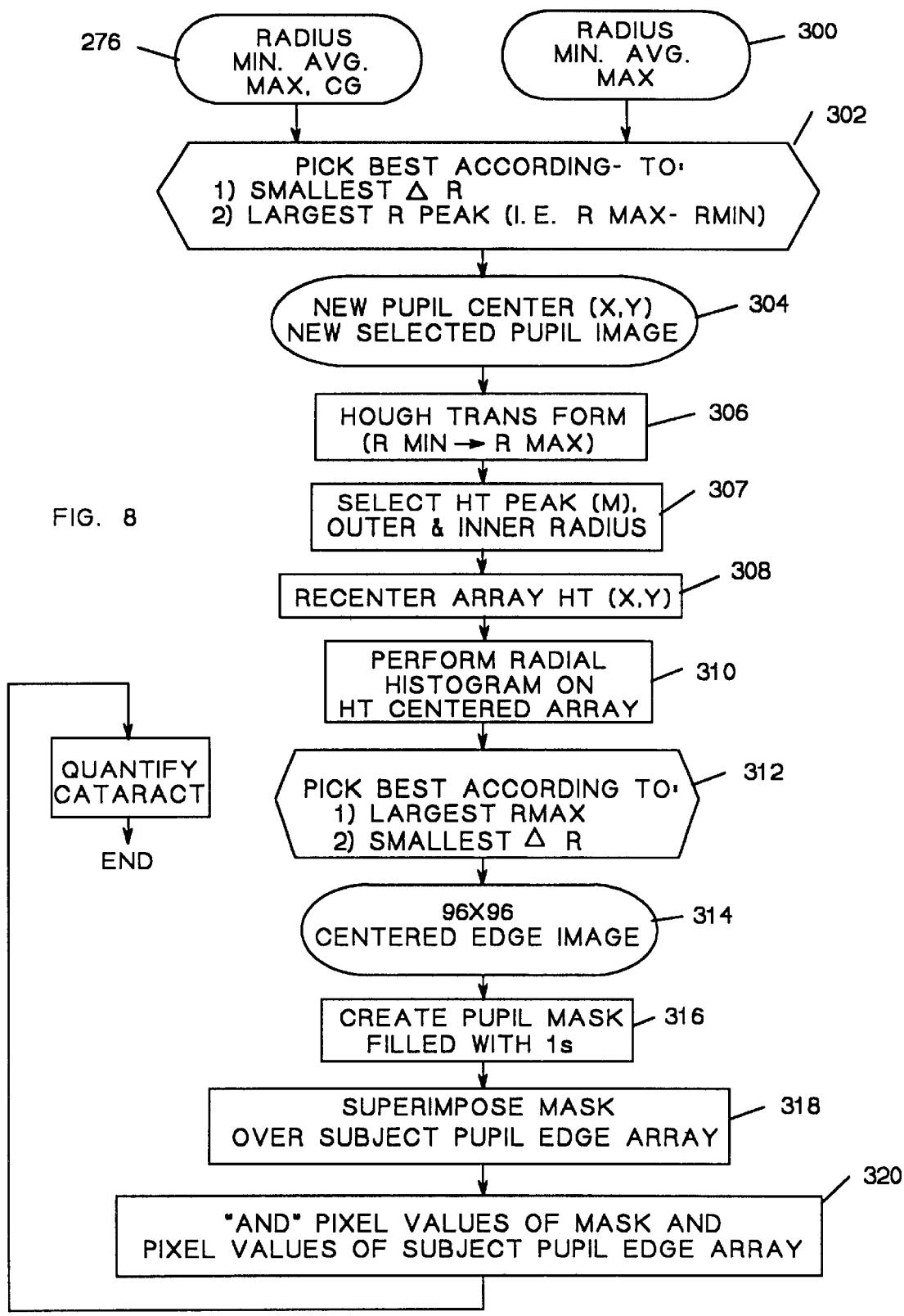
FIG. 8 is a continuation of the flowchart of FIG. 7.
Figure 8C:
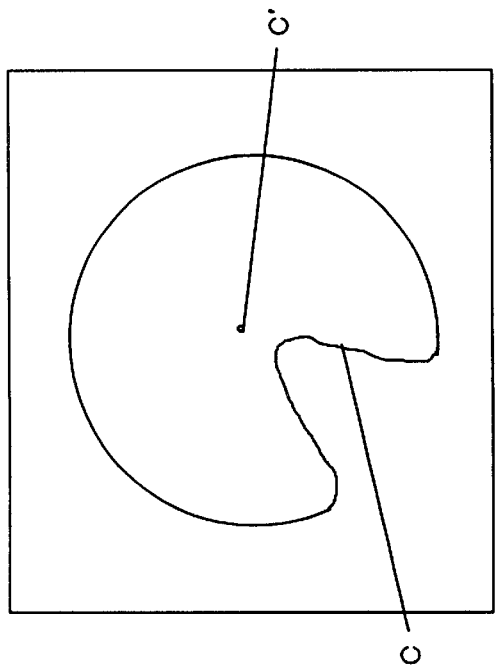

The parameters R min and R max stored at box 276 of FIG. 7 are retrieved, and are used as the starting and ending points respectively for using the Hough transform to search for the circular shape and size of the pupil. The Hough transform may also be used in a process to determine whether a pupil has an intrusive obstructive cataract, and to quantify the extent of the cataract. Referring to FIG. 8a, the pupil disk from box 264 (FIG. 7) is shown, this pupil containing an intrusive cataract C. At box 306 (FIG. 8) a Hough transform search is performed. Beginning at the minimum radius R min of the pupil array stored at box 264, the Hough transform is done for each radius R starting at R min, and the diameter 2×R min is incremented by 1 pixel for each radius tested. When the Hough transform is tested through all radii out to the maximum diameter R max, the search is terminated.

The minimum value of the accumulator array from the Hough transform for each radial increment tested gives both the likelihood of a circle of that radius existing in the image, as well as the X, Y coordinates of the center of that circle. The maximum value of the accumulator array from the Hough transform, for each radius tested, may be plotted as shown in FIG. 8b, with the inner radius represented at point R inner, the outer radius at point R outer and a peak, or best match, as represented at point M. The best matching circle to the pupil circumference in the image is shown at point R outer and is found from the radius corresponding to M. R inner is found by locating the largest positive slope (derivative) of the curve of FIG. 8a which also resides to the left (side of R min ) of M. This process provides two parameters R inner and R outer, R inner being the innermost excursion of a intrusive obstructive cataract and R outer being the outermost portion of the pupil circumference. The ratio between R inner and R outer is an indication of the severity of an intrusive obstructive cataract in the pupil image. Where this ratio approaches 1, differences between the inner radius and outer radius are small, and the likelihood of an intrusive obstructive cataract is small. Conversely, a larger spread between the inner radius and outer radius indicates an intrusive obstruction due to a cataract or other foreign object in the transparent region of the eye. The point of best match M developed by the Hough transform search is used as the center point to recenter the pupil array from box 264 (FIG. 7) and store the result at box 308. At box 310 a normalized radial histogram is performed on the recentered array stored at box 308, and at box 312 a selection is again made as to which of the arrays developed by the Hough transform or the selected array from box 304 is best centered. The test at box 312 is identical to the test at box 302, i.e. which has the largest peak count and in the case of a tie, which has the smallest difference between R min and R max. The result at box 314 is an image of the edge or outline of the pupil of the subject.

Figure 8E:
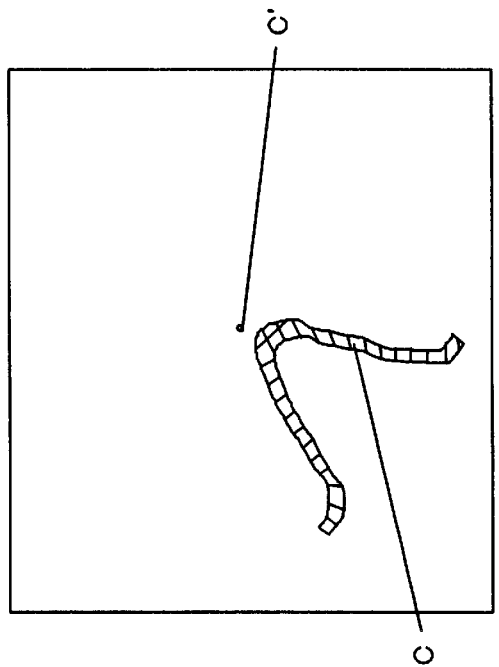
Figure 8B:
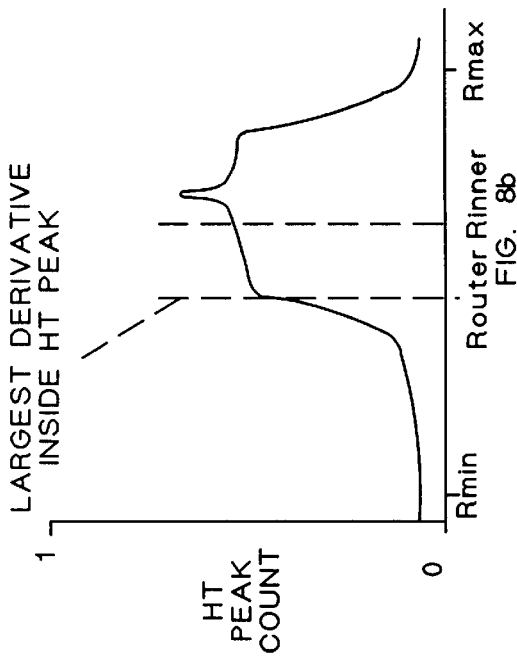
Figure 8D:
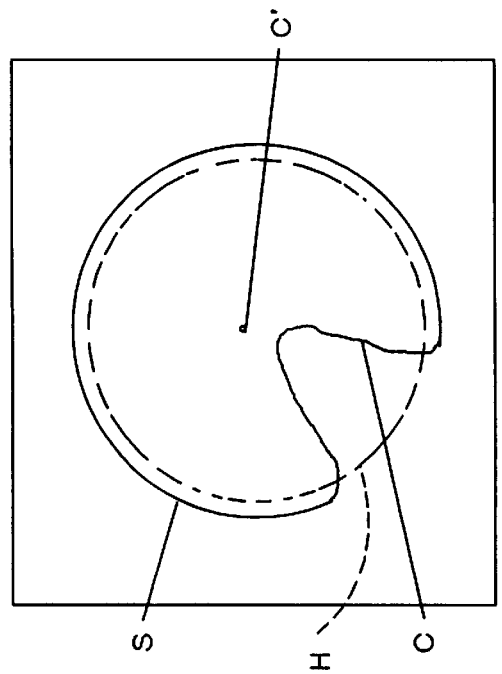

For isolating or quantifying the cataract, reference is made to the flowchart of FIG. 8 and FIGS. 8c, 8d, and 8e. Here, at FIG. 8c the pupil edge array of the subject from box 314 is retrieved. At FIG. 8d a centered solid disk binary mask array is created from the parameter R outer from the Hough transform of box 307 and reduced in diameter by 1 or 2 pixels, as shown by the dashed line H, and at box 318 (FIG. 8) the mask array is superimposed over the newly centered edge array from the subject (box 314), as indicated by the solid line labeled S in FIG. 8d. The mask array H is filled with pixel values of 1, and at box 320 an AND function is performed between corresponding pixels in the subject edge array and superimposed mask array. Here, ANDed pixels which have dissimilar values of 0 and 1 result in a value of 0, and where pixels of like values are ANDed the result is a pixel value of 1. As such, the intrusive edge C of the cataract will appear in the resultant array, as shown in FIG. 8e, this edge resulting from pixels in the edge array from the subject having a value of 1 being ANDed with pixels having a value of 1 in the mask array. By reducing the diameter of the mask array by 1 or 2 pixels, the circular portion of the edge array of the subject that does not involve the edge of the cataract is not coincident with the edge of the mask array, resulting in 0 values for the edge of the subject array when the AND operation is performed. Quantification of the cataract may be done by the extent to which the edge C ingresses into the area of the pupil. Here, closer pixels to the center C' of the pupil edge array may be weighed to a greater extent in a quantification calculation.

Figure 9B:
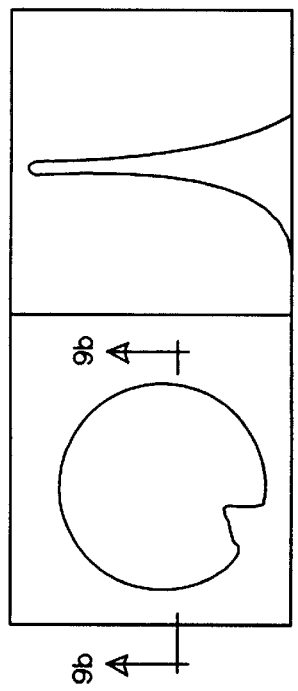
FIGS. 9, 9a, 9b, 9c, and 9d graphically illustrate quantification of opacities of an eye.
Figure 9C:
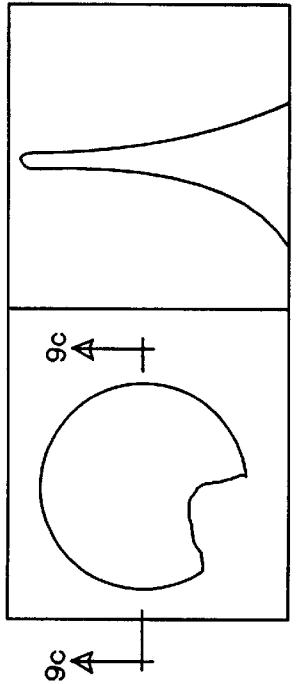
Figure 9D:
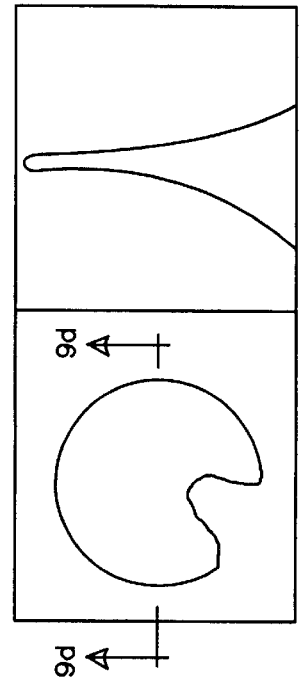
Figure 9A:
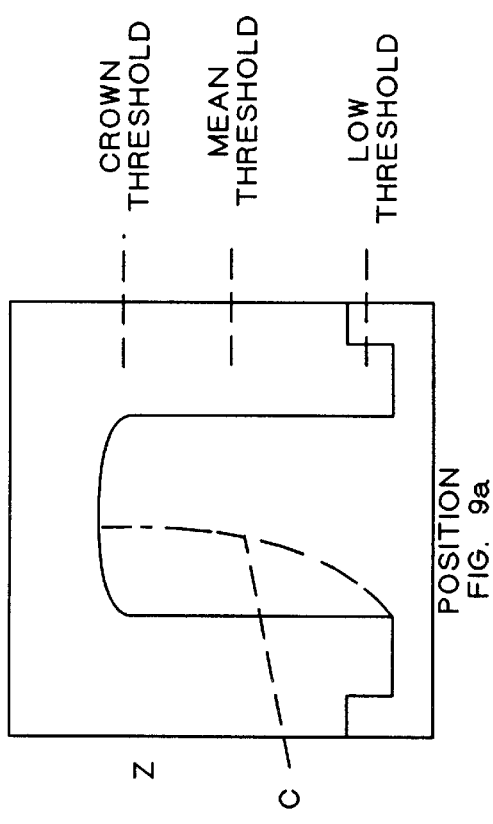
Figure 9:
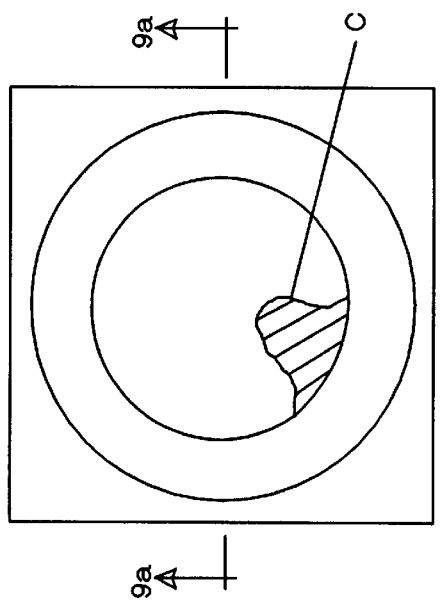

Further quantification of a cataract may be done as shown in the process shown in FIGS. 9–9d. Here, the pupil P of FIG. 9 contains an intrusive obstructive cataract C that extends inward from the edge of the pupil toward the center of the pupil. As shown in FIG. 9a, light intensity levels of pixels lying along line 9a of FIG. 9 are plotted vertically and pixel positions along line 9a are plotted along the horizontal axis. By taking a series of radial histograms at different thresholds of intensity levels of the pupil, as shown for the histograms of FIGS. 9b, 9c, and 9d that are taken at low, medium and high thresholds, respectively, the statistical moments of mean, standard deviation, skewness and peakedness (and higher moments if deemed useful from empirical assessments) may be determined for each radial histogram. These statistical moments may be used to classify the degree of severity of the cataract. For example, in a normal pupil, a radial histogram taken at the three thresholds described will each generate a symmetrical, narrow spike. In contrast, the radial histograms of FIGS. 9b, 9c, and 9d are fattened, which results in a significantly larger standard deviation, in addition to portraying a tail in the distribution towards smaller radii, which results in larger skewness values.

Figure 10:
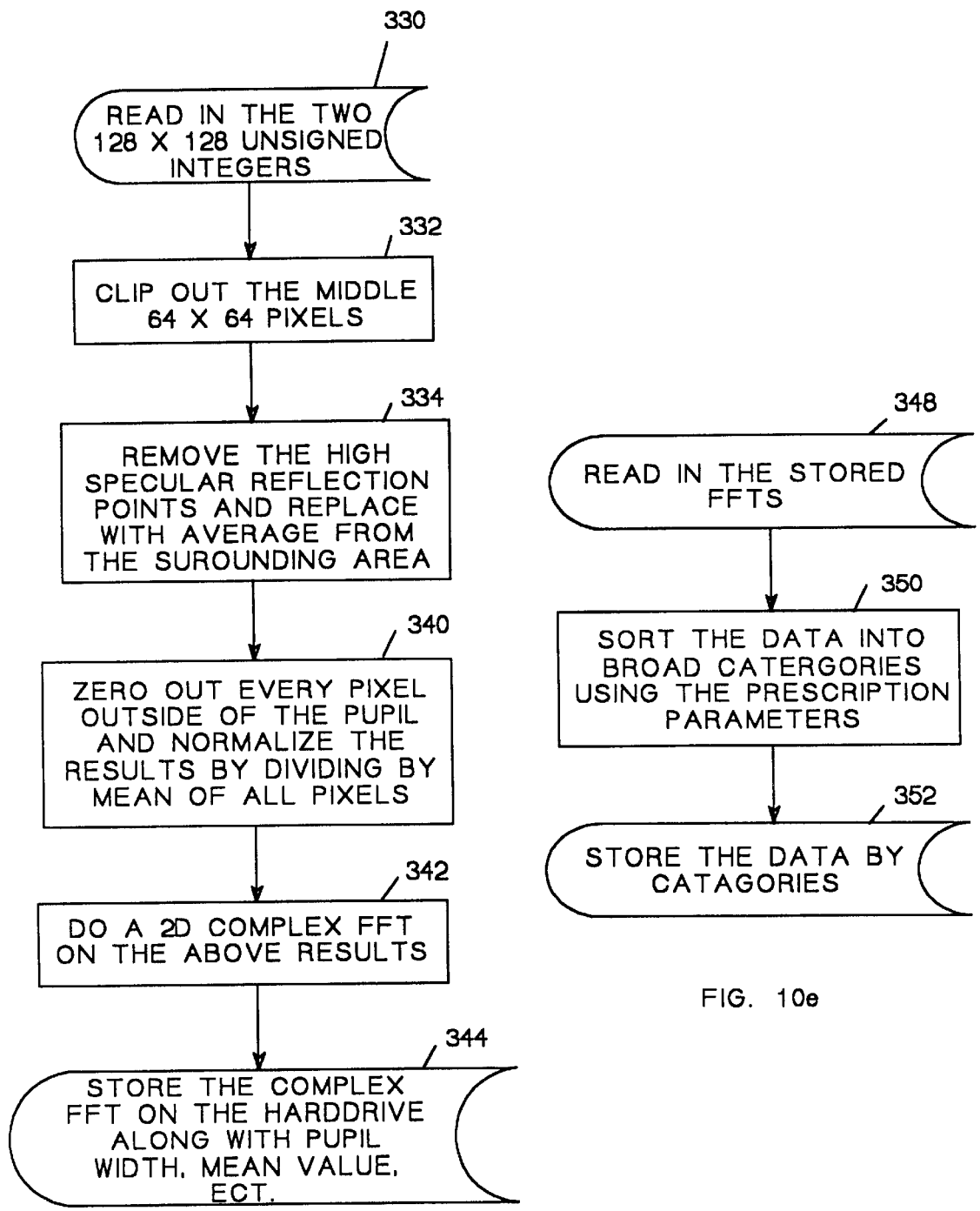
FIG. 10 is a flowchart showing another method for detecting disease conditions in the eyes.
Figure 10A:
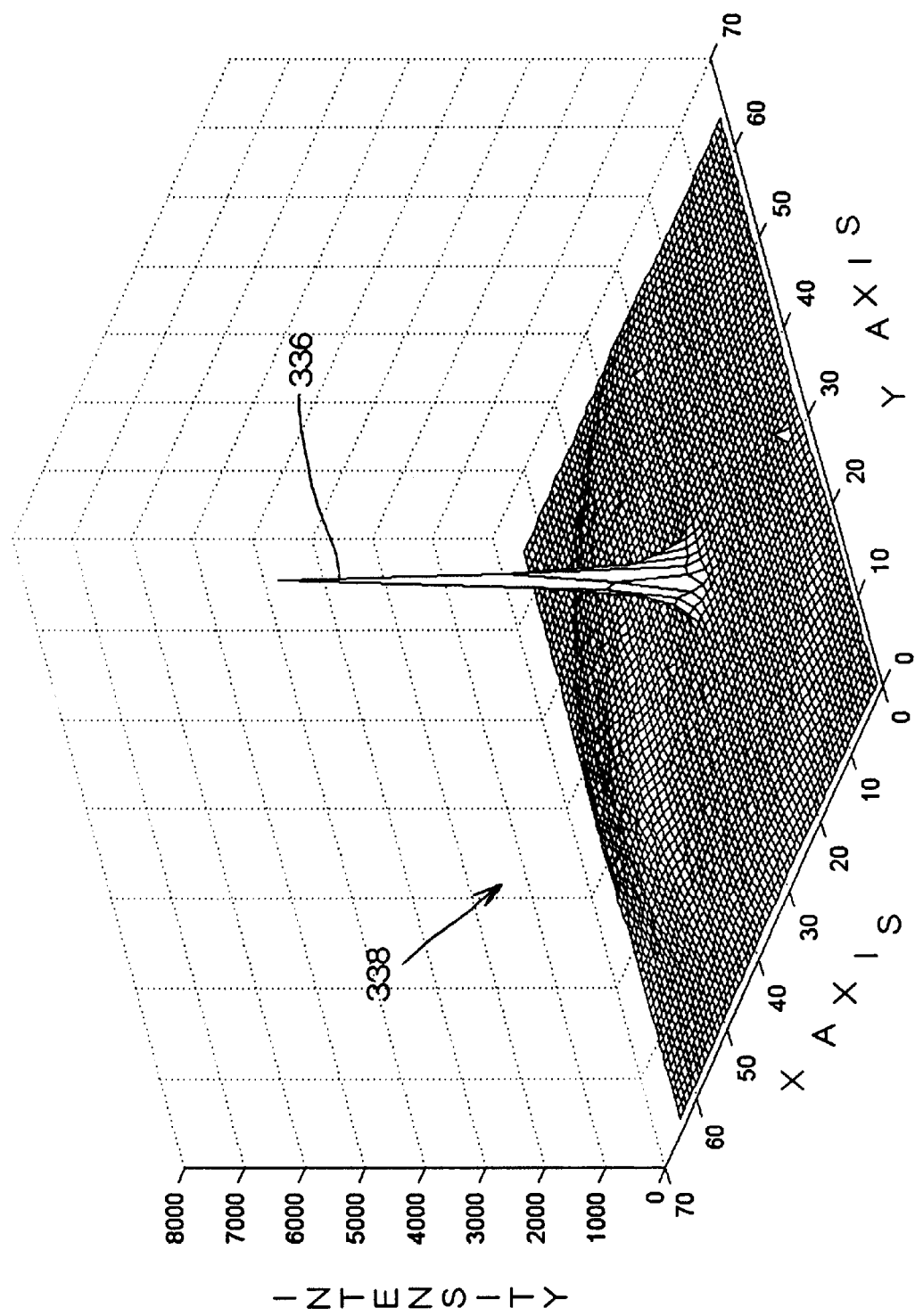
FIGS. 10a, 10b, 10c and 10d are graphical representations of particulars of the flowchart of FIG. 10.
Figure 10B:
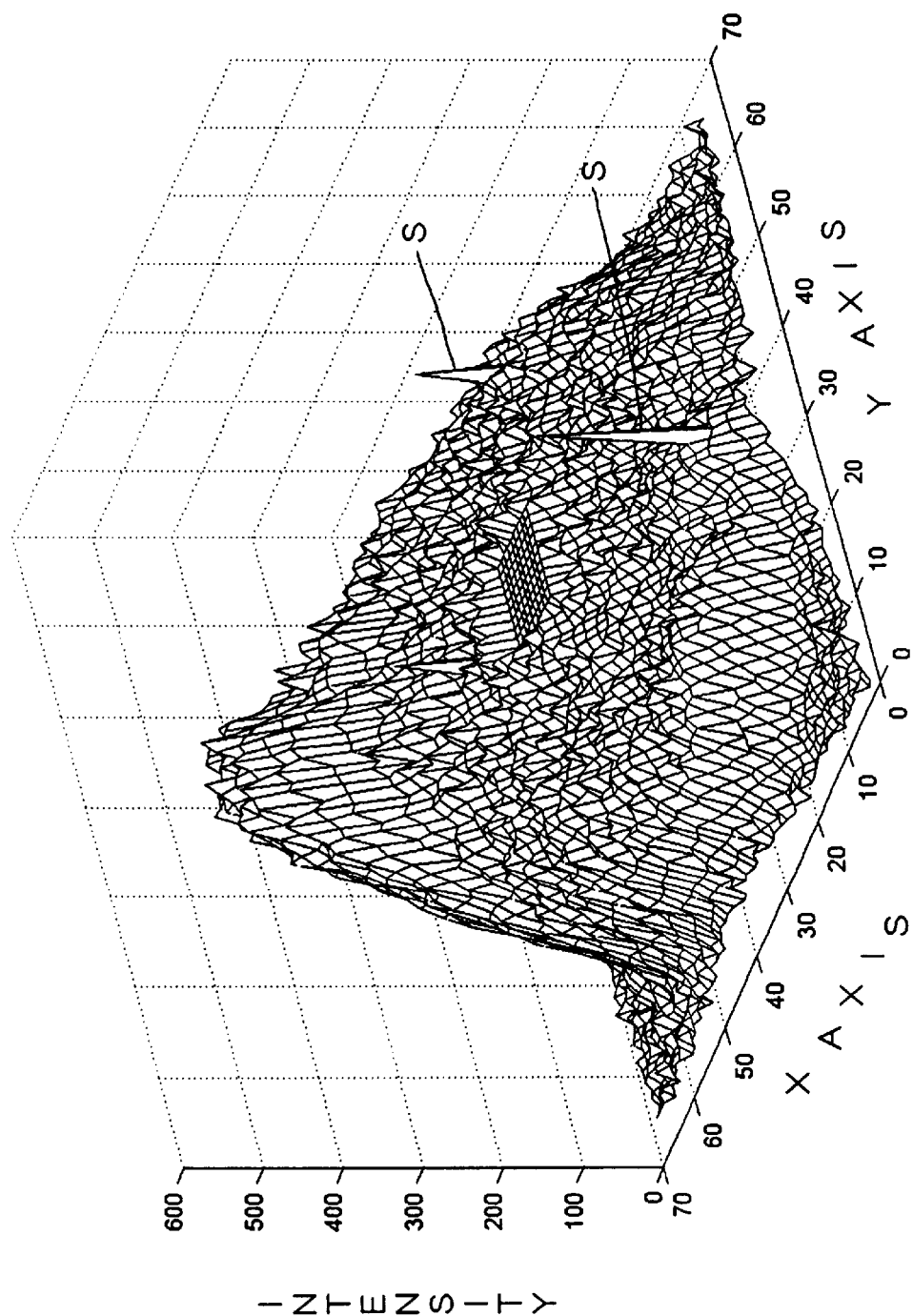
Figure 10C:
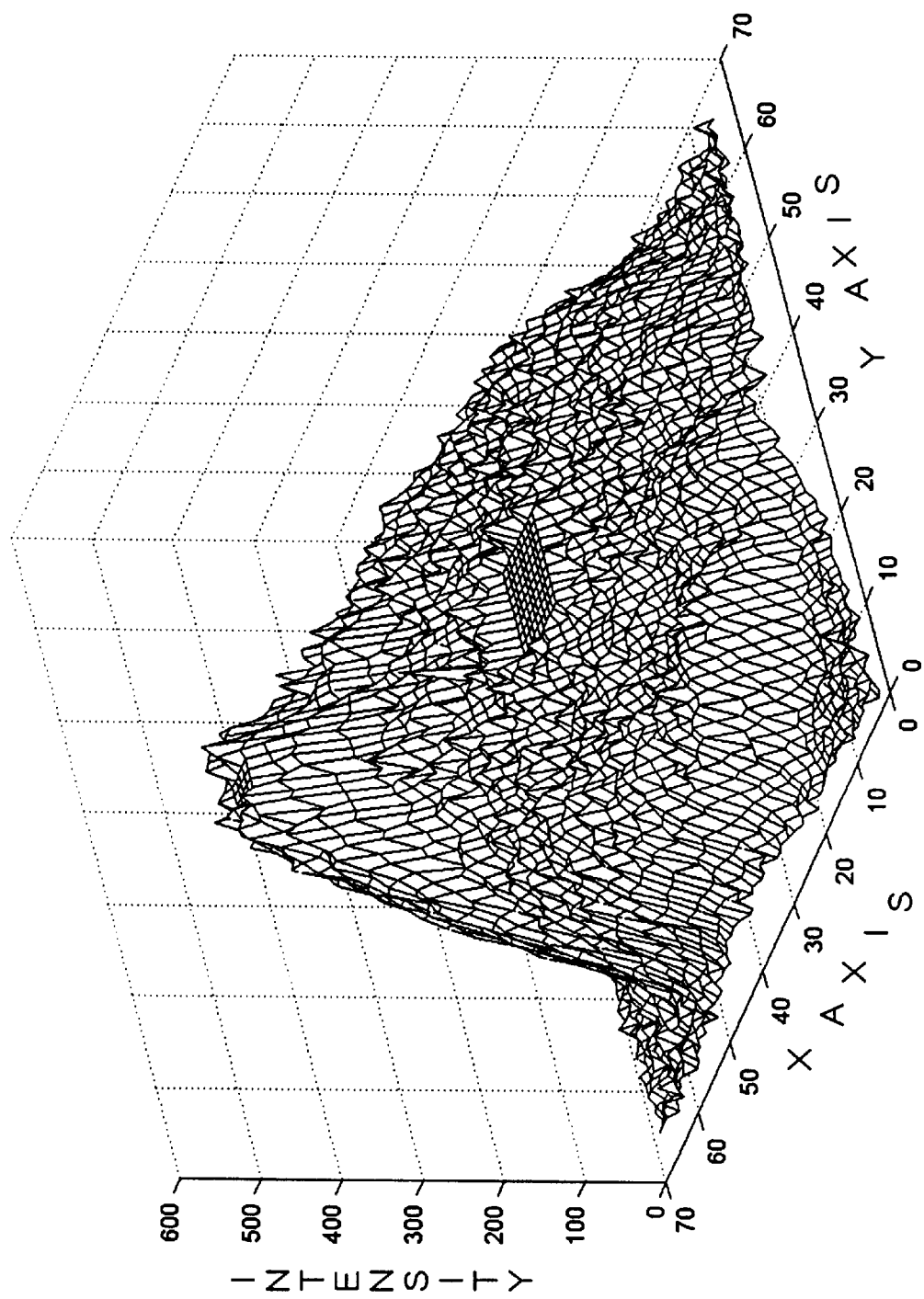
Figure 10D:
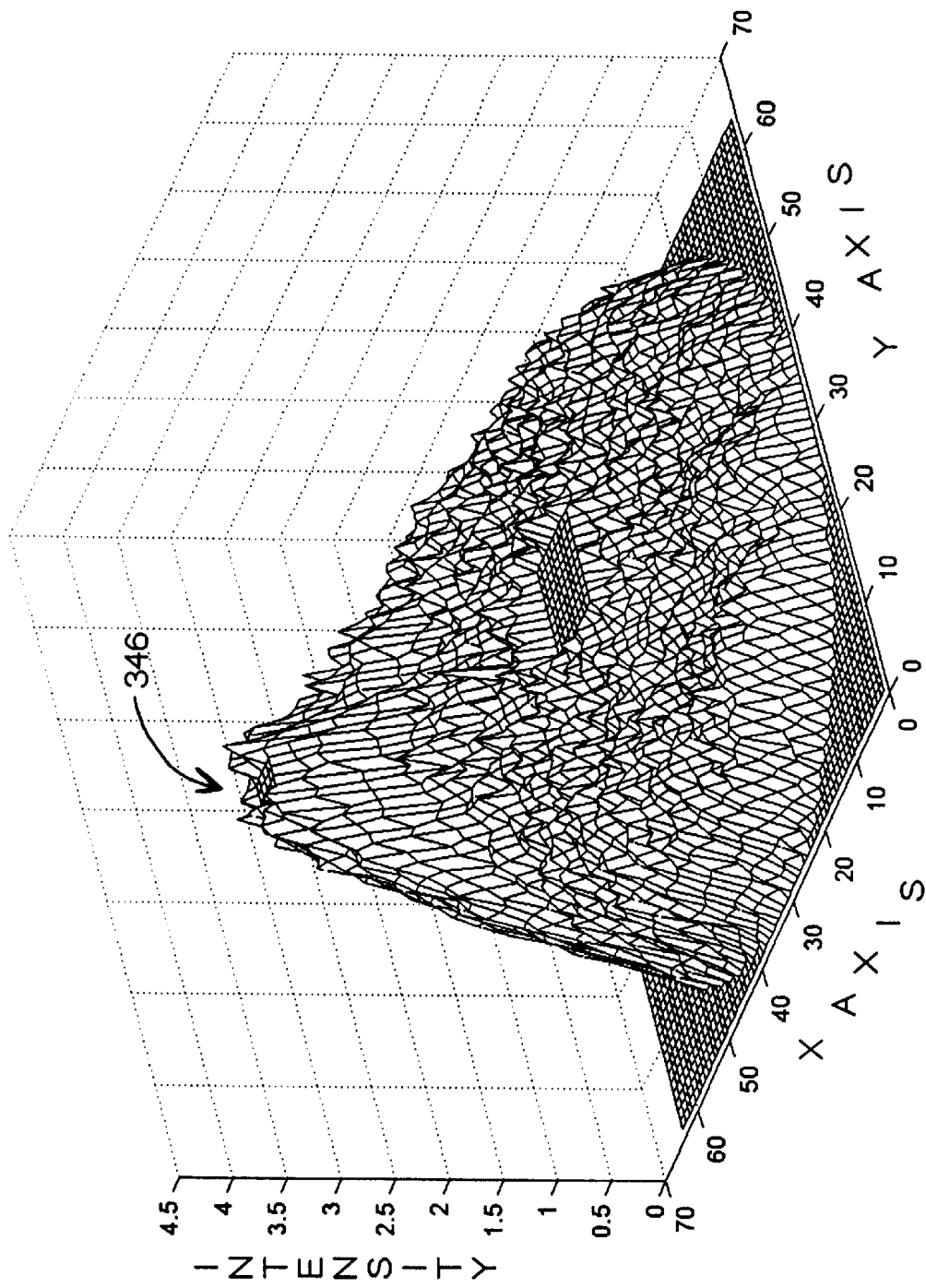

Another method for detecting disease conditions and processes in the transparent media of the eyes is shown in the flowchart of FIG. 10 and the accompanying drawings. In this or any of the other embodiments disclosed herein, the program may be configured so that an operator may simply position a box around one or both of the eyes with the iris and pupil generally centered within the each box, place crosshairs in the approximate center of the pupil, or superimpose a circle closely sized to that of the pupil over the circumference of the image of the pupil. Where the pupil is automatically located within a square array, such as a 128 by 128 pixel array cropped from a larger array as shown at box 330 of FIG. 10, at box 332 a smaller array, such as a 64 by 64 array, containing a portion of the iris and the pupil may be taken. FIG. 10a shows such a 3-dimensional plot of a 64 by 64 array plotted along X and Y axes, with light intensity plotted along the vertical axis. This smaller array may be obtained as described in any of the methods of the foregoing, such as the method disclosed in FIG. 2 at box 76 wherein a smaller array may be cropped and centered about an intensity spike that may be the corneal spike. The array of box 332 is read into computer memory, and at box 334 the high intensity spike is removed. This may be done by selecting the highest intensity pixel in spike 336 and cropping the spike at an intensity level lower by about 75 intensity increments or so than adjacent pixels in both X and Y planes. If desired, a patch may be interpolated across the cropped area as described above. As shown in FIG. 10a, the high intensity spike 336 about which the array is centered has a highest intensity of between 6000 and 7000, while the next lower area of the myopic or hyperopic area 338, which is manifested as a bulge in intensity values, has an intensity value of less than 600 or so. As shown in FIG. 10b, when the largest intensity spike is cropped and the intensity values scaled according to the highest intensity pixel, the highest intensity level of the array drops to about 600 or so, causing more topographic detail about the retinal reflex to become evident. If desired, the highest intensity cropping process of box 334 may be repeated, eliminating spurious spikes such as spikes S in the array of FIG. 10b that still may be present, these spikes being removed as shown in FIG. 10c. At box 340 a threshold may be established by selecting an intensity level slightly higher than the highest pixel in the iris, which may be about 50 or so, and setting all pixels having an intensity below this threshold to 0, as shown in FIG. 10d. After the thresholding process of box 340, the array may be normalized by dividing the value of each pixel in the 64 by 64 array by the average value of all pixels in the 64 by 64 array. At box 342 of FIG. 10 a 2-dimensional Fast Fourier transform is performed, which may be found in the referenced MATLAB program and associated tools. The result of the Fast Fourier transform is stored at box 344 in a particular category, these categories broadly arranged in categories such as hyperopia, myopia, stigmatism, strabismus, and occlusions such as cataracts. Each of these broad categories may further be broken down into subcatagories indicating degree of the refractive error or occlusion, such as myopia, 0–2 diopters, myopia, 2–4 diopters, myopia, 4–6 diopters, etc. The degree of refractive error of hyperopia and myopia may be ascertained by averaging or taking some other function of a selected number of the highest intensity pixel intensities of the myopic or hyperopic area 346 as shown in FIG. 10d. For stigmatism, rotation of the area indicating stigmatism in a 2-dimensional array may simply be measured. The degree of strabismus may be ascertained by comparing the areas of the white portions on both sides of the iris of one eye with corresponding areas of the white portions of the other eye, or by measuring the extent of shift of the corneal spike from the center of the pupil. The severity of cataracts may be ascertained by measuring size of the occluded area of the pupil. Due to the relative speed of the processes of FIG. 10, 60 categories or so would not present a significant delay in obtaining the results of a scan with commercially available PC-type computers of today.

At FIG. 10e the categorizing process is shown. Here, at box 348 the stored Fast Fourier transforms may be read into memory, and at box 350 each Fast Fourier transform may be sorted as described for myopia and hyperopia, and at box 352 the sorted data is stored.

Figure 11:
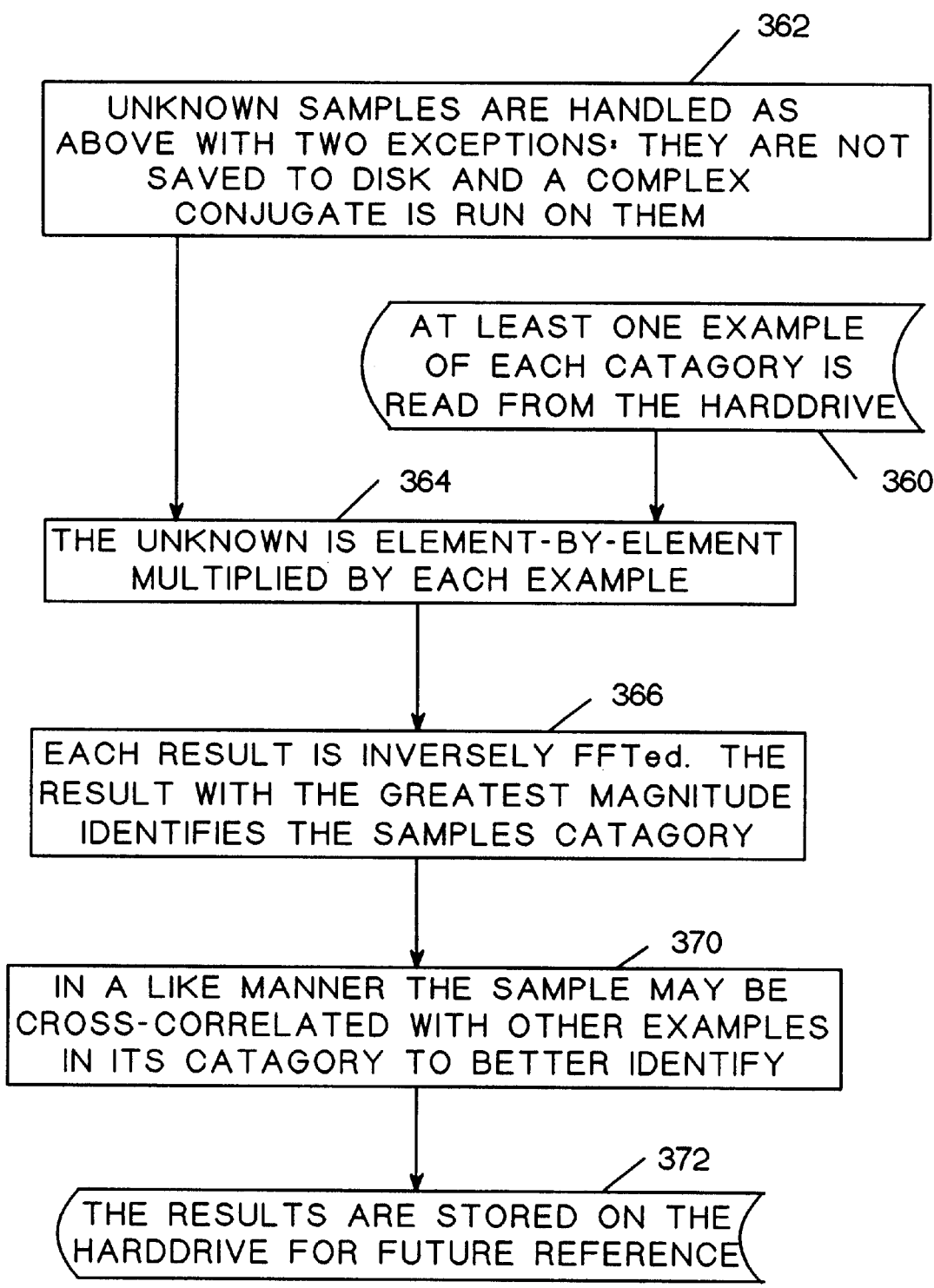
FIG. 11 is a flowchart of a correlation process for identifying disease processes of the eye.
Figure 11A:
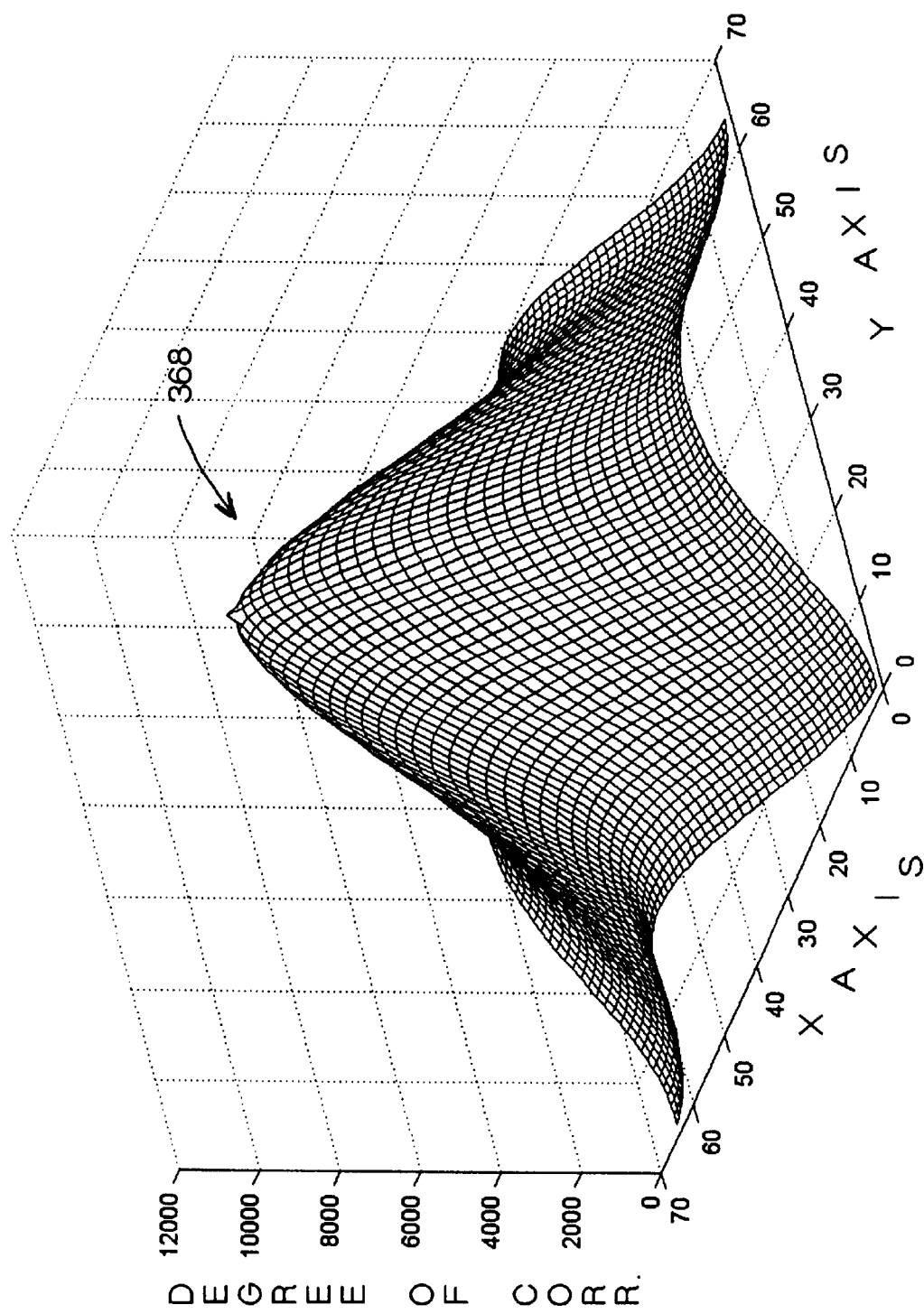
FIG. 11a is a graphical representation of a correlation peak.

In the flowchart of FIG. 11, identification of disease conditions in an unknown eye sample from a subject by means of a cross correlation is shown. At box 360 a sample from each category is read into computer memory. At box 362 the unknown eye sample is processed as described in the flowchart of FIG. 10 with the exceptions that the Fast Fourier transform data of the unknown eye sample is stored in computer memory and a complex conjugate process is applied to the Fast Fourier transform data of either the unknown eye sample or the samples from the various categories. This complex conjugate process simply reverses the sign on the imaginary portion of the data from the Fast Fourier transform. As the complex conjugate process needs to be done once if done on the unknown eye sample, it is computationally more feasible to perform this process on the unknown eye data rather than on each sample from all the categories. At box 364 the Fast Fourier transform data from the sample array and the complex conjugate-processed Fast Fourier transform data from the unknown eye sample is multiplied together pixel by pixel in the respective arrays, and at box 366 a cross correlation is performed by applying an inverse Fast Fourier transform to the result from each pixel multiplication of box 364. Those inverse Fast Fourier transforms having the highest magnitude identify the category into which the unknown eye data is placed. An example of the results of an autocorrelation of the data of FIG. 10d is shown in FIG. 11a, which shows a correlation array. Here, the resultant array from the inverse process of box 366 of FIG. 11 is shown plotted along the X and Y axes, with the degree of correlation plotted on the vertical axis. As would be expected in an autocorrelation, the maximum degree of correlation is illustrated by the large peak 368 in the center of the array indicating a high degree of correlation between the 2 identical arrays. Likewise, when a correlation occurs between the unknown eye data and a sample from one of the categories of abnormal eyes, spikes or peaks will appear in the correlation array where similarities exist between the category sample and the unknown eye data. At box 370 the unknown eye data may be cross correlated with samples of known refractive error or degree of occlusion in the particular broad category into which the unknown eye sample fits to determine a category of degree of refractive error or degree of occlusion for the unknown eye data. At box 372 the results of the cross correlations of box 370 are stored.

Figure 12:
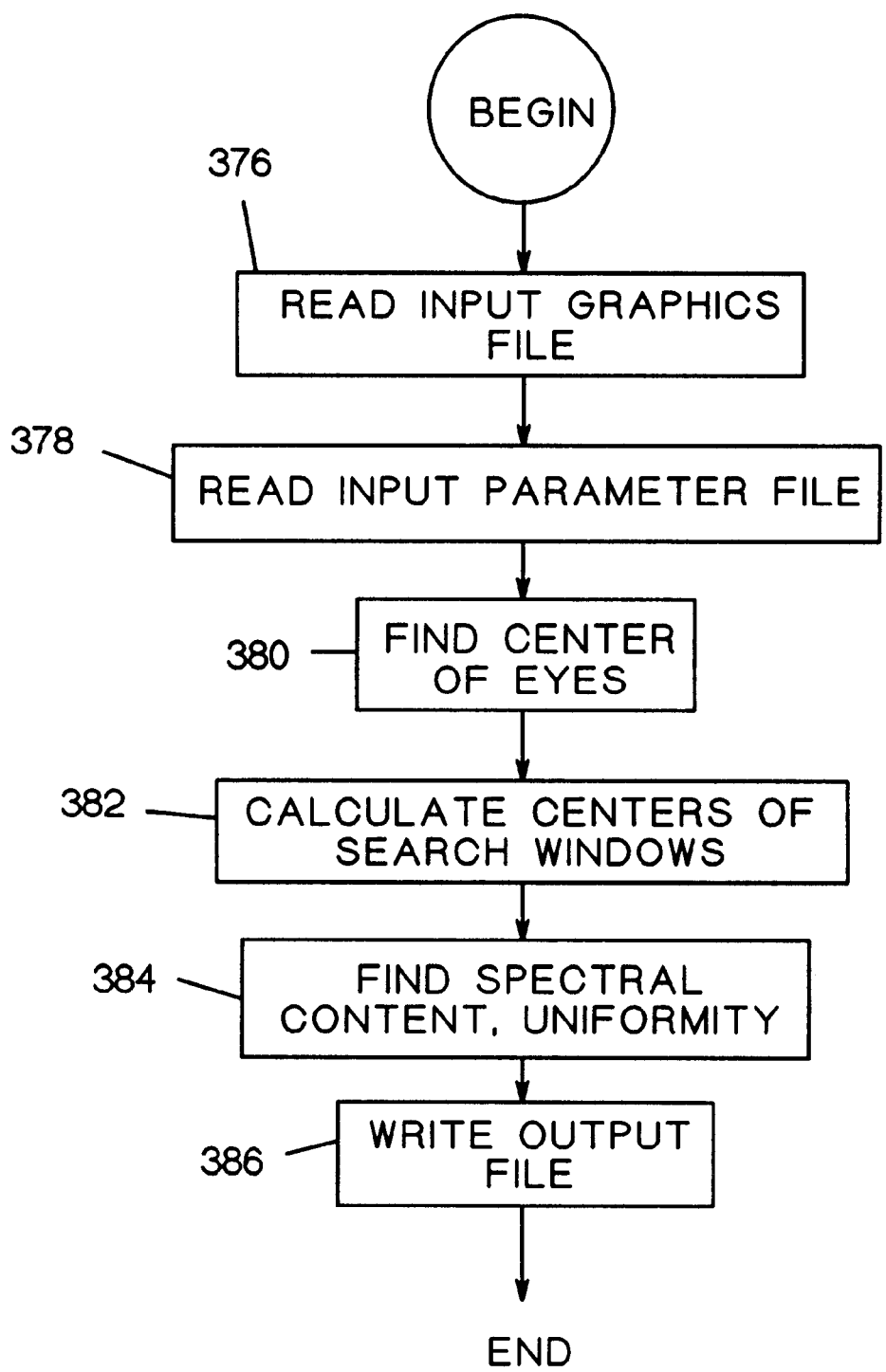
FIG. 12 is a flowchart of another method of the invention.

Referring now to FIG. 12, a high level flowchart of another embodiment of a method of the present invention is shown. At box 376, a binary graphics file is read, this file including information relating to intensity of the retinal reflex from the subject pupils. At box 378, labeled READ INPUT PARAMETER FILE, input parameters are read, these parameters setting the program configuration for finding a variety of characteristics of the eye and associating these characteristics with a number of abnormal or diseased conditions of the eyes. At box 380, labeled FIND CENTER OF EYES, the center points of the eyes are located by referencing the center of the corneal reflection. This reflection, as described in the referenced patent, is developed by a light source in the form of a strobed flash, and appears as a bright point in the center of each eye. The area encompassed by the pupil may be located by any of the earlier described methods or any other method that would be apparent to one skilled in the art and at box 382, labeled CALCULATE CENTERS OF SEARCH WINDOWS, approximately every third pixel n vertical and horizontal directions over the entire area of the retinal reflex is designated to be the center of a square search window of about 8 by 8 pixels, these search windows used to analyze spectral content of the retinal reflection. At box 384, labeled FIND SPECTRAL CONTENT, UNIFORMITY, an array of 8 pixels by 8 pixels is generally centered on each of the designated pixels of box 382 and an analysis is performed on the light intensity levels of the 64 pixels in each array. The results of this analysis provide an indication of one or more diseases or abnormal conditions of eyes of the subject. At box 386, labeled WRITE OUTPUT FILE, information, which may be in an ASCII format, relating to the coordinates of each 8 by 8 search window, various spectral information, and other parameters calculated by the software are written to a file.

Each of the boxes of FIG. 12 will now be discussed in greater detail. Initially, the binary file at box 376 imaging the retinal reflex from the subject pupils is taken from the CCD pixel array in the camera, which as stated may be 510 pixels high and 765 pixels long. Each pixel in the array is capable of providing 65,536 intensity levels, and each retinal reflection occupies an area having a radius of about 29 pixels, which corresponds to about 4 millimeters. Parameters read at box 378 include 2 or more thresholds, 5 spectral filter coefficients and a maximum energy level, which parameters will be discussed hereinafter.

Figure 12A:
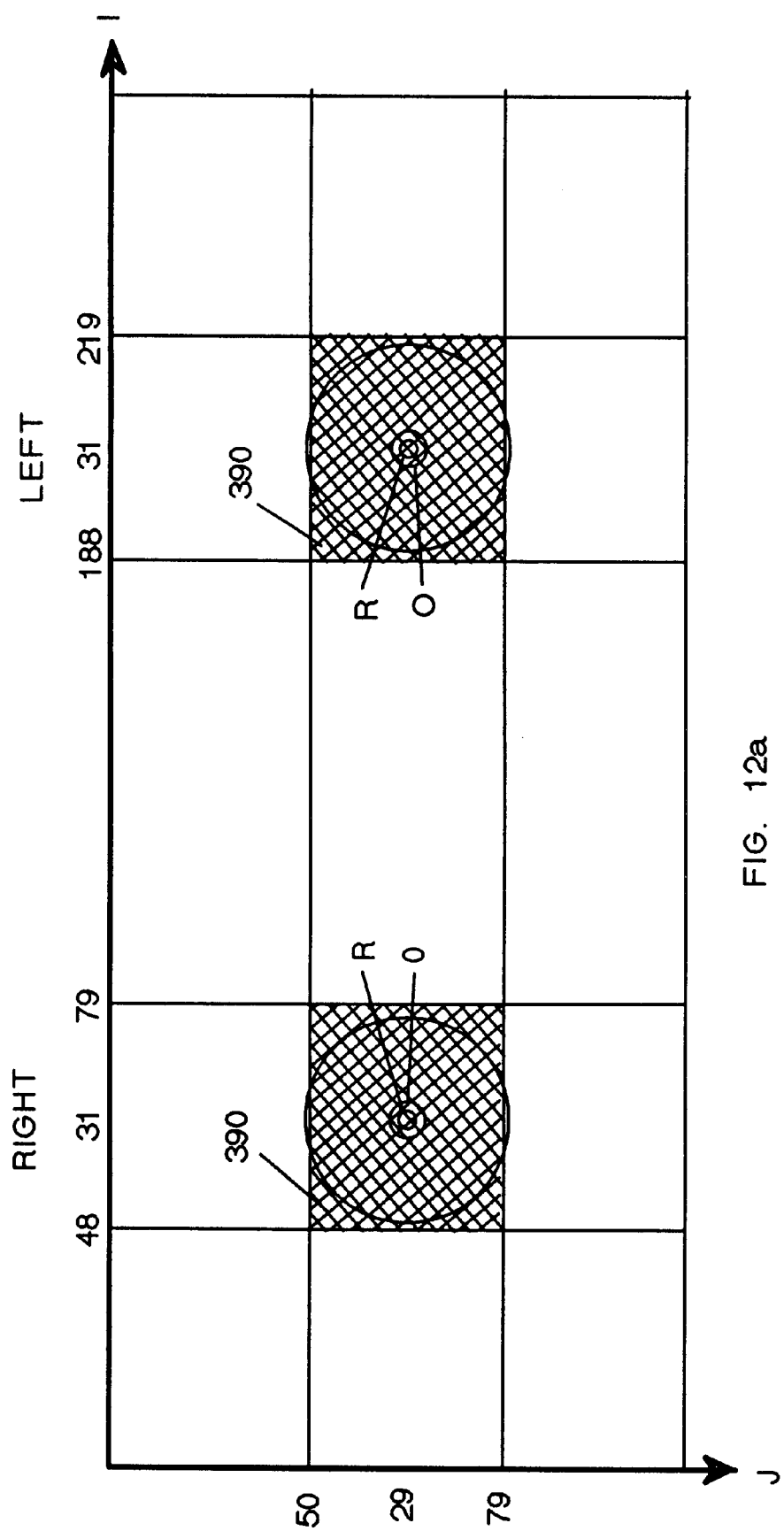
FIGS. 12a, 12b, 12c, 12d, 12e, 12f, 12g, 12h and 12i are graphical representations of particulars of the flowchart of FIG. 12.

With respect to finding the centers of the eyes, and referring to FIG. 12a, larger pixel arrays imaging eyes of the subject may be derived by any of the methods as described in the foregoing. The pupils of the eyes may be cropped from these larger arrays and stored as a smaller array, as by superimposing search domains 390 over the image of the subject eyes and then scanning pixels in the search domain for those pixels that register high intensity points of light that correspond to the corneal reflection. Search domains 390 may be manually placed over the pupils, as by use of a mouse or other pointing device or located automatically as described above. The smaller search 40 domains 390 may be about 29 pixels high and 31 pixels wide, which closely fits to the expected size of pupils of the subject. As such, the corneal reflection should be the brightest point in each search domain, as indicated by the corneal reflections R. The corneal reflection varies widely between subjects, and may occupy only a few pixels, such as 3 or 5, or as many as 200 or more.

Where it is desired to locate the center of the corneal reflection precisely, which may give a precise center of the pupil in the instance where strabismus is not present, and as the light intensity values of the corneal reflex are greatest in the center of the reflex, as shown by the smaller concentric circle in the center of each corneal reflection R, a first threshold provided by the input parameter file may be applied to the light intensity values of the reflex in each of search domains 390. This first threshold may be selected by scanning the entire search domain for the maximum light intensity values and setting the threshold value at a level just below the maximum intensity level. This threshold, when applied to the corneal reflection R, has the effect of blocking the less intense light levels thereof while passing the higher intensity levels of the corneal reflections. This also reduces the area within which the center of the pupil lies, which may be more precisely located by taking the geometric mean, or center of mass, of light intensity levels of those pixels that are above the threshold. This geometric mean of the pixels registering the highest light intensities of the corneal reflection is designated as the exact center of the pupil.

Figure 12B:
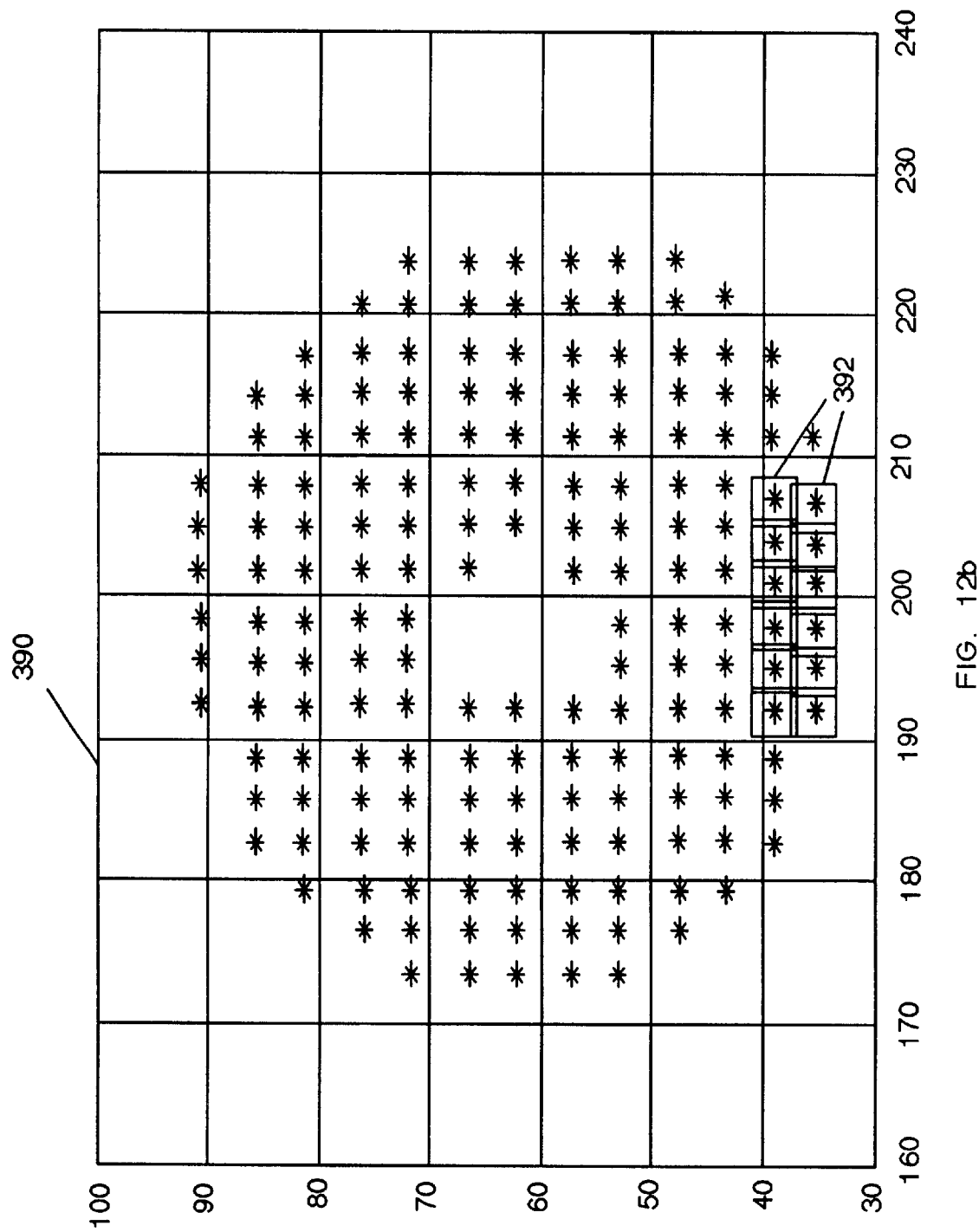
Figure 12C:
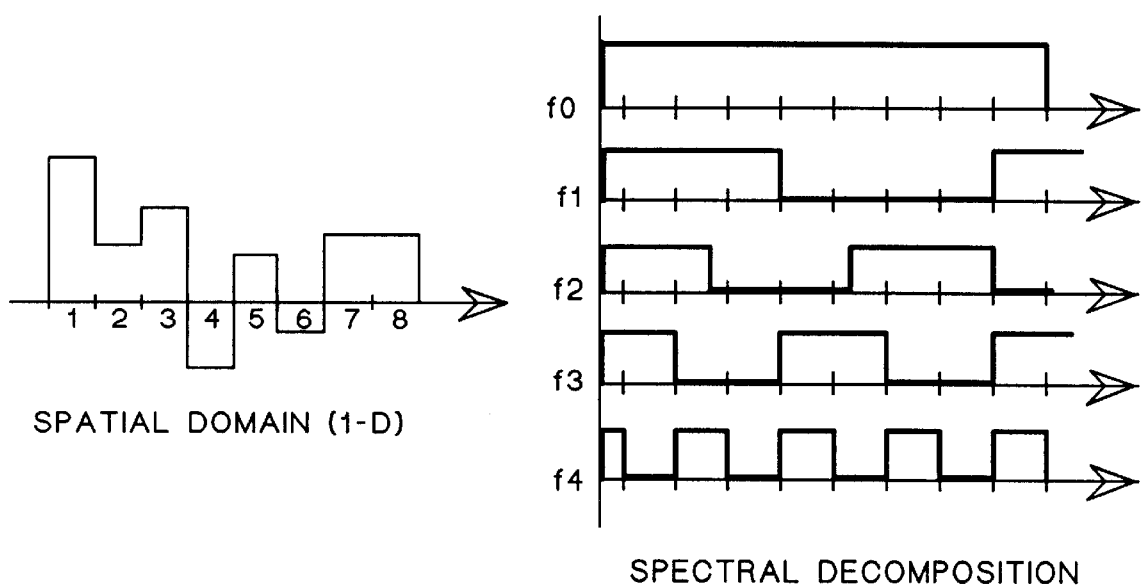

After each pupil is located in a respective search domain 390, and as shown in FIG. 12b, one of the search domains is selected for processing, and as described above, every 3rd pixel in horizontal and vertical directions in the search domain is designated as a pixel about which a small, 8 pixel by 8 pixel array 292 is generally centered. As such, there is an overlap of 2 or 3 pixels on each of the 4 sides of vertically adjacent and horizontally adjacent 8 by 8 arrays. This overlap provides, to some degree, an integrating function between the 8 by 8 arrays, resulting in a smoothing effect at interfacing points between each 8 pixel by 8 pixel array. Next, the light intensity values in each of the 8 by 8 arrays is recorded and processed to determine spectral content and uniformity of light intensity in each array. Here, and as stated, light intensity levels registered by each pixel are scaled so that each pixel essentially provides up to 65,536 shades of Grey, with 0 being the darkest possible light intensity, or light intensities having the least energy registerable by a pixel, and 65,535 being the brightest possible intensity, or a light intensity having the maximum possible energy registerable by a pixel. After the values for the 64 pixels in an 8 by 8 pixel array are recorded, the light intensity values for the 64 pixels therein are applied to a 2-dimensional Fourier transform algorithm to decompose the composite spectral energy of the rows and columns into 5 components, as shown for a single row of pixels in FIG. 12c. The 2-dimensional Fourier transformation provides information in both positive and negative frequencies, with the negative values being a duplication of the positive frequencies and therefore disregarded. Basically, after the 8 by 8 pixel image is passed through the 2-dimensional Fourier transform, the result is an 8 by 8 spectral array. In this spectral array, only the upper left 5 by 5 pixel array is used for further calculation, as shown by the spectral array of FIG. 12d. Processing of the 5 by 5 array is then undertaken, which involves taking the sum of each row and each column of the values in the 5 by 5 array. The sums of the rows of the 5 by 5 array are arranged in a sum column on the right side of each 5 by 5 array, and the sums of the columns are arranged in a sum row along the bottom of each 5 by 5 array, as shown in FIG. 12d. Discrete values in the sum row and sum column are then averaged by averaging the first, upper value in the sum column with the first, leftmost value in the sum row. The remaining values of the sum row and sum column are averaged, and the values derived from this algorithm applied to one or more spectral filters, an example of a highpass filter being shown in FIG. 12e. Some of these filters block some frequencies of the spectra and allow other frequencies thereof to pass, while other filters block/pass certain frequencies according to selected proportions, depending on the disorder being scanned for. Additionally, the properties of 2 or more filters may be combined to form a 3rd filter. These filter coefficients are read from the input parameter file described in the foregoing.

Figure 12E:
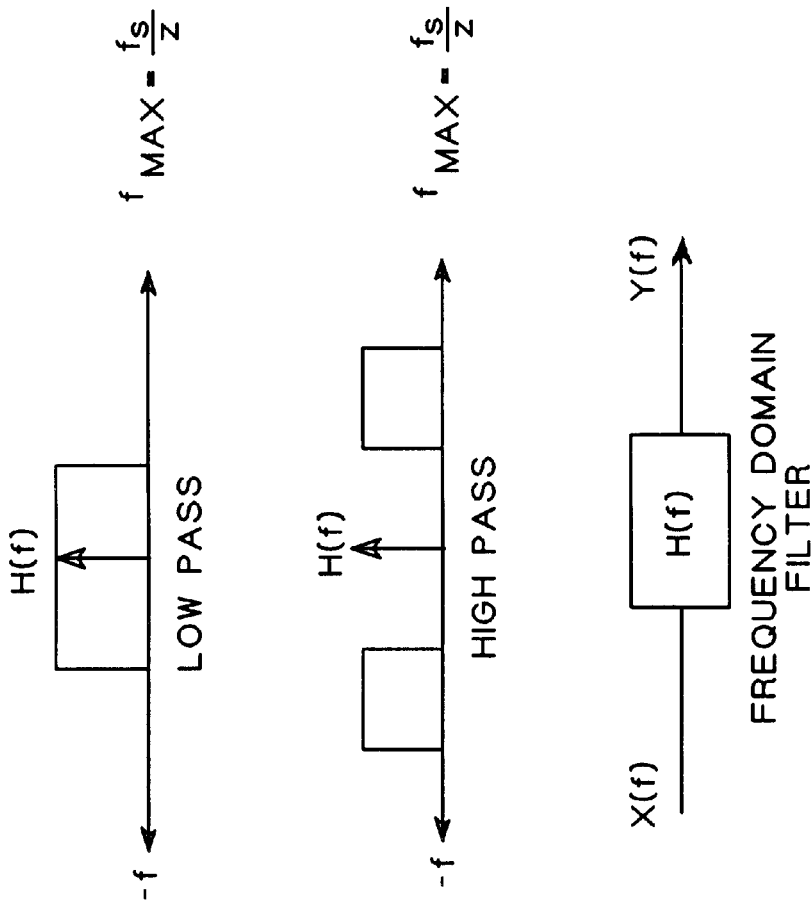
Figure 12D:
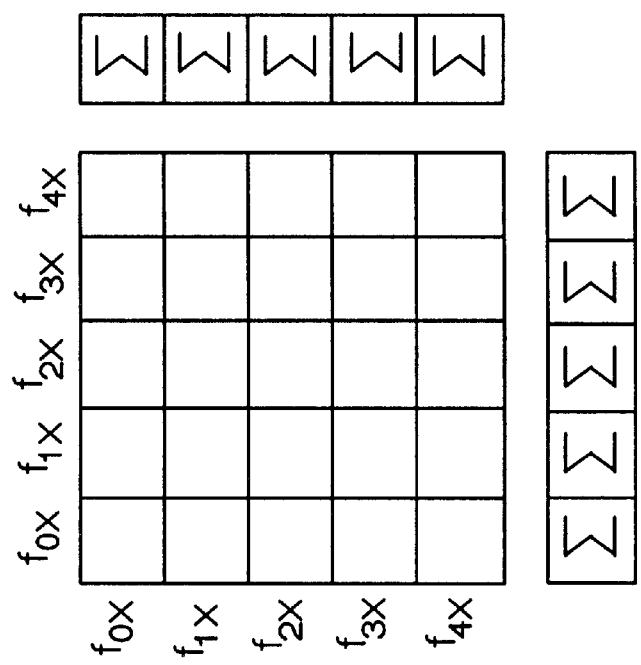
Figure 12F:
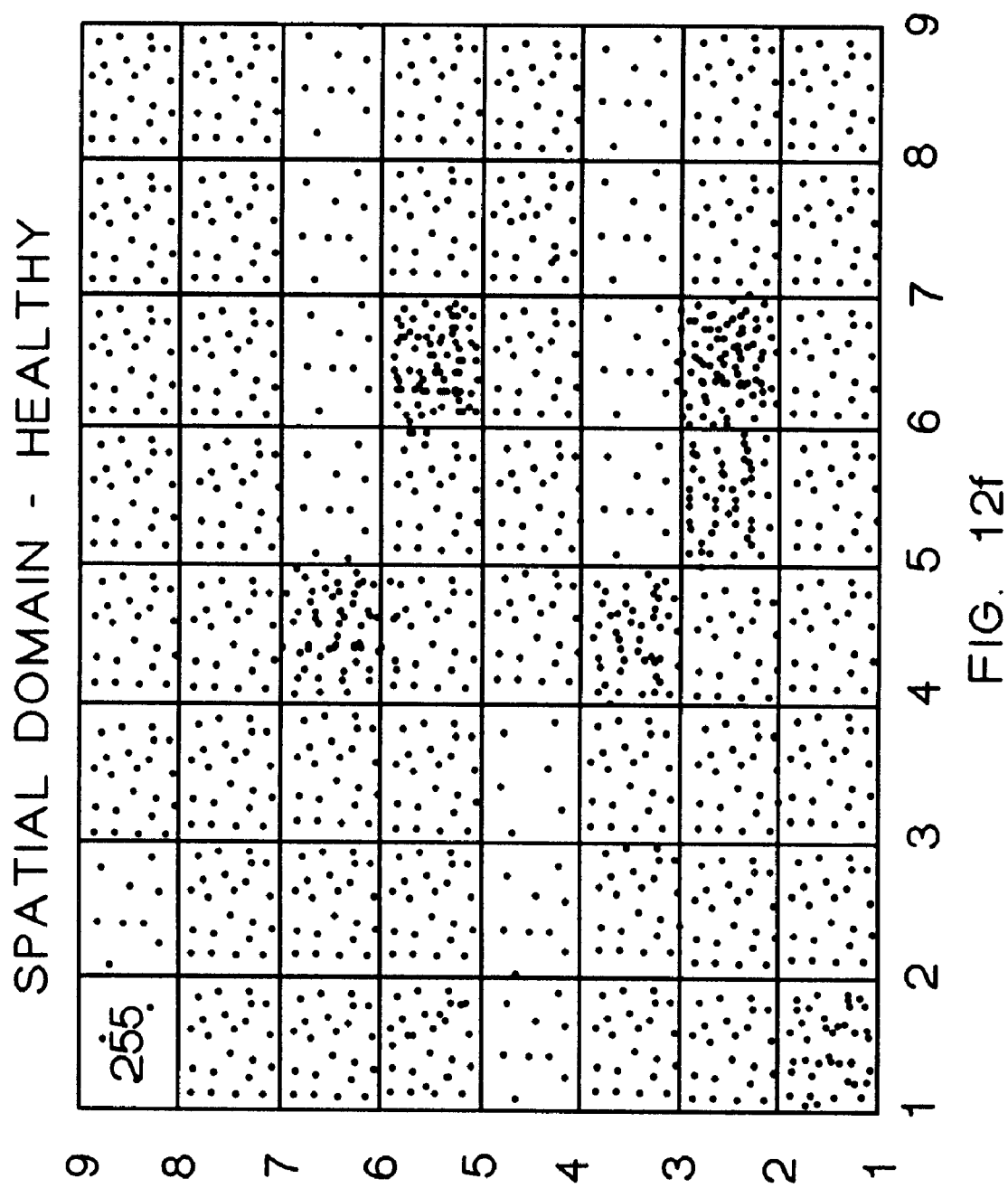
Figure 12G:
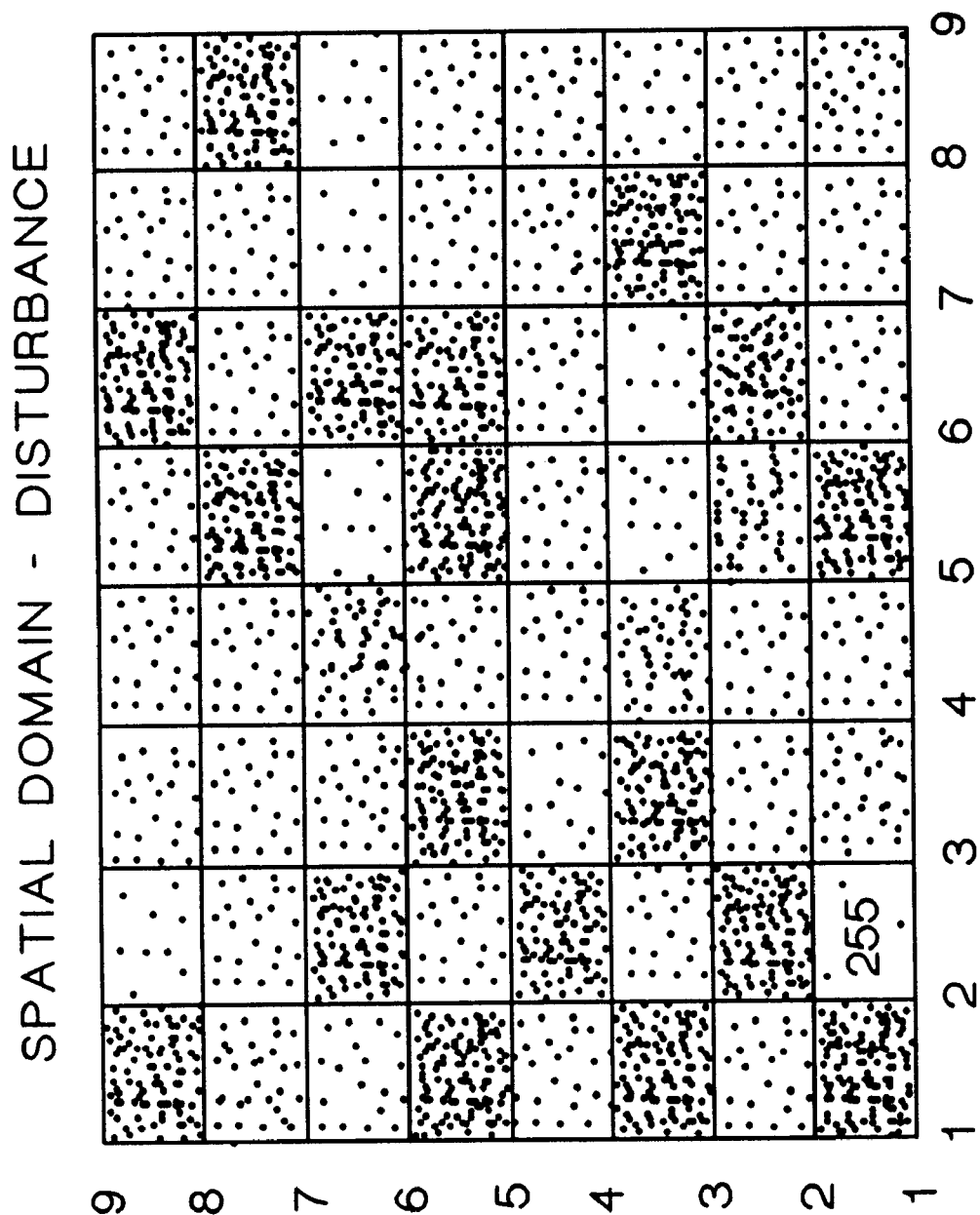
Figure 12H:
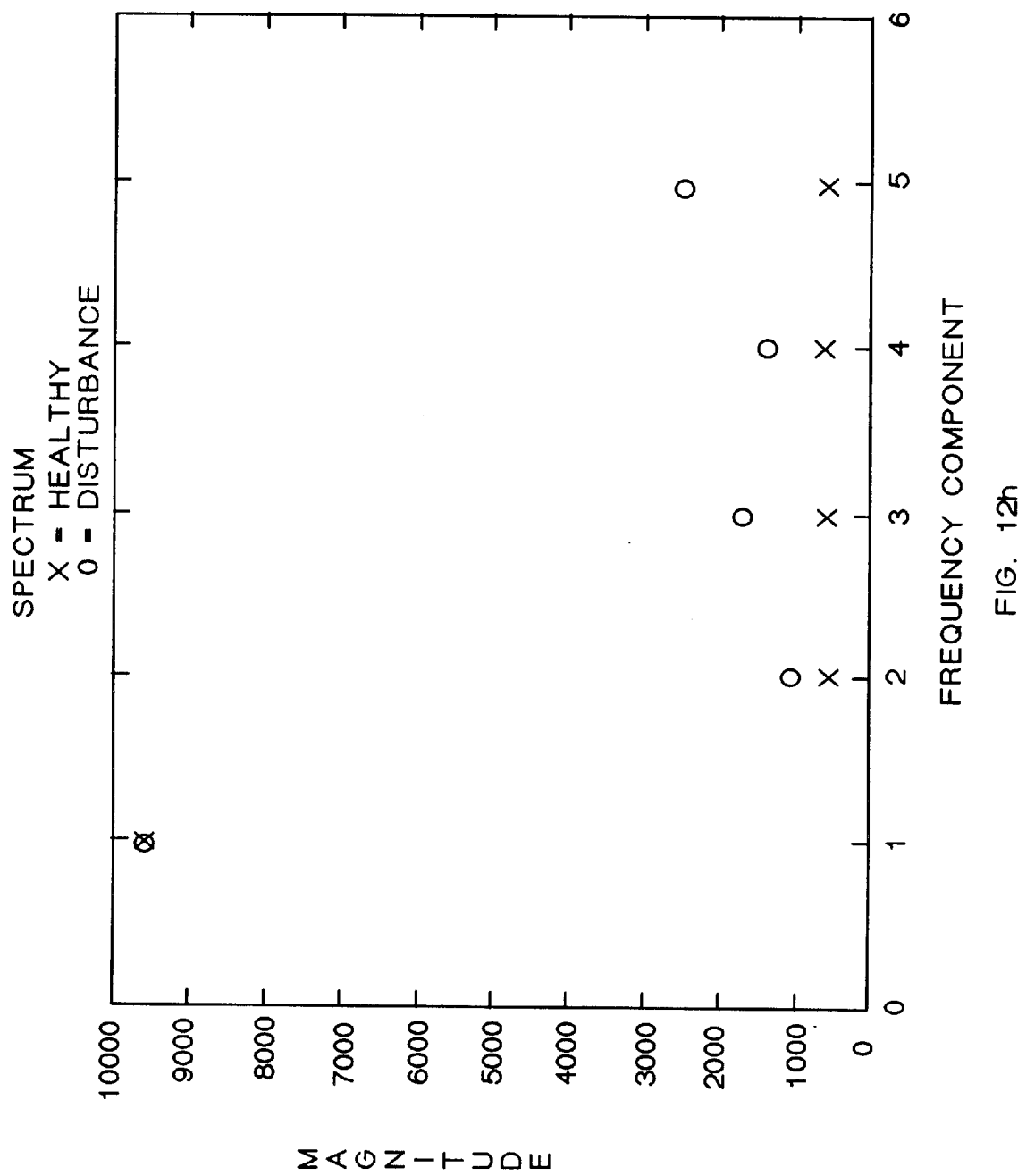

The particular highpass filter of FIG. 12e is configured to map the 1 dimensional data derived from the 5 element spectrum of FIG. 12h as a function, the particular function tailored to detect a particular disease or disorder of the eye. The highpass filter of FIG. 12e is configured to detect cataracts by virtue of the presence of more high frequency spatial information, or "turbulence", than a healthy eye would exhibit. An example of input data for a highpass filter would be 0,0,0,1,1. This would block the lowest three spectral components (f 0, f 1, f 2) entirely and allow the highest two components (f 3, f 4) to be summed into the energy level. To illustrate, the array of FIG. 12f is taken from a relatively normal eye, and shows a relative uniformity of shades of Grey. In contrast, FIG. 12g shows an array from an eye with a cataract, which has less uniformity and more higher frequency components of the spectrum than the normal eye. FIG. 12h shows the 1 dimensional spectra of the two sample arrays. Here, the higher frequency levels of the normal eyes are lower than the higher frequency levels in the eyes with turbulence.

Figure 12I:
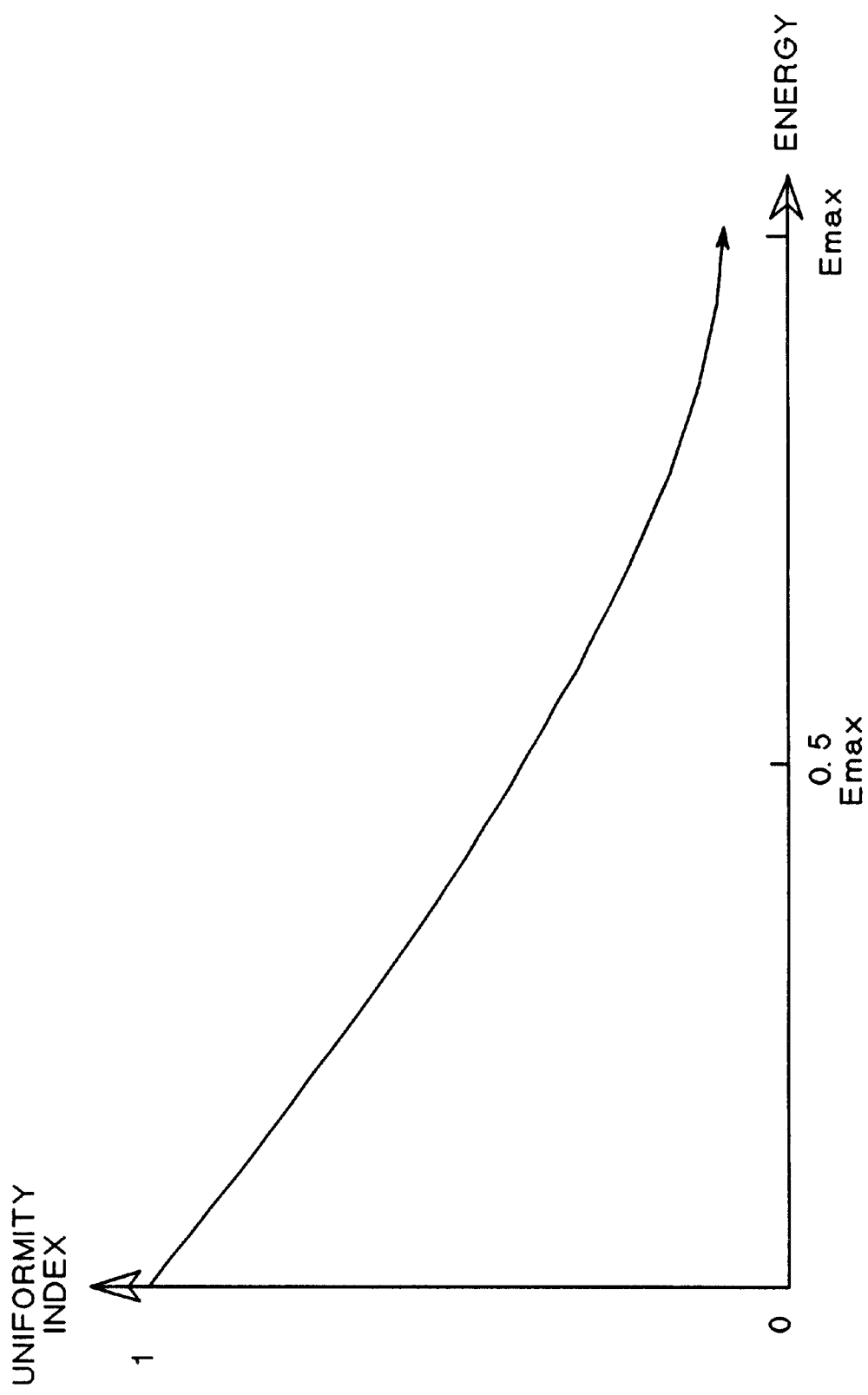

Next, the 5 spectral components from FIG. 12d are mapped into a single number indicative of uniformity, as shown in FIG. 12i. Here, uniformity of light intensities of the 8 by 8 array is plotted along the vertical axis, and energy in the spectral regions of interest is plotted along the horizontal axis. As such, from a uniformity of 1, the highest possible uniformity and the lowest energy, the possible numbers indicative of uniformity decay linearly to a point corresponding to about 50% of the highest energy parameter mentioned earlier, after which the uniformity numbers decay exponentially as energy increases. Thus, the higher the uniformity the more evenly light is reflected from the retina and passed through the transparent media of the eye. It has been found that a uniformity of 0.62 and less generally indicates a marginal eye, and a uniformity of 0.53 and below generally indicates a bad eye. Uniformities of greater than 0.62 indicate less granularity of the eye and corresponding better quality of the transparent media of the eye. These uniformity values of 0.62 and 0.53 may be used as thresholds in the input parameter file, but also may be changed depending on the disease condition being scanned for. For example, in a situation in which it is desired to minimize the probability of allowing a turbulent condition to be undetected, while increasing the probability of falsely indicating excessive turbulence in a normal eye, the operator would raise one of both of the thresholds. Also, to detect myopia or hyperopia, the first value in the filter (lowest frequency component) may be set to 1 and all other coefficients greater than 1 would be set to 0. This would result in a lowpass filter (12e) that may be applied where myopia or hyperopia causes higher intensities than average for a normal eye, these areas of higher intensities physically located approximately 30 pixels above the corneal spike for myopia and 30 pixels below for hyperopia.

While various embodiments are disclosed in the foregoing, and which are described in conjunction with a focal plane array of a particular size and type, it should be apparent that other types of focal plane arrays may be used with the algorithms described herein, as will be apparent to those skilled in the art. Also, image enhancement may include addition of artificial color wherein brighter portions of the reflection are depicted as white areas, with less intense graduations appearing as red, yellow, and green areas, respectively. Further, artificial topography may be applied to the images from the eyes to vertically plot the relative intensities of light issuing therefrom. In this instance, and in combination with the artificial color scheme, the brightest, white areas would extend to a highest level, with the white areas surrounded by lower red areas, in turn surrounded by lower yellow and green areas, respectively. Additionally, pattern recognition software may be employed to recognize signatures of normal eyes and the signatures of a number of commonly encountered problems of the eyes, such as nearsightedness, farsightedness, cataracts, etc.

In another embodiment of a method of finding and analyzing the eyes of a subject in an image obtained by a reflex photometer, a top-level overview of the functional flow and capabilities of a software package of the invention, hereinafter called FindEyes, is provided. The FindEyes program has been written in the Fortran computer language using the QuickWin (TM) capabilities of the Microsoft Fortran PowerStation 4.0 Developer Studio (TM), developed by Microsoft Corporation (TM), One Microsoft Way, Redmond, Wash. 98052-6399. Alternately, the FindEyes algorithms may be implemented in any one or more of several other packages or languages, such as Visual Basic, C or C++.

The principal objective of the FindEyes code is to provide a capability to process full face image data from the ST-7 digital CCD camera integrated into the reflex photometer as described in the referenced patent in order to identify location of each eye pupil and extract a portion of the pixel intensity data about each eye pupil. This extracted data can then be subjected to additional analyses to further identify and quantify features in the intensity pattern of light reflected from the surface of each eye as well as light reflected from features within each eye, including particularly the lens and the retina. These features or patterns can then be evaluated for correlation with various abnormal eye conditions and disease processes and possibly with abnormal conditions and diseases in other portions of the body, such as the kidneys. This process may be facilitated by use of spectral band, or color, filters and appropriate processing techniques to evaluate intensity values and ratios in different portions of the spectra which may be correlatable with chemical or other changes induced in the eye or tear film by abnormal conditions or disease processes within other organs of the body. The additional analyses may be performed on the same computer where the image data is initially collected from the digital camera. Alternatively, the entire full face image or the extracted eye data, along with other pertinent information, may be obtained at a treatment or screening location and transmitted to a centralized computer for additional analyses.

In the present implementation, the FindEyes code has been integrated with a patient clinical data collection system which has been implemented using the Microsoft Access 2.0 (TM) relational data base software package. Alternately, the subject clinical data collection system software might be implemented using any of several software packages and languages, as should be apparent to those skilled in the art. This clinical data collection system supports the collection of correlated clinical data and image data from the reflex photometer in order to develop a database to support the development and testing of image analysis and pattern recognition algorithms. The image analysis algorithms provide a capability to identify normal versus abnormal eyes and to correlate features extracted from the collected image data by image analysis with various vision abnormalities and disease conditions.

FindEyes also generates 2-dimensional bit-map images of the intensity patterns from each eye by assigning different colors to different intensity ranges and then setting the color of each pixel in the image according to its intensity value. FindEyes also generates 3-dimensional isometric view bit-map images of the intensity patterns reflected from each eye by generating a plot wherein, for each row of pixels, the intensity value for each row is plotted on a vertical scale and the pixel position is plotted on a horizontal scale. By shifting the vertical and horizontal offset of the baseline for each pixel row relative to the preceding row, and by drawing the rows from the backmost row to the frontmost row relative to the viewing position, the effect of a 3-dimensional image is created. Both the 2-dimensional and 3-dimensional bitmap images of the intensity patterns can then be imported into the database to support evaluation of the subject's eye conditions by trained observers as well as to support development, testing, and application of additional algorithms to extract and quantify features which can be correlated with clinical conditions of the eyes or other organs of the body. FindEyes also saves the extracted data file containing the pixel intensity data in a 128 by 128 pixel array centered on the pupil of each eye, along with other parameters, using unique filename specifications provided by the database code. The file may then be transmitted to a central site for additional analysis or saved locally for local analysis.

Since the reflex photometer of the instant invention can be used, among other things, to image individuals wearing corrective lenses (e.g., eyeglasses or contact lens) to determine if the lens are providing appropriate and balanced correction, a key challenge in the development of the FindEyes algorithms and code has been the development of algorithms which permit identification and discrimination of intensity peaks caused by eye pupils even in the presence of intensity peaks caused by reflections from glasses frames and lens, tear ducts, and other sources, including hot pixels, within the image. Many of the display features of the code have been developed in order to support the development and testing of such algorithms, and the implementation of algorithms which search for and test for the locations of eyes within the reflex photometer images while rejecting non-eye features accounts for a high percentage of the software code.

In this integrated system, the image data is first collected and stored by another software package, CCDOPS for Windows (TM) (distributed by Santa Barbara Instrument Group, 1482 East Valley Road, Suite 33, Santa Barbara, Calif. 93150), this software being executed under control of the Access (TM) database software. CCDOPS for Windows (TM) uses a unique filename specification generated by the Access (TM) database software to save the file containing the original ST-7 data so that the results from various image analysis techniques applied to the ST-7 image file can subsequently be correlated with the clinical conditions for the same patient at the time the image was taken. (CCDOPS for Windows (TM) also provides an optional capability to subtract pixel intensities from a "dark frame" exposure from pixel intensities from a "light frame" (normal) exposure. A "dark frame" exposure is made for the same duration as the "light frame" exposure but without opening the shutter, thereby obtaining the contribution to pixel intensity value resulting from "dark current" and other thermal noise effects.

After the image data has been collected and stored, the present version of the FindEyes code is launched from a "Find Eyes" push-button on the Image data collection form in Access (TM).

In a functional overview of this embodiment, execution flow for the FindEyes code is controlled by a main program routine which controls the sequencing of numerous other subroutines which implement the functions described below. Within the code, much of the data needed to control and coordinate the functions of the individual subroutines and collect the results is managed through a set of Fortran modules, although the code also uses argument lists to pass some of the data. Fortran variables are assigned to different modules according to the origin or purpose of the data represented by the different variables.

Data Modules

The modules and the types of variables assigned to them are summarized below, followed by a description of the logic flow.

Remote_Program_Control Module

A Remote_Program_Control module contains variables which are used to control (1) the overall flow of execution of FindEyes including the selection of various optional paths within the code, (2) input, output, and display options, (3) various boundaries and thresholds affecting the performance of individual algorithms supporting eye detection and discrimination, and (4) thresholds used to monitor calibration and performance of the reflex photometer instrument. Most of the variable values stored in this module are input from a RemControls.txt file.

Remote_Files_Management Module

A Remote_Files_Management module contains variables used to store the file path specifications and file names for several of the input and output files used by FindEyes. The file names stored in this module are input from a RemControls.txt file or via a command line which invokes execution of the FindEyes code.

Remote_ST7_Data Module

A Remote_ST7_Data module contains variables which store data from the ST-7 file header generated by the CCDOPS (TM) software package as well as the intensity value for each pixel in each row and column of the digital (CCD) camera. The header data includes parameters which may be used in subsequent image analysis such as exposure duration, whether a filter was used for the image, the height and width of the focal plane, and temperature of the CCD at image capture. Pixel intensity data is stored initially in a two-dimensional column major Fortran array and subsequently converted to a row major array for subsequent processing. This module also contains Fortran array variables which identify the location and original intensity values of any pixel data which would be modified by the conversion from the 16-bit unsigned integer data output by the CCD camera and the Fortran two-byte signed integer format used within the FindEyes program. The two-byte integer format is used to reduce hardware random access memory (RAM) required for efficient program execution. In the instant invention, the data stored in this module is input from the image file written by the CCDOPS (TM) software package. This image file contains the full image data (16 bit intensity values for 765 columns by 510 rows of pixels) read out from the ST-7 CCD camera. In another embodiment, the image data array may be downloaded from the ST-7 or other digital camera using Access (TM), Visual Basic, and commands in a software library furnished with the ST-7 camera. The image data array could then be passed as an argument between Access (TM) and the FindEyes code rather than having to read the image data to the FindEyes code.

Remote_Analysis_Support Module

A Remote_Analysis_Support module contains variables which store data used to support the processing and analyses performed by the FindEyes code. These data include Fortran logical arrays used to construct geometrical masks to permit rapid identification of pixels that are included in various calculations and algorithms for implementing tests for expected geometric shapes associated with the eye. Examples of such shapes include the pupillary aperture as well as the iris ring around the pupillary aperture. Other data stored in this module include coefficients for various edge detection filters used within the FindEyes code. This module also contains calibration constants used to convert pixel units to metric units, e.g., pixels per millimeter, and some internal run control parameters set within the FindEyes code to control subsequent processing. Except for internal run control parameters, other data within this module is input from the RemControls.txt file.

Remote_Analysis_Results Module

The Remote_Analysis_Results module contains variables that store results from processing and analysis of image data performed by FindEyes. This module contains results from an intensity histogram analysis, highest intensity pixels location analysis, radial minima analyses, eye location selection analyses, minima ring analyses, peak circle test analyses, pupil and iris edge detection analyses, pupil and iris average intensity calculations, and calibration and performance analysis data. This module also contains other intermediate and final results data from the eye search algorithms used to support evaluation of search algorithm performance and generation of optional graphical displays which, in turn, enable the detailed monitoring of algorithm performance for selected cases. This module also contains variables that store data extracted from the original full face image which can be used on the same computer, or transmitted to another "central" computer, for additional analyses such as to identify and quantify patterns in the intensity values which can be correlated with diseases or other abnormal conditions of the eyes and possibly abnormal condition and diseases of other organs of the body.

The intensity histogram analysis results include a Fortran array which contains, for the digital camera image being analyzed, the number of occurrences of pixel intensity values within adjacent ranges ("bins") of intensity values. Histogram analysis results also include the most probable pixel intensity value and the maximum and minimum intensity values for the image being analyzed.

The highest intensity pixels location analysis results include Fortran arrays containing the intensity values and pixel locations for a number, which may be 10, of the highest valued intensity peaks found within the search boundaries for the right and left eye, respectively. While 10 locations are used in this example, a greater or lessor number of such locations may also be used.

The radial minima analyses results include double-dimensioned Fortran arrays containing average intensity values (presently 9-pixel averages) determined to be the minima between a starting radius and an ending radius along each of several radial lines (presently 8) from the intensity peak being tested or from an updated estimate of the center coordinates for a candidate eye location. While 8 radial lines are used in the present example, more or fewer radial lines may be used.

The eye location selection analyses results include variables which store the results of weighted selection criteria that combine results of several tests to determine whether a given peak intensity location within an image is likely to be caused by an eye pupil. The results also include Fortran "real" values for the pixel coordinates within each image where the centers of the right eye pupil and left eye pupil were found using one of the eye location techniques used within FindEyes.

The minima ring analyses results include Fortran array variables which store results of the minima ring test, which is described in the Minima_Ring subroutine description below.

The peak circle test analyses results store results from the Peak_Circle_Test subroutine which is described below in the subroutine descriptions. Values stored in the Remote_Analysis_Results module from the peak circle test algorithm include, for points determined to be on the "circular edge," an average of the x and y coordinates of such points, which provides an estimate of the geometric center of the pupil of the eye, the average radius to the points from the estimated center location, the pupillary diameter determined from the average radius, the radial standard deviation of the points on the circular edge, and the peak circularity calculated as a ratio, to the total number of "edge pixels," of the number of pixels on the circular edge whose radius from the estimated geometric center is within a specified tolerance (typically 2 to 3 pixel widths) of the average radius. Other stored values from this analysis include intensity level at which the iterative circle test was initiated as well as the intensity level at which the best circularity and then smallest radial standard deviation was found for points determined to be on the "circular edge".

The pupil and iris edge detection analyses results include double-dimensioned Fortran variables which contain, for several candidate eye locations, such as 10 each for the right and left eye search regions, the maximum positive and, separately, the maximum negative, values from edge filters which are applied over selected radius ranges (nominally 20 to 70 pixel widths) along each of several radial lines, which may be 8 radial lines surrounding the estimated center location for the eye pupil. For an actual eye, the maximum slope transitions should correspond to image pixels within the pupil to iris transition region of the eye, and the minimum (most negative) filter values should correspond to pixels within the transition from the outer edge of the iris ring to intensity of light reflected from the sclera (white) portion of the eyeball.

The pupil and iris average intensity calculation results include the average intensity values for image pixels within the pupillary aperture based on the estimated pupil center and radius determined by the peak circle test algorithm and the average intensity value for pixels within the "iris ring" (a ring of pixels imaging the darker region of the eye surrounding the pupillary aperture). The "iris ring" is concentric with the pupillary aperture, with the inner and outer radii of the "iris ring" established as user controlled offsets set via the RemControls.txt file from the calculated pupillary radius. Another value, called DeltaSum, is also calculated based on the sum, for pixels within the pupillary aperture, of the differences of the intensity value for each pixel and the intensity value used as the starting intensity value (called CircleTestStartLevel) for peak circularity tests within the Peak_Circle_Test subroutine, described below.

The calibration and performance analyses results include the peak intensity found within the defined rectangular region of the image where the "calibration device" is imaged, the pixel coordinates of the pixel with the highest image, and an array containing the intensities of pixels within a region (nominally 10 pixels by 10 pixels) encompassing the image of the "calibration device."

The values stored to support the graphical displays associated with the eye search processing include Fortran arrays containing intensity values, or logarithms of intensity values, for sections of rows or columns from the full image. These arrays are used to generate small (typically up to 128 pixels in extent) intensity cross-section plots for portions of the full image which are superimposed upon the full image and are useful in examining certain features as well as for monitoring the performance of the eye detection algorithms. Other variable values are also stored to enable proper positioning of the superimposed image relative to points of interest on the full face image.

Data stored within the Remote_Analysis_Results module for possible transmission to a "central" site computer include Fortran arrays containing intensity values for regions of pixels (nominally 128 by 128 pixels) surrounding selected eye positions; pixel coordinates in the full face image of the centers of the eye pupils and coordinates of the upper left corners of regions extracted for further analyses; and the inter-pupillary distance (distance between centers of pupils of right and left eyes). Additional data stored in other portions of the Remote_Analysis_Results module, as well as other parts of FindEyes, may also be selected and included in transmitted data.

Remote_Graphics_Colors Module

The Remote_Graphics_Colors module contains Fortran array variables which store relative intensity levels and user selected color values which can be used in conjunction with a pixel intensity histogram generated by FindEyes to assign different display colors to image pixels of different intensity levels. This module also contains other variables which support alternative methods of assigning display colors to different image pixels. The data stored in this module is input from the RemControls.txt file.

Logic Flow

The preceding section has described the principal data elements which are either input into FindEyes or generated by the FindEyes software. The following section will describe the overall logic flow for the software as implemented in the main program, FindEyes, as well as the more detailed logic implemented in the principal subroutines.

FindEyes Main Program

Figure 13:
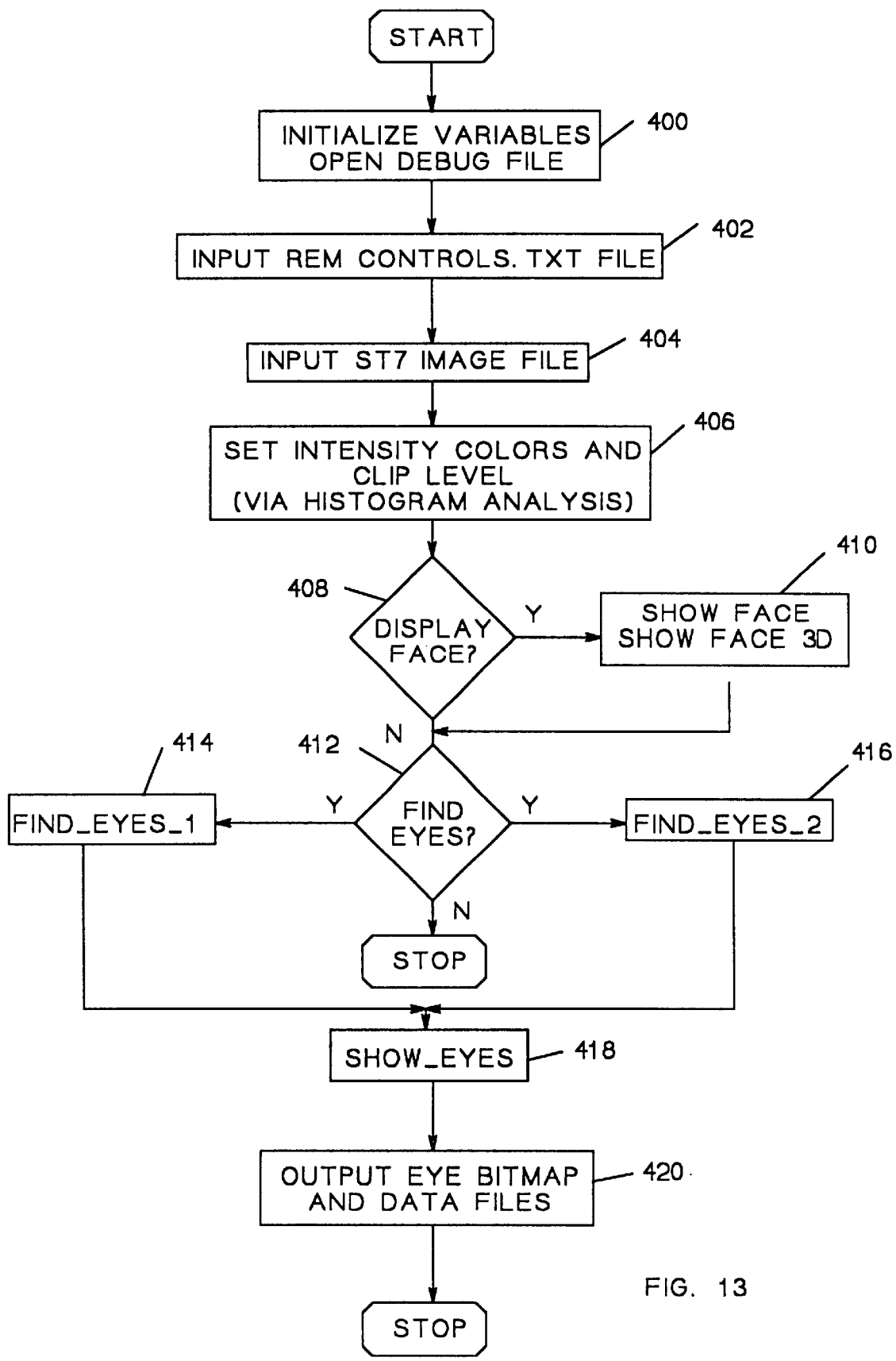
FIG. 13 is a flowchart of another embodiment of a method for identifying and locating eyes of a subject.

The top level flow of the FindEyes main program is described below and illustrated in FIG. 13.

After initializing the values of several Fortran variables, and opening a file to collect debug and code diagnostic data at box 400, FindEyes calls another subroutine, Remote_Setup, which opens and reads in the RemControls.txt file at box 402. The data from the RemControls.txt file is stored in the Remote_Program_Control, Remote_Files_ Management, Remote_Analysis_Support, and Remote_ Graphics_Colors modules as described earlier. This file contains user editable Fortran namelist variable value assignments which control the execution of FindEyes, which includes overall program flow, output options, and details of execution of specific analysis algorithms. The code also accepts command line inputs, e.g., for the filename to be analyzed.

FindEyes then calls another subroutine at box 404, Read_ ST7, to read in the data file containing the ST-7 file header and pixel intensity (image) data from the reflex photometer. Data from this input is stored in the Remote_ST7_Data module as described earlier.

Next, FindEyes calls the Set_Color_Intensities subroutine at box 406 which generates a distribution of the number of pixels having intensities within predetermined intensity ranges, or "bins", and then uses this data to help assign color values to different intensity ranges to aid in visualization of the intensity patterns in the images captured using the reflex photometer of the instant invention. This intensity distribution data is stored in a Fortran array variable, Histogram, in the Remote Analysis_Results module described earlier.

An option in the software also generates an on-screen histogram of the intensity distribution showing, on the horizontal axis, the increasing intensity values for the different "bins", and on the vertical axis, the number of pixels having an intensity value which falls within the range of any specific "bin." In this histogram plot of the intensity distribution, the intensity range of the intensity "bin" having the highest number of pixels is referred to as the most probable intensity value for the overall image. The most probable intensity value for the histogram corresponds in general to an "average" intensity value for most of the image excluding peak intensity values and has been found useful as a reference intensity level for the assignment of color values to accentuate display of intensity patterns found in the retina reflex images created with the instant invention. As described later in this section, the most probable value from the intensity histogram, as well as the maximum intensity value, are also used to set certain thresholds which are in turn used in searching the image data to find the possible locations of eyes within the image data and in discriminating image features caused by eyes, and particularly eye pupils, from other features in the image.

Using the "most probable value" from the intensity distribution as the reference level for intensity color assignments tends to account for overall intensity variations between images on the same or different instruments which may arise from variations in flash output, variations in digital camera sensitivity, or other sources so that the color-coded bit map 2-dimensional and 3-dimensional images generated by the FindEyes program have a similar appearance for similar eye conditions. An alternative colorization technique is to assign colors using as a reference level an offset from the peak or average value of the intensity of light reflected from the "calibration device" within the stabilizer bar as described hereinabove. As stated, the "calibration device" in the present implementation may be a small ruby sphere placed within the field of view of the digital camera (and preferably in approximately the same plane as the face of the person being imaged—e.g., on the stabilizer bar facing the camera) so that light backscattered from the sphere is included in each image, thereby providing in each image a region of constant reflectance which provides a reference intensity level which may be used in image processing when necessary.

After the color values to be assigned to different intensity levels have been determined by Set_Color_Intensities, additional options, as indicated at inquiry box 408, within FindEyes permit the display of the full image captured by the ST-7 camera within the reflex photometer of the instant invention (which in the present implementation includes most of the face) in a 2-dimensional, face-on view (via a call to a ShowFace subroutine) or 3-dimensional (isometric) views with different viewing perspectives (via calls to a "Show3Dface" subroutine) at box 410.

In both views, colors may be assigned to different intensity levels as described earlier so that the intensity patterns in the image are accentuated in the displays. Both the 2-dimensional and 3-dimensional views have been found useful in developing and evaluating algorithms for finding the eyes in the overall image as well as for developing algorithms to extract and quantify features which can be correlated with clinical conditions of the eyes, and possibly with clinical condition of other parts of the body as noted earlier.

FindEyes then optionally (based on parameters set in the RemControls.txt input file) calls a set of subroutines at box 412 to find the eyes within the image from the reflex photometer of the instant invention using one of two basic approaches. The approach to be used is selected based on user input via a control variable within the RemControls.txt file. One approach, controlled via the Find_Eyes_1 subroutine at box 414, which is described in greater detail hereinafter, first scans user-defined rectangular search regions within the right and left halves of the full ST-7 image to identify up to some number, which may be 10, of the highest relative intensity peaks that may be a corneal spike within each search region. Find_Eyes_1 then applies various tests to each peak to help determine which peak is most likely to be a corneal spike associated with pupillary reflex. Test results may then be combined in a decision matrix with appropriate weighting criteria, determined heuristically and experimentally, and the candidate peak most likely to be an eye may then be selected. The pixel coordinates of the updated center estimate of the pupillary aperture of the selected peak are saved and used for saving the pixel regions about each eye to be used for additional analyses.

Another approach, controlled via the Find_Eyes_2 subroutine at box 416, invokes a search approach which attempts to locate each eye based on a single pass approach which searches user defined search boundaries (rectangular boxes within the overall image) as above but applies various screening criteria and tests to each peak as it is encountered to determine if it should be accepted or rejected as an eye. For intensity peaks which pass certain screening criteria, multiple tests can be applied in a given sequence to accumulate confidence that a given intensity peak actually represents the location of a true eye (as opposed to intensity peaks caused by other effects as discussed earlier) before the search logic accepts the peak region as being the location of the eye for that search boundary and moves on to the other search boundary to search for the other eye (or exits the search logic if both "eyes" have been found). The tests which can be applied include any of those described within this specification, as well as others, such as a Hough transform, one example being discussed herein. The results of each test may either add to or subtract from the overall confidence and subsequent acceptance or rejection of the peak as a candidate eye location. Once the results of multiple tests have achieved a threshold level of confidence, the location of the peak, specifically the location of the estimated center of the pupillary aperture, is accepted as being the location of the eye for that search boundary and the logic moves on to find the other eye or to the next task.

Optional display capabilities integrated into the search algorithms outlined above permit the user to observe the progress and performance of the alternative screening techniques and the tests which are applied to help determine whether a given intensity peak is likely to be caused by an eye pupil, as shown at box 418. For example, the display capabilities include displaying a box about each of the candidate intensity peaks and then displaying, as by changing display pixel colors, the pixels selected for the minima ring tests or the peak circularity tests. Optional display capabilities include showing plots of the intensity (or the logarithms of the intensities) of a portion, presently 128 pixels centered about the pixel of interest, of the row and column of pixels which intersect at the "peak intensity pixel" being evaluated. Optional display features also show which pixels were considered and rejected by the intensity peak screening logic used in searching for the eyes.

After the right and left eyes have been found by one of the techniques described above, the pixel intensity values for a region of pixels around each estimated center of the eye pupil, presently 128 by 128 pixels centered about the center pixel for each eye, are saved in Fortran arrays (one for each eye) for subsequent analysis. In addition, the pixel coordinates of the estimated eye pupil centers resulting from the eye searches outlined above are used, together with a geometric calibration factor (mm/pixel), to calculate an interpupillary distance (distance between the center of each eye pupil). (The geometric calibration factor is determined experimentally for each instrument (e.g., by imaging a ruler) and input to the FindEyes program via the RemControls.txt file.)

After finding the eyes, FindEyes also optionally generates (and saves to bitmap formatted files at box 420) color-coded 2-dimensional and 3-dimensional bitmap images of the selected regions about each eye pupil. These 2-D and 3-D bitmap images may then be imported into the corresponding image record in the Access (TM) database, if desired, to support maintenance of records useful for clinical evaluations of the subject and to support development and evaluation of algorithms to extract features which can be correlated with the clinical conditions of the subject. FindEyes also optionally generates, via subroutine calls, an integrated display showing the 2-dimensional and 3-dimensional images of each eye, along with the interpupillary distance (between the eye pupil centers), and selected results from the eye search algorithms, presently the peak circularity, the pupillary radial standard deviation, the average intensity within the iris ring, and the result of the DeltaSum test described earlier.

After completing the eye search, FindEyes also writes out, for optional subsequent processing on the same computer or for transmission for further processing on a centrally located computer, another file containing the arrays of intensity values for the selected regions (presently 128 by 128 pixels) about the center of the right and left eye pupils; the pixel coordinates, in the original ST-7 image file, of the selected region for each eye and the estimated center for each eye pupil; the interpupillary distance (described above); and values from the intensity distribution for the original ST-7 image (most probable intensity value, maximum intensity value). FindEyes may also optionally include in this file another array containing the pixel intensities in a selected region encompassing the position of the calibration device (described earlier) within the overall image. Data integrity between this file and the original clinical data (to support the previously described image feature to clinical condition correlation) is preserved by automatically reusing the original image file name with an added suffix letter (presently a "D") to indicate that this new data file contains data extracted from the original ST-7 image file, which filename is automatically generated, assigned, and tracked by the Access (TM) database, described earlier, used in conjunction with the reflex photometer of the instant invention.

After completing the tasks outlined above, the FindEyes program terminates execution and returns control to the operating system and/or the Access (TM) database software.
Principal Subroutines The following sections provide a more detailed overview of the functions implemented by the principal subroutines called from the FindEyes main program.
Remote_Setup Subroutine The Remote_Setup subroutine reads the RemControls.txt file and stores the data values contained therein in the Remote_Program_Control Module and other modules as described earlier. The RemControls.txt file uses the Fortran Namelist approach for setting data values so that the program control variables and other supporting data can easily be modified by the user using a standard text editor.
Read_ST7

The Read_ST7 subroutine reads the file containing the data from the ST-7 digital camera, using, in the normal data collection mode, a file specification (path and filename) passed as a command line argument to the FindEyes program by the Access (TM) database software package. Optional modes permit use of filenames passed via a list file for batch processing.

In the normal data collection mode, the ST7 file is originally created by a commercially available software package called CCDOPS for Windows (TM) which is distributed by Santa Barbara Instrument Group for use with their ST7 digital camera as stated earlier. CCDOPS for Windows (TM) establishes a communications interface with the ST7 camera, which is integrated within the reflex photometer of the instant invention, through a parallel port on the host personal computer and sends the commands to the ST7 camera to cause it to take an exposure. CCDOPS (TM) then reads out the pixel by pixel intensity data and writes the data out to a file. The exposure parameters and filename to be used are passed to CCDOPS for Windows (TM) by the custom Access (TM) database software application package as described earlier. The image file created by CCDOPS for Windows (TM) includes a file header followed by the pixel by pixel intensity data in 16 bit unsigned integer format, using a lossless compression technique described in file format documentation available from Santa Barbara Instrument Group. Alternatively, other commercial software packages (e.g., CCDOPS (TM) for DOS, SkyPro) may also be used to interface with and control the camera, or custom code can be used to provide a more flexible direct interface to the camera using a command library provided by Santa Barbara Instrument Group. Some of these modes save the data in uncompressed or other formats. Alternatively, other digital cameras and their supporting software packages could also be used to obtain images with the reflex photometer of the instant invention.

Read_ST7 reads the ST-7 image file header block as well as the pixel by pixel intensity data in either the compressed or uncompressed formats described in Santa Barbara Instrument Group documentation. Data from the image file are stored in the Remote_ST7_Data module as described earlier.

In the present embodiment, and by way of example, the image data are stored in a Fortran 2-byte signed integer array (rather than a 4-byte signed integer array) in order to reduce the RAM memory required to run the code efficiently. This has the effect of reducing the dynamic range for intensity values which can be included in the array from the original range of 65,535 (unsigned 16 bit integer) down to a maximum intensity value of 32,767 (two byte signed integer format). This situation arises because the Fortran signed integer format uses the most significant bit of the most significant byte(s) composing the number to hold the sign value, and then applies a two's-complement interpretation of the value of negative numbers (having a 1 in the most significant bit). Unsigned 16-bit integer numbers from the ST-7 camera which exceed 32,767 will have the most significant bit set to 1 (vs 0 for intensity values less than or equal to 32,767). This 1 in the most significant bit position will be interpreted by the Fortran two-byte signed integer format interpretation as an indication of a negative number, and the remaining bits will be interpreted as though they represented a number in two's-complement format.

For a properly adjusted reflex photometer camera and flash light source of the instant invention, at most only a few pixels, if any, should exceed the 32,767 maximum upper value of the Fortran two-byte signed integer format, and these would probably be due to specular reflections from glasses or frames, consequently the exact values for pixels which exceed 32,767 are probably not important for image interpretation, and would be clipped or ignored by most of the image analysis techniques presently used. Consequently, in the present embodiment, pixel intensity values in the original image file which exceed 32,767 are clipped to the maximum value of 32,767 when stored in the two byte signed integer format. If it is determined that the full dynamic range of the original data is needed, one simple alternative is to redeclare the Fortran array variable used to store the array data as a four-byte signed integer rather than a two-byte signed integer. Although this will increase the storage space requirement for the image data, the effects on overall computer image analysis performance should be minimal for computers equipped with adequate RAM memory. Alternatively, the image data processing described herein could be implemented in another computer language, such as C, which accommodates the unsigned integer format.

As an interim measure to permit evaluation of the need, for commercial applications of interest, for preserving the full dynamic range of the ST-7 camera used in the present embodiment of the reflex photometer, additional logic has been provided in the present version of the Read_ST7 subroutine which scans the data read in from the ST-7 image file, recognizes pixel intensities which exceed the value of 32,767 (since these values are interpreted as negative numbers for the Fortran two-byte signed integer format), preserves a copy of the original pixel value in a separate, but much smaller four-byte integer array (presently sized for up to 100 such pixels), stores the corresponding coordinates of such pixels in coordinated arrays, and reassigns (clips) the pixel value in the two-byte signed array variable to 32,767. Read_ST7 also generates warning messages to the user when this situation occurs. The original intensity data for high valued pixels is thus preserved in this additional four-byte integer array (and corresponding pixel coordinate arrays) and made available for image analysis algorithms as needed with minimal increased storage requirements.

Set_Color_Intensities Subroutine

Figure 13A:
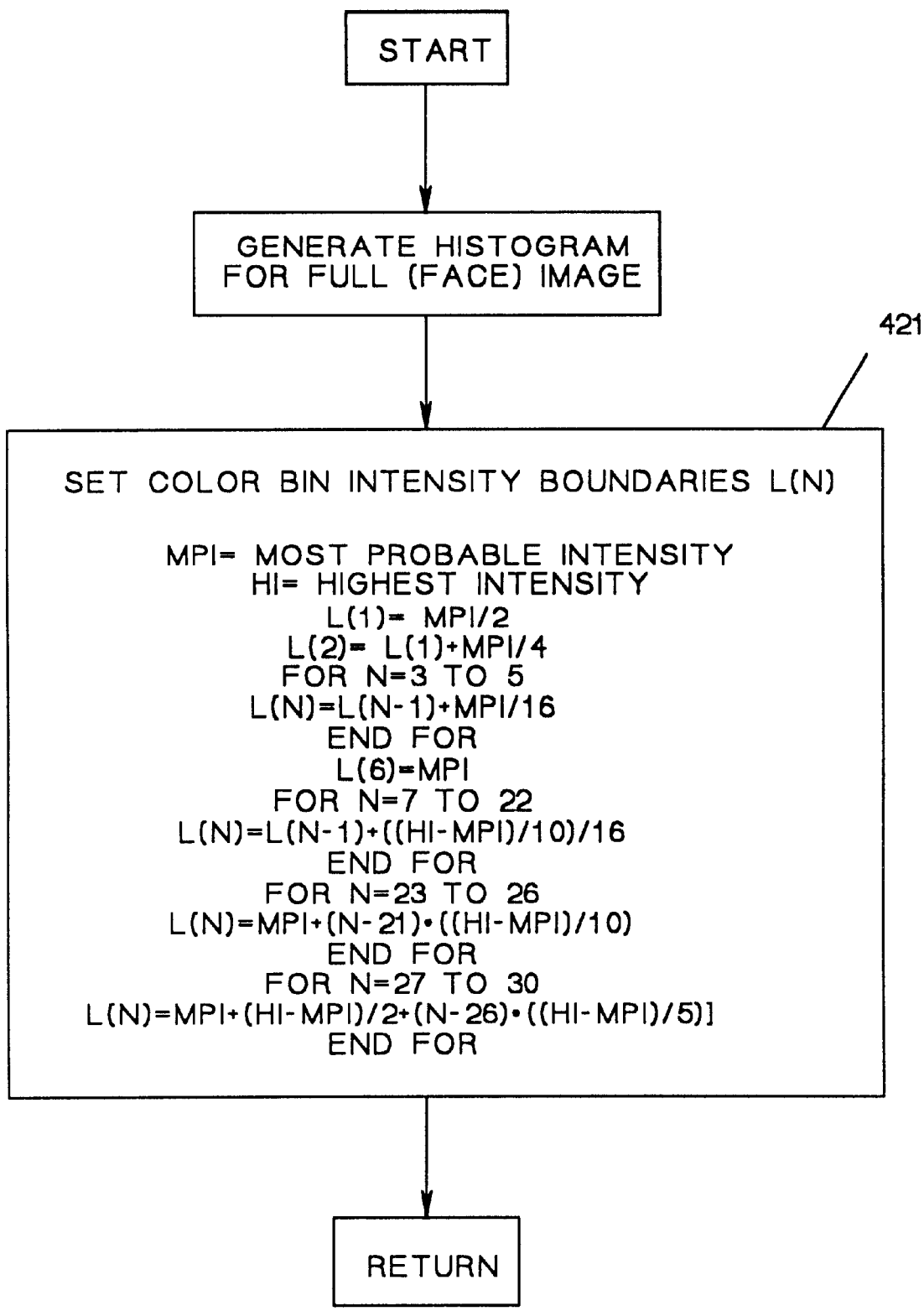
FIG. 13a is a flowchart illustrating setting of color intensities.

The Set_Color_Intensities subroutine establishes adjacent intensity ranges above and below the most probable intensity value (in the overall image) to which separate colors can be assigned to enhance the display of intensity patterns in the retina reflex image generated by the reflex photometer. The Set_Color_Intensities subroutine calls another subroutine, SetClipLevel, which determines the distribution (histogram) of intensity values and in particular determines the most probable intensity value and the maximum and minimum intensity values within the overall ST7 image file. The intensity region of greatest interest for intensity pattern correlation with eye clinical conditions is the region just above the most probable intensity value in most images and including, nominally, the lower ten percent of the intensity range between the most probable value and the maximum intensity value in the image. Consequently, the Set_Color_Intensities subroutine uses finer (smaller) ranges (bins) of intensities in this intensity region of greatest interest just above the most probable intensity value, and coarser (larger) bins for higher intensities above this region of greatest interest as well as for intensities below the most probable intensity value. In the present embodiment, Set_Color_Intensities establishes 30 adjacent intensity ranges (or bins) at box 421 in FIG. 13a for the overall range of intensities in the image and described as follows: one bin between zero intensity and one-half of the most probable intensity; one bin between one-half and three-quarters of the most probable intensity value; four bins from three-quarters of the most probable intensity value to the most probable intensity value; 16 bins within the intensity region of greatest interest just above the most probable intensity value (as described above); four bins above the region of greatest interest at increments of ten percent of the intensity range between the maximum intensity value and most probable intensity value; and four additional bins above the additional region just described at increments of twenty percent of the intensity range between the maximum intensity value and the most probable intensity value. The result of this process is a Fortran array containing the intensity levels which are to be used later in the FindEyes program as the boundaries between intensity regions for the purpose of assigning different colors to different intensity levels in the 2-dimensional and 3-dimensional images described earlier.

In alternative embodiments, more or fewer intensity ranges and colors may be used. Alternatively, the intensity ranges could be assigned in a similar manner to enhance the patterns in the region of greatest interest, but based on an offset from the peak or average intensity measured by pixels which image the "calibration device" described earlier. Thus, by using a light intensity meter to establish a calibration factor for the percentile of incident light intensity backscattered from the constant reflectance "calibration device" included in each instrument, and then using a separate offset based on the calibration measurements, an intensity color scale can be established which is more directly tied to the absolute reflectance (or percentage of incident light backscattered to the camera) of the features of an eye rather than relative reflectance (compared to most probable intensity values) as obtained by the approach presently implemented. The alternative approach (using the intensity backscattered from the calibration device) may provide an enhanced ability to monitor and measure subtle changes in a subject's eyes over time, as well as an enhanced capability for visually monitoring additional features (e.g., absolute reflectance for a specific region as mapped into a specific and consistent color value by the latter approach) which correlate with various clinical conditions.

SetClipLevel Subroutine

The SetClipLevel subroutine uses a very fast running technique to compress the distribution of intensity values (going up to 32767 as described above) into 4100 equally spaced "bins" and concurrently accumulate a distribution of intensity values into the 4100 bins. It does this by setting up outer and inner loops to address each pixel intensity value stored in the image array, dividing each value by eight (8) using integer arithmetic; using the division result, incremented by one (1), as an index for the histogram array, and then incrementing the indexed bin in the histogram array (of 4100 elements) by one (1) to record a pixel intensity within the range covered by the indexed bin. The result is a distribution (or number of occurrences) of pixel intensity values within each of the adjacent intensity value ranges represented by each of the 4100 elements, or "bins," of the histogram array. Other divisors, especially higher powers of two, and bin sizes could be used as alternatives, as well as other techniques for generating the histogram. However, integer division by powers of two runs very rapidly on a computer and a divisor of eight provides good resolution for the range of intensity values.

Other loops over the histogram array are then used to find the bin with the highest number of counts, corresponding to the most probable intensity value, and the maximum and minimum intensity values within the histogram array (rounded up to the next multiple of eight (8)). A value for "ClipLevel," which is used as explained below in screening the image data for possible eye pupil locations, is calculated by adding, to the most probable intensity value, an intensity value which is a user controlled fraction of the intensity range between the highest intensity value and the most probable intensity value determined as described above. The user control is invoked through a variable called "ClipFactor" whose value is set via the RemControls.txt file. The intensity range from the highest intensity value to the most probable value is divided by "ClipFactor" to determine the intensity value to be added to the most probable value to set the value of "ClipLevel." Thus, for example, a "ClipFactor" value of 20 will result in one-twentieth of this maximum to most probable intensity range being added to the most probable value to establish the value of "ClipLevel." An alternative approach of setting the value of ClipLevel based on an offset from the intensity measured from the "calibration device" could also be used; however, the approach disclosed above has been found to work well in accommodating the variations in light intensity and instrument response which have occurred during development and adjustment of the present embodiment of the instant invention.

ShowFace Subroutine

The ShowFace subroutine creates a 2-dimensional image of a subject's face using the intensity data captured by the digital camera in the instant reflex photometer invention. Using the QuickWin (TM) capabilities of the Microsoft Fortran PowerStation Developer Studio (TM), calls are made to graphics routines to insure the computer monitor is set to a sufficiently high screen resolution (nominally 800 pixels horizontally by 600 pixels vertically) to permit showing all the pixel data from the digital ST-7 camera (765 pixels horizontally by 510 pixels vertically) on the monitor screen. Additional calls create a graphics window within which the image is displayed. The image is created by using nested Fortran loops to assign color values to pixels on the monitor screen based on the intensities of camera pixels recorded in the image file. The colors may be assigned based on the tailored color intensity ranges established within the Set_Color_Intensities subroutine for the specific image file, or by using a fixed color vs intensity scale, or by directly assigning a pixel's intensity value, or some multiple thereof, as a red, green, and blue (RGB) "color value" for each screen pixel. Other color assignment alternatives would be to use different mathematical functions to map camera pixel intensity values into color values for monitor screen pixels.

In the present embodiment, the color values are assigned to screen pixels in nested Fortran loops using the SetPixelsRGB routine provided by the Microsoft Fortran Developer Studio (TM) together with a custom Fortran ColorValue function. The ColorValue function accepts as an argument a camera pixel intensity value from the double subscript image array element B(I,J) in the present embodiment and returns an RGB color value to be used for the monitor screen pixel. The ColorValue function uses an If-Then-Else If construct together with the intensity bin boundaries established by Set_Color_Intensities (and stored within the IntensityLevel array) to assign a color value from the EyeColors array. Color values in the EyeColors array can be selected by the user and input to FindEyes through the RemControls.txt file. Alternate approaches could use the graphics capabilities in other languages and software packages to achieve a similar result.

ShowFace3D Subroutine

The ShowFace3D subroutine provides a capability to generate 3-dimensional plots of the intensity patterns in the full image data from the digital camera. ShowFace3D creates a 3-dimensional effect by drawing an isometric view plot wherein the intensity data (or alternatively the logarithm of the intensity) for each pixel is plotted on the vertical axis and the row and column position of the pixel are used to determine its position in the base x-y isometric plane. The pixels in the screen display representing the intensity value for each camera pixel within a row of camera pixels are interconnected using a line drawing tool. The color of the line segment from one pixel to the next can be set based upon the intensity value of the beginning or ending pixel for the line segment, and using the intensity ranges from Set_Color_Intensities and the ColorValue function as described above for the 2-dimensional plot.

The isometric view is created using a technique commonly known as a "painters" algorithm. This technique begins by plotting the backmost row first (pixel intensity on the vertical axis vs pixel position in the row on the horizontal axis) at an appropriate offset within the image window. Intensity data for the next pixel row is then drawn on the screen beginning at an appropriate horizontal and vertical offset from the preceding pixel row data as determined by the viewing perspective to be created. By plotting successive rows with the baseline for the row shifted down and horizontally by one or more screen pixels, a top down 3-D view of the intensity values of the image is created. By plotting successive rows with the baseline shifted up by one of more pixels, a bottom-up 3-D effect is created. Shifting the horizontal starting point for the baseline for each new camera pixel row as its intensity data is added to the screen display creates an apparent shift in the viewing perspective. Since successive rows of data are written from back to front, the new data overwrites the previous row's data where the new data overlaps the plotted data for the preceding rows on the display screen, thereby creating a hidden line effect appropriate to the viewing perspective. The hidden line effect can be reinforced by first plotting each new row of intensity data using a polygon tool to connect the points, closing the polygon at some offset below or above the plotted row data (depending upon top-down or bottom-up viewing perspective), filling the polygon with a black fill or other color as desired, and then replotting the intensity data across the top of the polygon using the line segment colorization as described above to preserve the color vs intensity effect.

After making appropriate calls to graphics routines to open a new child window for the 3-D image with sufficient pixel height and width to accommodate the full image data plus the offsets used to create the isometric 3-dimensional view, ShowFace3D calculates the horizontal and vertical shifts to be used for each new row of pixel intensity data as it is added to the view to create the desired viewing perspective (based on user controlled parameters input from the RemControls.txt file). ShowFace3D then draws the data from back to front assigning colors to each line segment as described above to create the 3-D isometric view of the data.

An alternative subroutine, ShowFace3DPoly, is used when it is desired to incorporate the additional hidden line effect described above. ShowFace3DPoly implements the same offset and colorization logic described above but adds the intermediate step of first drawing a polygon for each row of pixel intensity data to enhance the hidden line effect.

As additional alternatives, other embodiments can implement more sophisticated 3-dimensional drawing effects, using either custom code or commercially available graphics libraries, with surface patch shading and a capability to rotate the image on different viewing axes and scale the data differently to aid in visualization of the intensity data. However, the algorithms described above for the present embodiment have the advantage of not being computationally intensive.

Find_Eyes_1 Subroutine

Figure 13B:
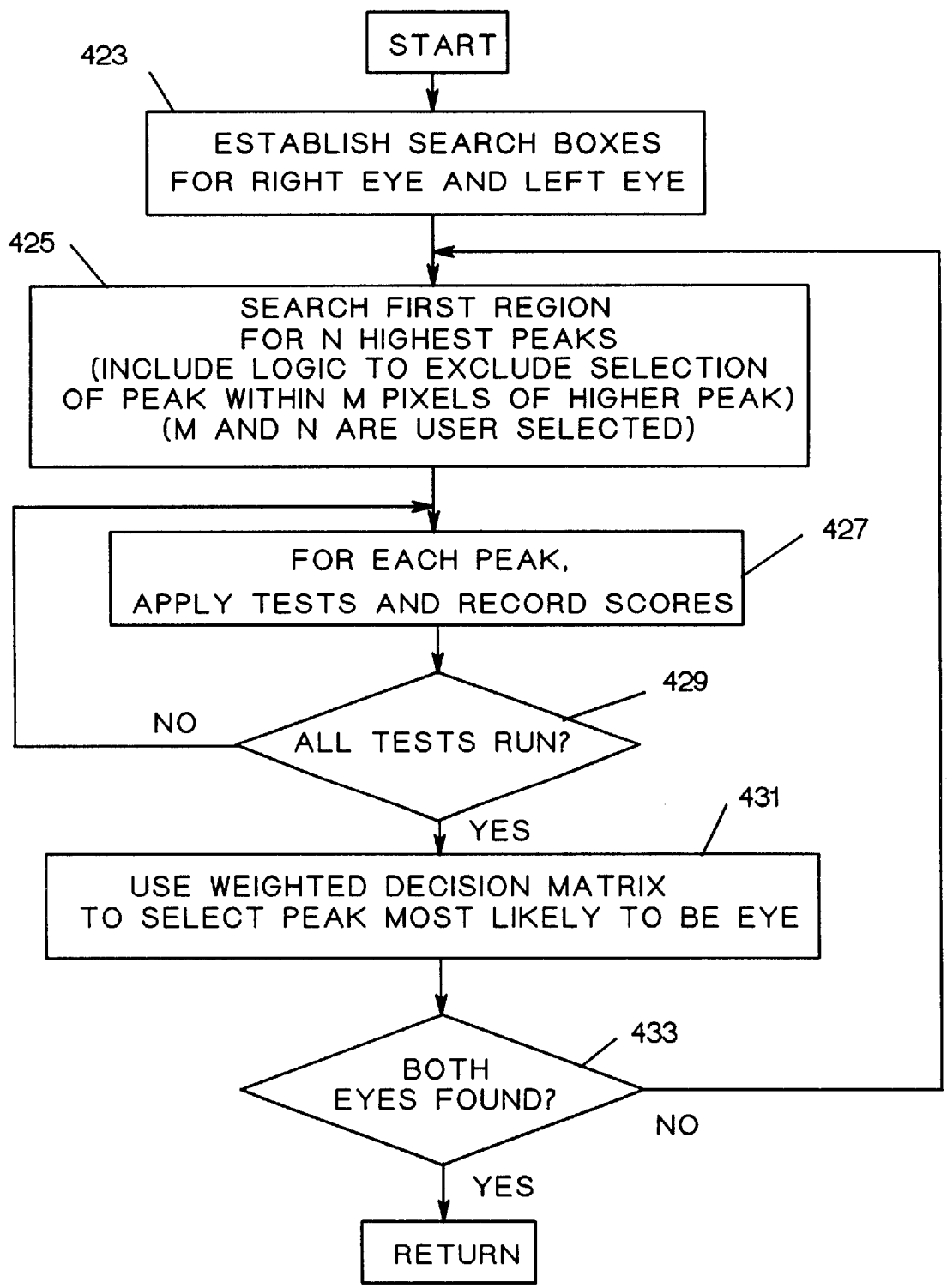
FIG. 13b is a flowchart showing a routine entitled Find_Eyes_1.

The Find_Eyes_1 subroutine, as shown in FIG. 13b, first scans user-defined rectangular search regions at box 423 within the right and left halves of the full ST-7 image to identify up to some number (presently 10) of the highest relative intensity peaks within each search region (box 425). The search logic invokes a user controllable exclusion zone about each peak (nominally about 20 pixels in the present implementation) so that the peak search returns separate relative peaks (each of which may encompass regions of many pixels), not just the highest (ten) pixel values, which may all be within the same peak. Then, at box 427, for each intensity peak (which is not too close to the edge of the overall image), a series of tests are performed (via a Fortran loop at box 429 over the highest peaks just found) to help determine if the region (pixels) surrounding each candidate peak has characteristics which would be expected for a true eye (as opposed to a peak created by a reflection from glasses frames or lens, tear ducts, or other sources). Tests which may be invoked include Minima Ring Circularity; Radial Minima Radial Variance; Radial Minima Intensity Variance; Radial Minima Midpoint Variance; Convolution with an Eye Pattern Mask; Peak Circularity, Radial Variance, Radial Standard Deviation, and Peak Radius (at a given intensity level selected to capture the pupillary aperture); Pupil Aperture Average Intensity; and Iris Average Intensity. Key parameters from each test for each peak can be stored in multiple dimensioned Fortran arrays for later use in selecting the peaks which are most probable to be in the locations of the eyes. The peak selection logic multiplies each key parameter by a weighting factor at box 431 (selected based on experimental data or heuristic techniques) and accumulates the results into "Selection" arrays (for each peak on the right and left side respectively). The intensity peaks most likely to be due to eye pupils are then selected based upon the lowest (or highest) value in the Selection arrays for the right and left eyes. The pixel coordinates of the updated center estimate of the associated pupillary apertures are saved and used for saving out the pixel regions (128 by 128 pixels in the instant invention) about each eye pupil center to be used for additional analyses. At box 433 the inquiry is made as to whether both eyes have been found, and if not then the program loops back to box 423 to test another spike.

Find_Eyes_2 Subroutine

Figure 13C:
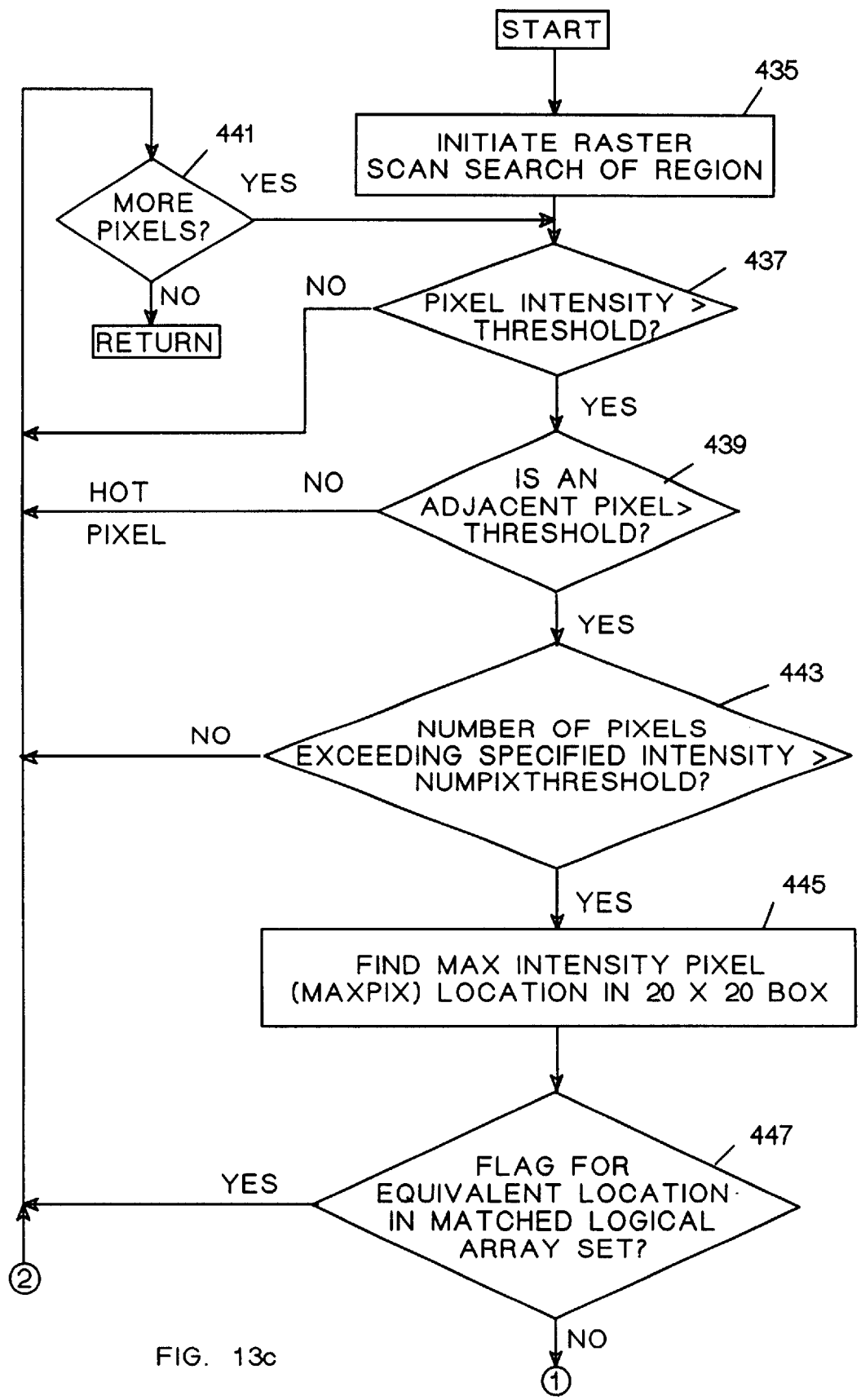
FIGS. 13c, 13d, 13e and 13f are flowcharts showing a routine designated Find_eyes_2.

The Find_Eyes_2 subroutine (FIGS. 13c, 13d, 13e, 13f) implements one alternative approach for locating the eye pupils within an image created using the ST-7 digital camera integrated into the reflex photometer of the instant invention. As summarized earlier, the Find_Eyes_2 subroutine implements an eye pupil location strategy which attempts to locate and discriminate the eye pupils by implementing a single pass raster scan (box 435 of FIG. 13c) within search boundaries (rectangular boxes) established separately within the overall ST-7 image for the right and left eyes, and performing multiple tests within a given region of the image when pixels are encountered which have an intensity level which exceeds the basic screening criteria. The tests are designed to reject regions which are not good candidates for the eye pupil location (e.g., intensity peaks caused by hot pixels, reflections from eyeglass frames and lens, reflections from tear ducts) with minimal computational effort while applying sufficient tests to establish confidence for the selection of the "true" eye pupil locations.

In the present embodiment, Find_Eyes_2 is called by FindEyes with a subroutine argument indicating whether the search boundary box for the right or left eye is to be searched. Find_Eyes_2 initiates the search, within the overall ST-7 camera image data captured using the instant invention, at the row and column index which corresponds to the upper left corner of the "search box" established by user input parameters (via the RemControls.txt file) for the right eye or left eye as specified in the subroutine argument. The basic search pattern, implemented by nested loops over columns and rows, proceeds through the image array data in a manner corresponding to a horizontal scan of the pixels in one row of the search box, followed by horizontal scans of the succeeding rows of pixel data within the search box. Although a top down horizontal raster scan search pattern is disclosed, alternative starting locations and search patterns could be used and may provide more rapid location of the eye pupils in some cases (e.g., initiating the search just above the vertical center of the search box where the eye pupil location is most likely to be, searching the region above only if the eye pupil is not located below the search initiation region).

At each pixel, a series of tests are initiated to determine whether the pixel may be part of the pupil region of an eye or whether it may be rejected. The tests are based on characteristic intensity patterns associated with the pupil of an eye as imaged with the instant invention. The tests described below are implemented, in the present embodiment, by a set of nested If-Then-Else blocks so that, when a pixel fails a test, logic flow falls to an applicable "Else" block which records which test was failed (for evaluating FindEyes code performance in different conditions), and processing then moves on to the next pixel in the search pattern described above.

The first test (box 437) requires that the intensity level for the pixel exceed an intensity threshold, "PixIntensityThreshold," which in the present embodiment is set equal to the value of the ClipLevel variable, which is set based upon the most probable intensity value and the pixel intensity distribution from the overall ST-7 image using the Set_Clip_Level subroutine as described earlier.

For pixels which pass the pixel intensity threshold test, a test is performed at box 439 to reject "hot pixels". The hot pixel test checks whether any of three adjacent pixels (including the next pixel on the same row and the corresponding pixels on the next row) also exceed the value of PixIntensityThreshold. If none do, the pixel fails and processing moves on to the next pixel (box 441) in the overall search pattern. For pixels which pass the "hot pixel" test, a small adjacent region (in the present embodiment, a 20 pixel by 20 pixel box with the pixel under test at approximately the [6,6] coordinate position of the 20×20 box) is searched using separate nested loops to count the number of pixels (NumPix) within the small adjacent region (hereinafter called the 20×20 box) whose intensity values exceed the value of ClipLevel and to identify the location (MaxPixX, MaxPixY) of the pixel having the highest intensity value (MaxPixIntensity) within the 20×20 box. If the value of NumPix is less than the value of the user defined value of NumPixThreshold, input to FindEyes via the RemControls.txt file, the pixel under test fails the 20×20 box test and processing moves on to the next pixel at box 441 in the overall search pattern.

For pixels which pass the 20×20 box test, the testing falls through to box 445, now shifting focus to the pixel at the currently defined MaxPixX,MaxPixY location. A "flag" for the equivalent location in a separate logical array, PeakFlag (maintained to minimize redundant processing), is checked at box 447 to determine whether this MaxPixX, MaxPixY location has already been evaluated as a possible eye pupil location. If the PeakFlag check indicates that this MaxPixX, MaxPixY pixel location has already been evaluated (and failed) as a possible eye pupil location, then the processing focus returns to the next pixel at box 441, in the original overall search pattern, following the pixel which prompted the 20×20 box test.

Figure 13D:
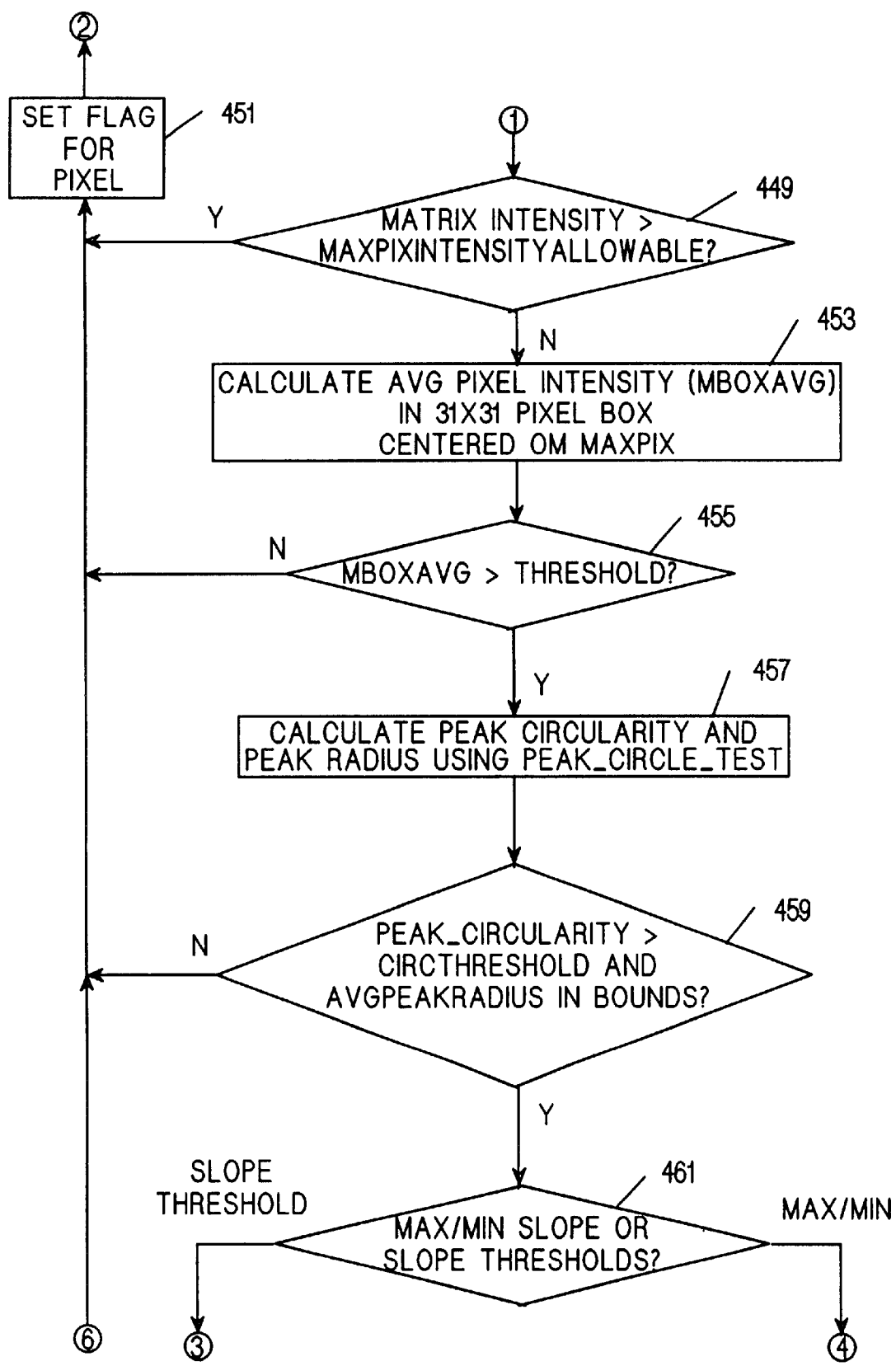
Figure 13E:
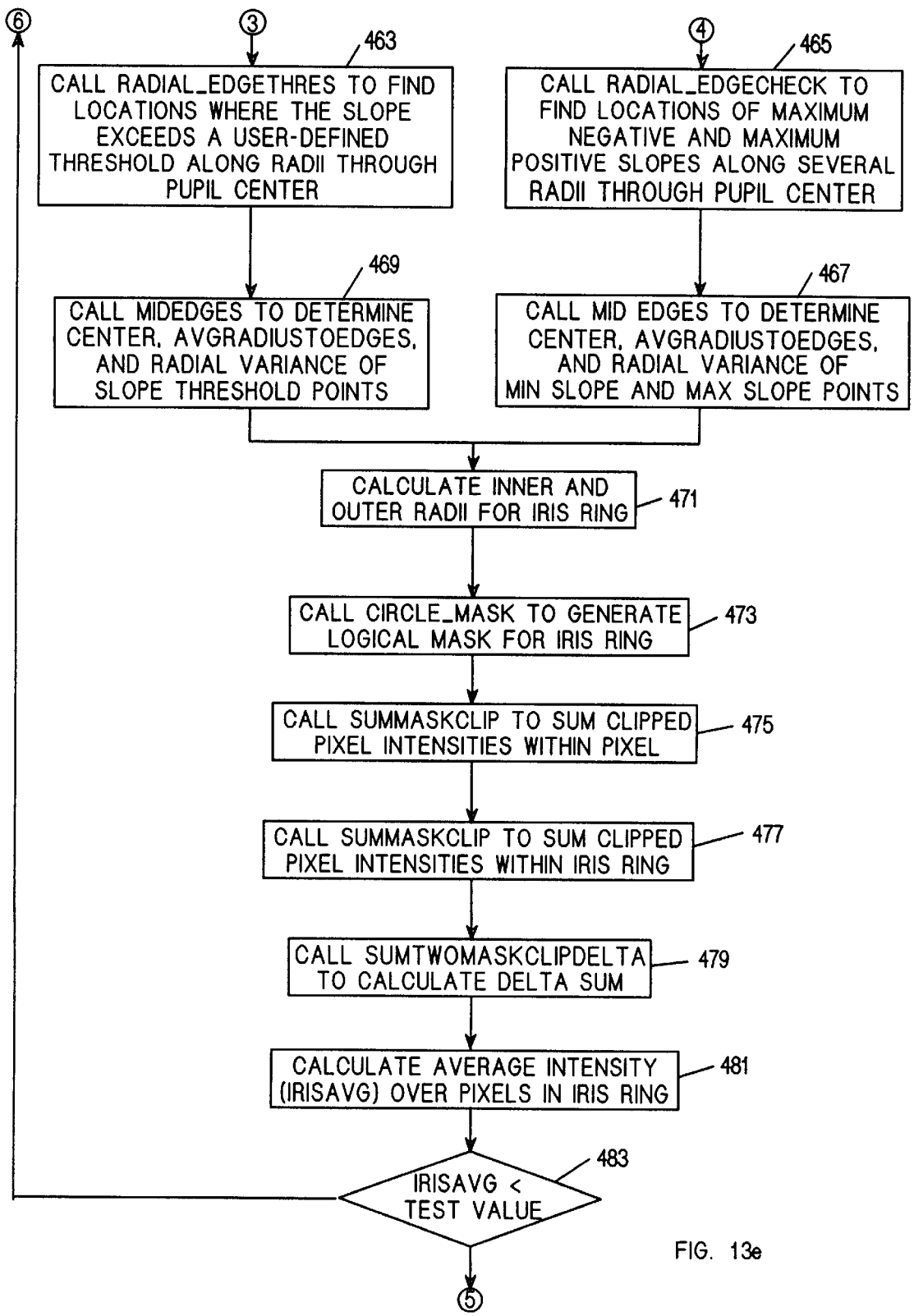
Figure 13F:
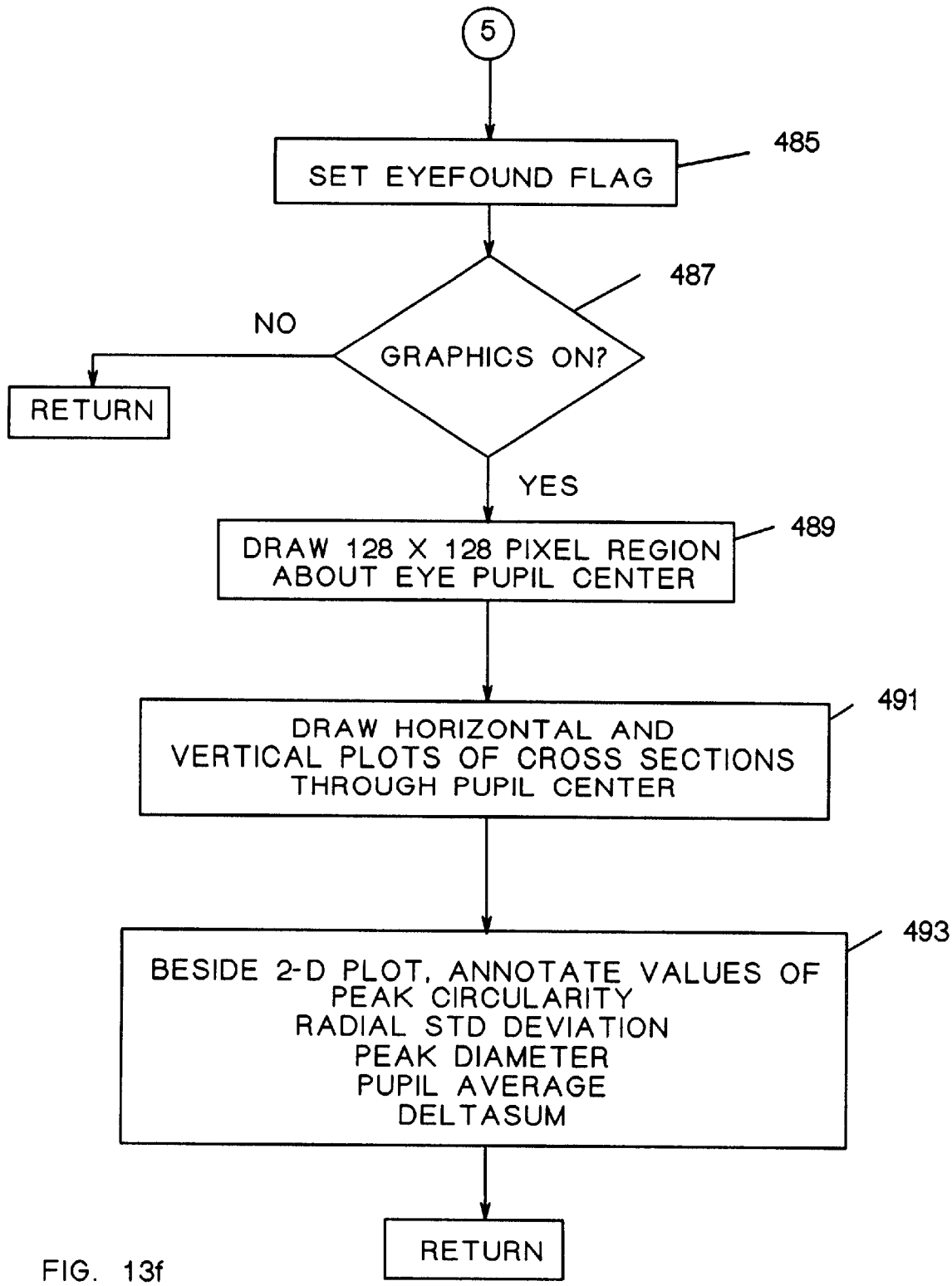

When the PeakFlag check indicates that the current MaxPixX, MaxPixY pixel location has not already been evaluated, then the program moves to box 449 of FIG. 13d, where the value of MaxPixIntensity for this pixel location is compared with a user defined maximum allowable pixel intensity threshold, MaxPixIntensityAllowable, input via the RemControls.txt file, to determine whether the MaxPixX, MaxPixY pixel should be rejected based on its intensity value being too high. The rationale for including this test was an expectation that at least some of the specularly reflected intensity from eyeglass frames and lens, particularly polished wire rimmed eyeglass frames, may be sufficiently higher than the range of intensity values reflected from the tear film, lens, retina, and other features associated with the pupil location of a true eye that this test may provide another useful discriminant for distinguishing intensity peaks related to eye pupil locations from intensity peaks related to other effects. While the utility of this test as an individual discriminant may be questionable due to the wide range of specular peak reflections from different eyes, false rejection based upon this test can be eliminated in the present embodiment by setting the user input value of MaxPixIntensityAllowable equal to the maximum intensity value which can be captured by the camera or stored in the intensity array (65,535 or 32,767, respectively, for the present embodiment as discussed above in the Read_ST7 subroutine description), or another high value. Nevertheless, if the user input value of MaxPixIntensityAllowable is set to a lower value and the present MaxPixX,MaxPixY pixel location being evaluated is rejected based upon this test, then a rejected flag is set at box 451 for the corresponding pixel location within the PeakFlag array, and processing focus returns to the pixel at box 441, in the overall image search pattern, next following the pixel location which prompted the 20×20 box test described earlier.

If the MaxPixX, MaxPixY pixel location being evaluated passes the MaxPixIntensityAllowable test as just described, the average pixel intensity (MBoxAvg) within a 31 pixel by 31 pixel box centered at the MaxPixX, MaxPixY pixel location is calculated at box 453 using another set of nested loops. If the value of MBoxAvg is less than or equal to the sum of the most probable intensity value, established within the Set_Clip_Level subroutine as described earlier, and another user defined variable value, Box31Threshold, input via the RemControls.txt file, then the MaxPixX, MaxPixY pixel location is rejected, a rejected flag is set at box 451 for the corresponding pixel location within the PeakFlag array, and processing focus returns to the pixel at box 441, in the overall image search pattern, next following the pixel location which prompted the 20×20 box test as described earlier. Box31Threshold is used at box 455, in the present embodiment, to establish an offset intensity threshold above the most probable intensity value for the overall image and to enforce a test requirement, based on experiments with prototypes of the instant invention, that, to be accepted as a candidate eye pupil location, a pixel region within the overall image (i.e., the 31 pixel by 31 pixel box in the present embodiment) should have an average intensity value which exceeds the most probable intensity value of the overall image by some amount (nominally 10 units of intensity in the present embodiment).

If the MaxPixX, MaxPixY pixel location being evaluated passes the Box31Threshold test just described, then the "circularity" and some other characteristics of the higher intensity region surrounding the MaxPixX, MaxPixY location are evaluated at box 457 using a subroutine called Peak_Circle_Test. Using techniques described in more detail in the Peak_Circle_Test subroutine description, the Peak_Circle_Test subroutine algorithm locates the edges, for a specific range of intensity levels, of the raised intensity region surrounding the MaxPixX, MaxPixY pixel location. Peak_Circle_Test then determines a center, average radius, radial standard deviation, and the peak circularity of the "edge" pixels, as well as some other parameters described later. The peak circularity is defined as the percentage of "edge" points which lie within a ring about the estimated center of the group of "edge" pixels, which ring has user defined inner and outer radius offsets from an average radius calculated by Peak_Circle_Test. Find_Eyes_2 then compares the results of the Peak_Circle_Test analyses to user defined thresholds at boxes 459 and 461, again input via the RemControls.txt file, to determine if the region surrounding the MaxPixX, MaxPixY location is likely to be the pupil region of an eye or whether the region is more likely due to a reflection from some other source and should be rejected. In the present embodiment, if the value of PeakCircularity returned from Peak_Circle_Test is less than the user input threshold value, PeakCircularityThreshold, or if the calculated average radius of the possible eye pupil region is not within the user defined radius limits, MinAcceptablePupilRadius and MaxAcceptablePupilRadius, then the MaxPixX, MaxPixY location being testing is rejected, a rejected flag is set at box 451 for the corresponding pixel location within the PeakFlag array, and processing focus returns to the pixel at box 441, in the overall image search pattern, next following the pixel location which prompted the 20×20 box test as described earlier.

If the PeakCircularity and AvgPeakRadius values calculated by Peak_Circle_Test are within acceptable limits, then the program proceeds from box 461 to one of two alternative approaches (boxes 463, 465) for locating the edges of the pupillary aperture is invoked to help evaluate the utility of the somewhat different and potentially faster approaches to estimating the center of the eye and to gain confidence that the candidate peak represents a true eye location. Depending upon a user selected option, one of two subroutines is called to locate the edges, by use of digital edge filters, of the intensity peak being evaluated. One subroutine, Radial_EdgeCheck, finds the locations of the maximum negative and the maximum positive slope in pixel intensity values along each of several lines going radially outward from the "center" of the candidate eye pupil location being evaluated (eight radial lines at 45 degree angle increments in the present embodiment). The maximum negative slope should correspond to the transition from the pupillary aperture to the iris ring, and the maximum positive slope should correspond to the transition from the iris ring to the sclera, or white, of the eyeball. Radial_EdgeCheck finds the maximum negative and positive slopes at box 467 by calculating the output value of a digital edge filter applied to image intensity data at each of several radius steps over a range of radius values. The radius values are selected to permit the slope search to begin within the pupillary aperture and extend through the outer edge of the iris for infants through adults (a radius range of approximately 20 to 55 pixels from "center" is used in the present embodiment). The maximum and minimum output values resulting from multiplication and summation of the digital filters, which are tailored for slopes in the direction being searched, with the image intensity data for pixels surrounding the pixel at each radius step (along a specific radial line) correspond to the most positive and most negative intensity slopes in the directions of the radial lines and are saved in an array for later use.

The other subroutine (box 463), Radial_EdgeThres, beginning from radial positions within the iris ring but proceeding in toward the "center" of the candidate eye pupil, finds the position along each of several radial lines (also eight radial lines at 45 degree increments in the present embodiment), where the maximum slope exceeds a user defined threshold, input via the RemControls.txt file. By appropriate selection of the edge threshold, the slope threshold search for each radial line can be tailored at box 469 to locate an appropriate transition point from the iris ring to the pupillary aperture.

The starting radius for the searches along the radial lines is important for both the Radial_EdgeCheck and the Radial_EdgeThres subroutines. In the Radial_EdgeCheck subroutine, if the starting radius is too far into the pupillary aperture from the outer edge, it is possible that the subroutine could return maximum positive or negative slope locations which result from intensity gradients within the pupillary aperture (e.g., caused by cataracts or abnormal refractive conditions) rather than finding the intended slope changes associated with transitions between pupil and iris, and iris and sclera, as described above. Similarly, since the edge threshold search within Radial_EdgeThres stops and saves the location on any given radial line where it first encounters a slope which exceeds the user defined slope threshold, it is also important to help insure that the search is begun within the intended relative position within the eye. For the Radial_EdgeCheck logic, the desired radial search for any given radial line begins just inside the edge of the pupillary aperture and proceeds outward. For the Radial_EdgeCheck logic, the desired radial search begins approximately within the middle of the iris ring thickness and proceeds inward toward the pupillary aperture, so that the first slope encountered which exceeds the user input threshold criteria should be within the base of the pupillary aperture where the intensity level transitions from the lower iris intensity level to the higher pupil reflex intensity level. To enhance the performance of these radial edge searches, a capability has been provided in the present embodiment to use the estimate of pupillary radius from the Peak_Circle_Test subroutine, together with user defined offsets (negative or positive), RadChkStartRadiusOffset and RadThresStartRadiusOffset, which are added to the average radius from Peak_Circle_Test, to determine the starting radius for the respective edge test techniques. This approach provides an adaptive accommodation to the wide variation in pupil aperture radii between various subjects (e.g., infants and adults) and between undilated and dilated eyes.

After using either Radial_EdgeCheck or Radial_EdgeThres to find the locations of the "slopes" (maximum or threshold) on the radial lines which should correspond to the pupil to iris transition area, then an alternative estimate of the center of the pupillary aperture is calculated at box 471, based on the average horizontal and vertical coordinates for the "slope" point locations, using a subroutine called MidEdges. MidEdges also calculates an alternative average radius, AvgRadiusToEdges, based on the average distance between "slope" points on opposite radials. Although the estimates of pupil center and radius obtained from these calculations are not used in the eye selection decision logic in the present embodiment, these alternative data are used to generate optional displays of the center location and radius which can be drawn over the eye pupil regions to permit a comparison with the center position and radius determined via the Peak_Circle_Test subroutine disclosed elsewhere herein. These alternative techniques for determining the eye pupil center location and radius may be incorporated into the operational decision logic in a later embodiment of the instant invention if they are determined to offer benefits (e.g., enhanced accuracy in identifying and discriminating eye pupils from other intensity peaks, reduced computational load) over the techniques disclosed and used in the present embodiment.

The Find_Eyes_2 subroutine next calculates estimates for the inner radius, IrisInnerRadius, and outer radius, IrisOuterRadius, of the iris ring by adding user defined offsets, IrisInnerRadiusOffset and IrisOuterRadiusOffset, respectively, to the average pupil radius calculated by the Peak_Circle_Test subroutine. Tying the iris radius estimates to the pupillary radius estimates from Peak_Circle_Test via the use of offsets enhances the capability of the Find_Eyes program to adapt to and accommodate the variations of iris ring diameters between subjects and particularly between undilated and dilated eye pupils in the application of additional tests for eye locations and features related to clinical conditions.

Find_Eyes_2 next calls the Circle_Mask and Iris_Mask subroutines at box 473 to generate logical masks for the pupillary aperture and for the iris ring using the pupil and iris radii calculated as described above. These mask arrays are then used with the SumMaskClip subroutine at boxes 475 and 477 to expedite calculation of the average pupillary intensity and the average iris ring intensity for the candidate pupillary aperture being evaluated. SumMaskClip calculates the sum of the pixel intensities for pixels within the mask region centered on the center coordinates estimated by Peak_Circle_Test. For pixels whose intensity level exceeds the ClipLevel set within the SetClipLevel subroutine, SumMaskClip clips, or limits, the intensity value to the value of ClipLevel to prevent undue effects on the pupil and iris average intensity values from specular reflections.

Find_Eyes_2 next calculates the value of a variable called DeltaSum at box 479 using a subroutine called SumTwoMaskClipDelta which, for pixels within the regions covered by the logical masks, calculates and sums the differences between each pixel and the DifferenceLevel. In the present embodiment, the DifferenceLevel is set equal to the CircleTestStartLevel, which is calculated within the Peak_Circle_Test subroutine as described elsewhere herein.

Next, the average intensity over the iris ring, IrisAvg, is calculated at box 481 and compared with a test intensity level determined by adding a user input parameter, IrisAvgMaxOffset, to the CircleTestStartLevel. If IrisAvg is less that this test intensity level, then at box 483 the region under test is assumed to be an eye pupil; an EyeFoundFlag variable is set at box 485; a 2-dimensional intensity colored view of the 128 pixel by 128 pixel region around the eye is drawn on the monitor at boxes 487, 489, 491 and 493 using the same technique as described above for ShowFace; plots of the horizontal and vertical cross section of the intensity profile through the center of the pupil are added beside the 2-dimensional view; and the values of peak circularity, radial standard deviation, peak diameter, pupil average, iris average, and delta sum are added to the display beside the 2-dimensional view. At this point, processing terminates within Find_Eyes_2, and control is returned to FindEyes, which may call Find_Eye_2 again to search for the other eye if necessary.

If the value of IrisAvg is greater than the test intensity level described, the EyeFoundFlag is not set, and the original search pattern is resumed beginning with the next pixel following the pixel which initiated the 20×20 box test described earlier. If the outer search loops are completed and no region is located which meets the criteria outlined above to be declared an eye pupil region, then the EyeFoundFlag is not set, and control is returned to FindEyes, which may call Find_Eyes_2 again to search for the other eye if necessary.

In a different embodiment, to minimize the possibility of rejection of an eye pupil region which should have been detected and accepted, additional logic may be added to the search approach outlined above to permit another search of the region with modified search thresholds, or to permit more detailed (but more computationally intensive) searches using more powerful techniques (e.g., convolution with intensity filters tailored for different eye sizes, application of a Hough transform).

Minima_Ring Subroutine

Figure 13G:
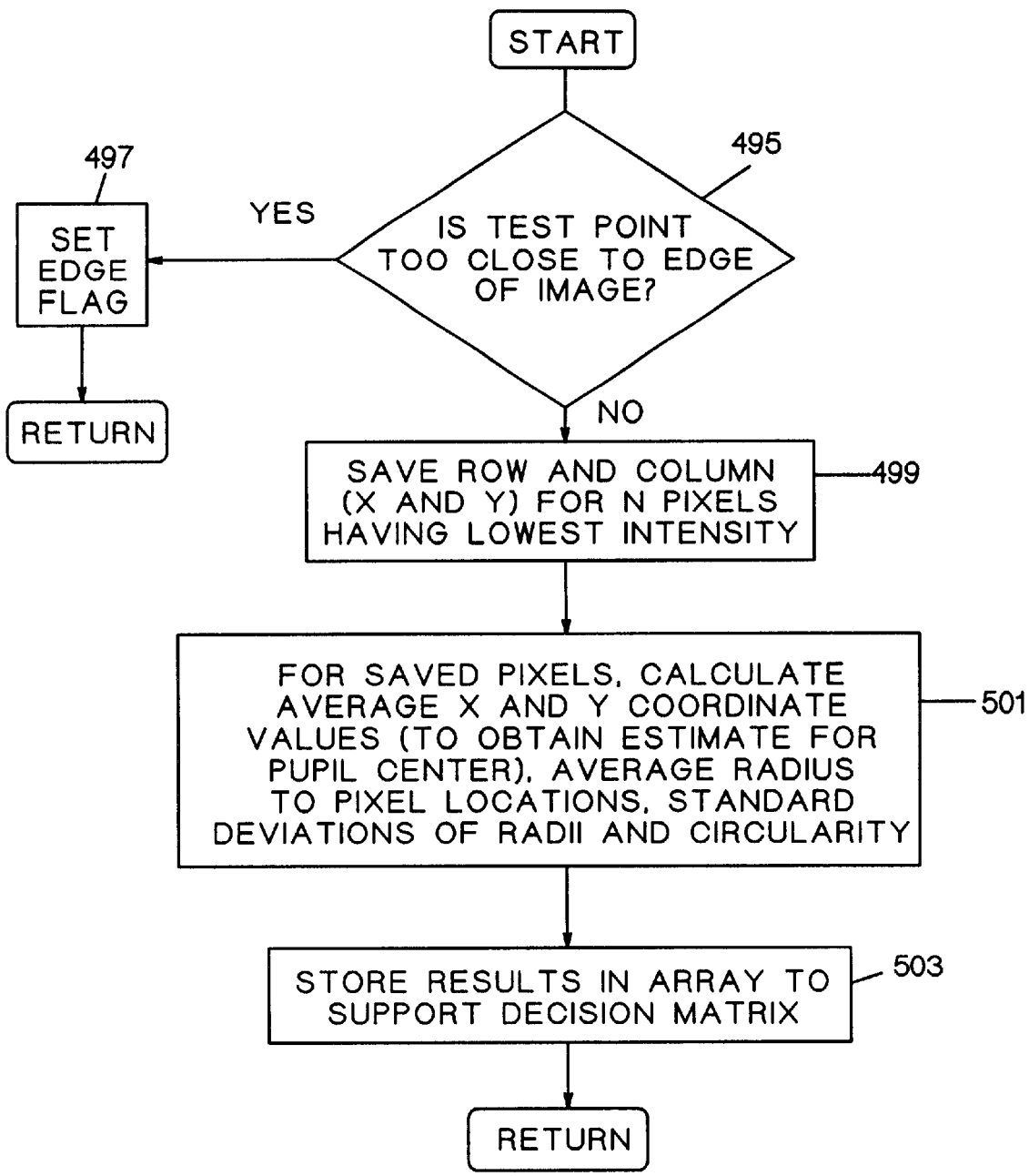
FIG. 13g is a flowchart showing approximate determination of a pupil center.

The Minima_Ring subroutine, as shown in FIG. 13g, implements a test, called the minima ring test, which can be applied to evaluate whether a given intensity peak is likely to be caused by an eye pupil based upon the observation that in images collected with the reflex photometer, the pupil of an eye is normally surrounded by a ring of pixels (the iris region) wherein the pixel intensity values are generally lower than other points within certain rectangular search bounds (nominally approximately 128 pixels by 128 pixels in the present embodiment) established about the candidate eye center location. Initially, at box 495, a test is made as to whether the intensity peak is too close to the edge of the image, thus not being representative of a pupil. Where the answer is YES, then at box 497 an edge flag is set, and the program returns. Where the answer is NO, and for a specified number of pixels having the lowest intensity values (box 499, nominally approximately 5000 pixels) within a specified search region (nominally approximately 64 pixels in each direction from the candidate intensity peak to be tested) and for a number of such intensity peaks (nominally 10 peaks each for the right eye and left eye search regions within the image), at box 501 the values calculated and stored include: the average coordinates for the identified minimal points (representing an updated estimate of the center coordinates of the eye pupil if the intensity peak represents an eye location); the average radius of these minima points from the updated estimate of the candidate eye "center" coordinates; the standard deviation of the radii to the minima points from the updated "center" location; and a "circularity" value based upon determining the percentage of points which lie within a ring of a specified delta radius about the average radius described above. The stored values also include "flags" used to indicate whether a given intensity peak location was too close to the edge of the image to complete the minima ring test as well as "flags" to control the execution of different steps implementing the minima ring algorithm. At box 503 the results are stored in an array adapted to support a decision matrix.

Peak_Circle_Test Subroutine

The Peak_Circle_Test subroutine implements another test which can be applied to determine whether a given intensity peak in the image is likely to indicate the location of an eye pupil. This test is based upon the observation that in most individuals, the image feature caused by the transition between the pupil of an eye and the iris of the eye is very nearly circular. Consequently, intensity peaks caused by reflections from the tear film on the cornea of an eye are likely to be surrounded by a circular feature where the light pattern transitions from a bright area (the pupillary reflex) to a darker area (due to the reduced light reflected back from the iris of the eye). Intensity peaks caused by reflections from glasses frames or lens, tear ducts, and other non-eye sources are less likely to be surrounded by a circular feature representing a transition from a light (higher intensity) region to a darker (lower intensity) region. The circularity of the region of intensity transition from lighter to darker regions at the pupil to iris transition in most eyes provides a useful discriminant for distinguishing high intensity regions caused by the desired pupillary reflex from other high intensity regions caused by other reflections. This test can be implemented for either the full circle (360 degrees) around each point as well as for portions of a circle (for example, a 270 degree arc) to accommodate cases where, for example, partial overlap of the eyelids, or a cataract near the edge of the pupillary aperture, prevent a full circle from being visible in the eye image.

Figure 13H:
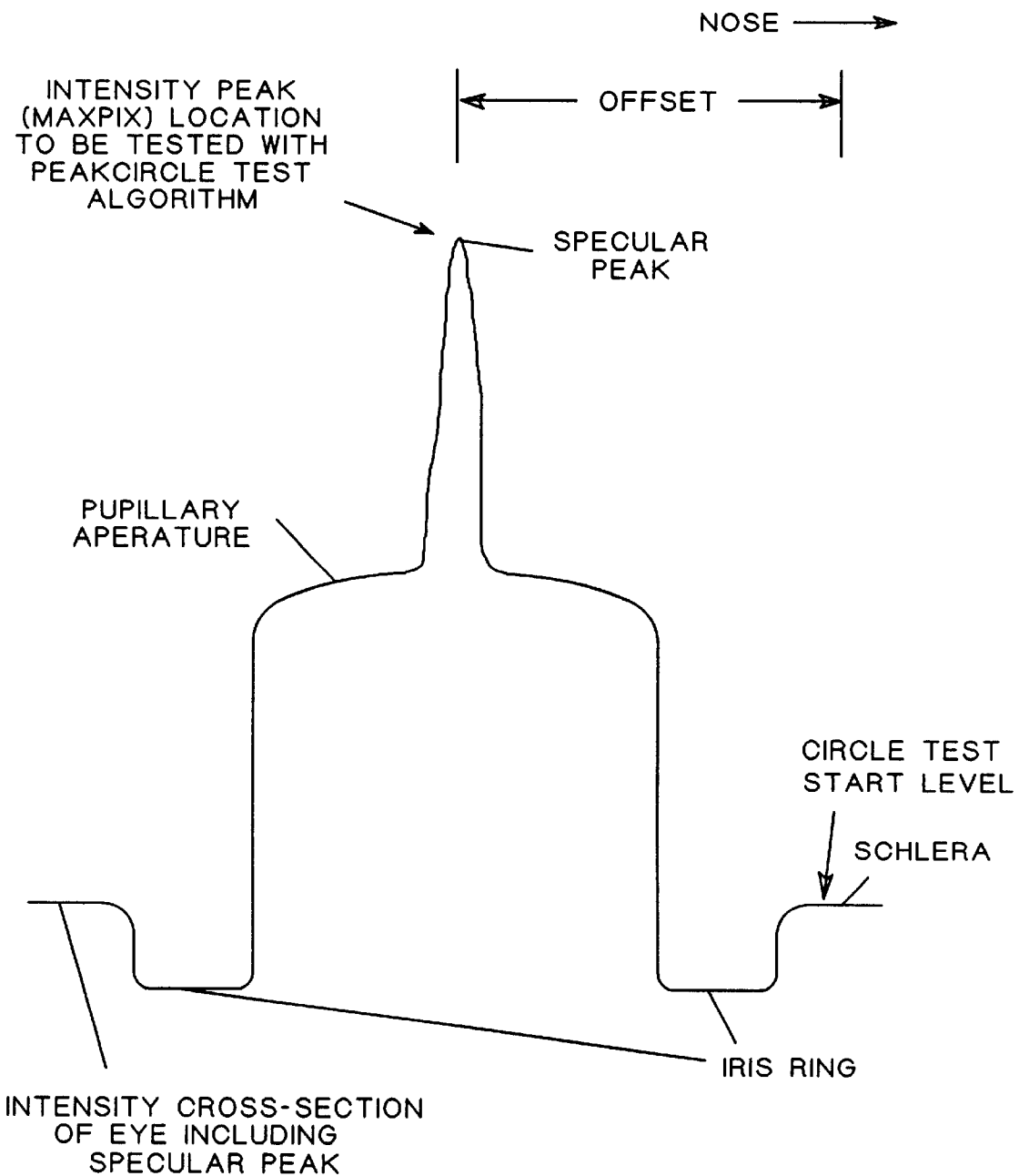
FIG. 13*h* is a pixel intensity profile cross-section of a normal eye.
Figure 13I:
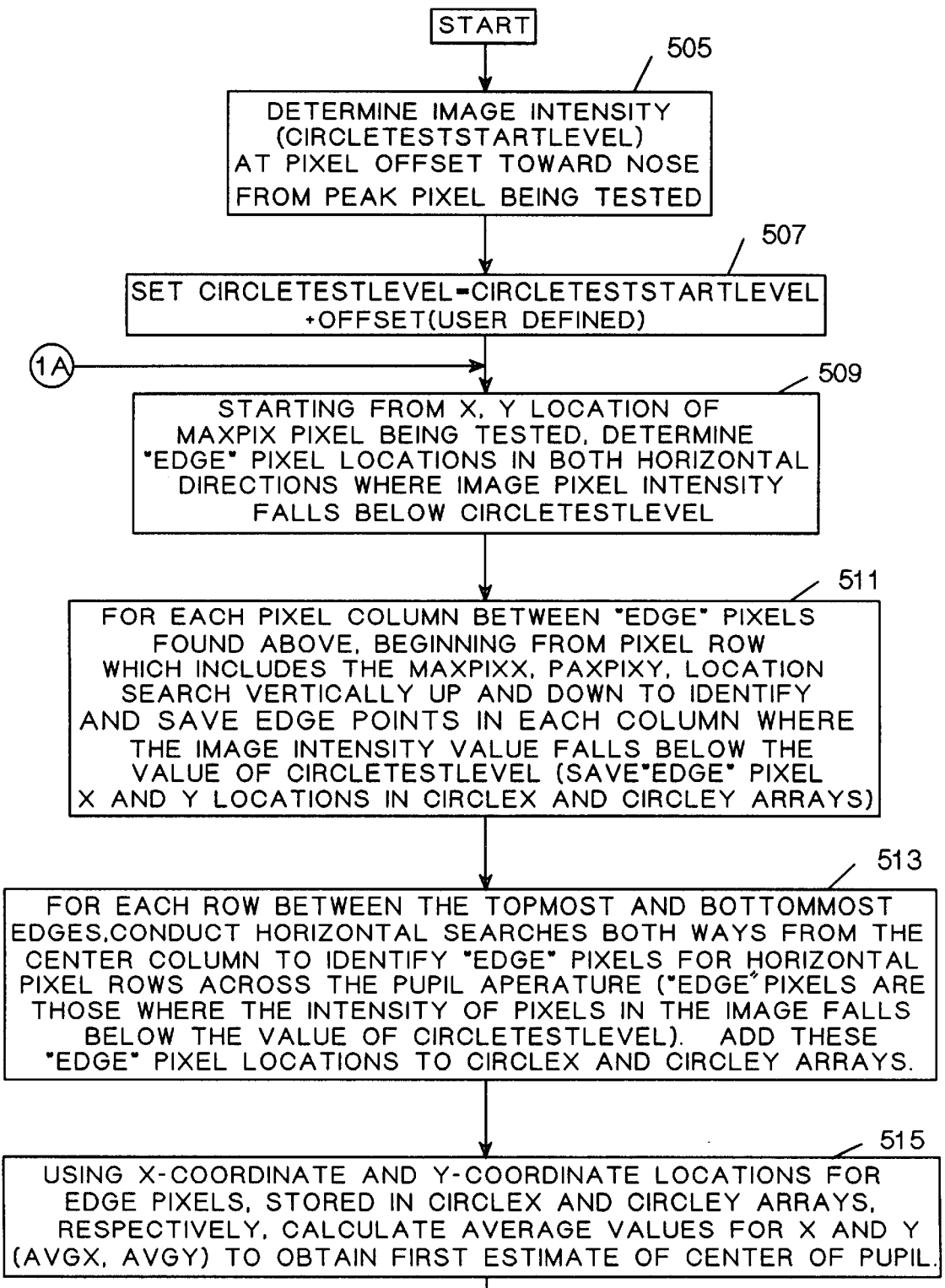
FIGS. 13*i* and 13*j* are flowcharts illustrating a peak circle test algorithm for locating the pupillary aperture.
Figure 13J:
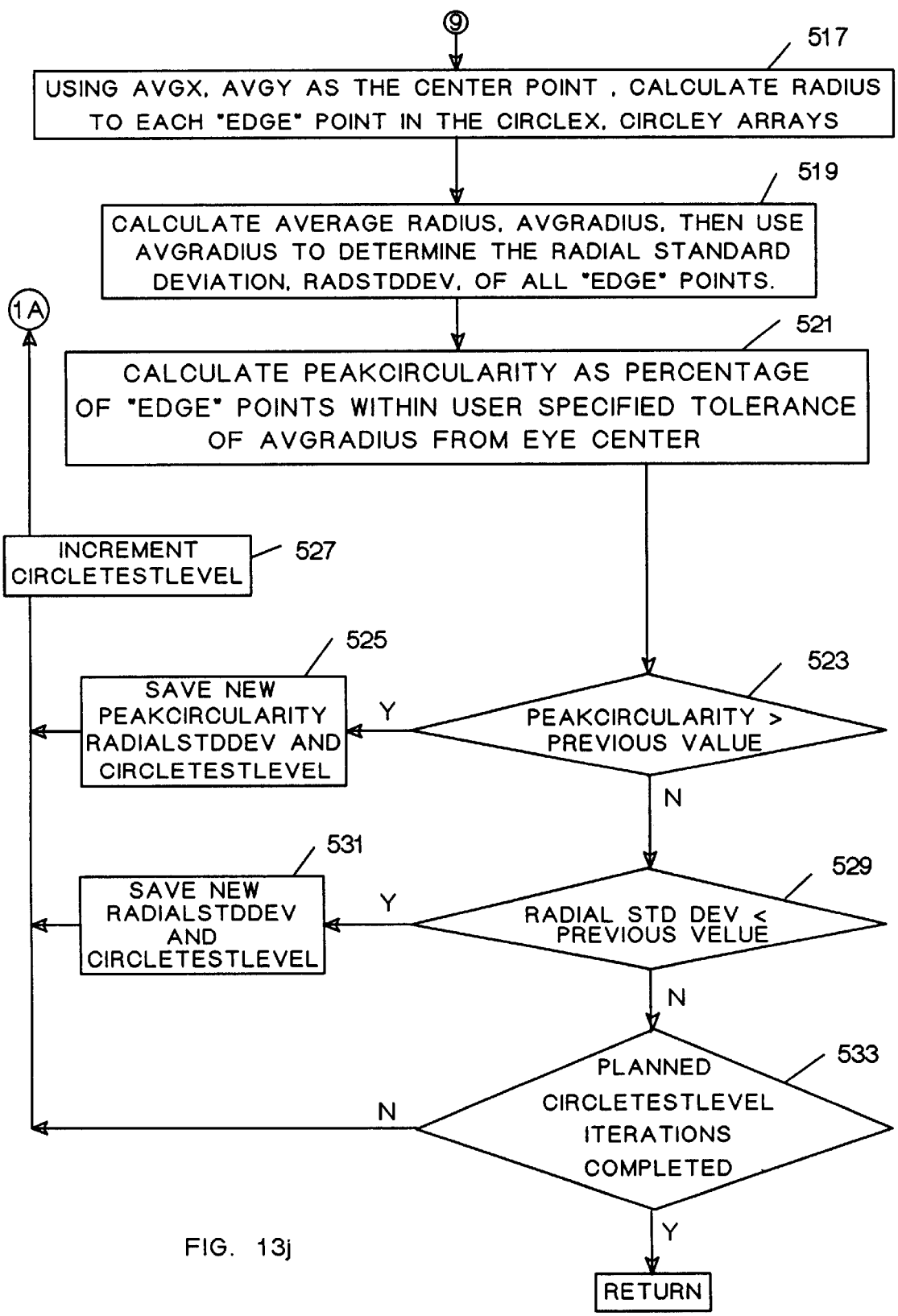

The peak circle test algorithm implements a fast running, novel technique for finding the intensity range of interest and then determining the circularity of the transition feature. The peak circle test algorithm exploits certain features in the intensity profile cross-section of typical eyes, as shown in FIG. 13h and the flowcharts of FIGS. 13i and 13j. The initial intensity value, CircleTestStartLevel, used for the peak circularity tests is determined within the peak circle test algorithm based upon sampling the intensity of a region of the eye at a given offset (64 pixels in the current embodiment), controlled via the RemControls.txt file, toward the nose from the location of the intensity peak being tested as a possible eye pupil location. For a true eye, the sample region should lie within the white, or sclera, portion of the eye. At boxes 505 and 507 of the flowchart of FIG. 13i, and using an intensity value, CircleTestLevel, set equal to this starting intensity value, and beginning at the coordinates (MaxPixX, MaxPixY) of the intensity peak for which Peak_Circle_Test was called, the Peak_Circle_Test algorithm tests the intensity value of each pixel in both horizontal directions at box 509 until it finds "edge" pixel locations on either side of the MaxPixX, MaxPixY location with intensity values less than the CircleTestStartLevel. If either "edges" is not found within a user-defined limit, presently 64 pixels, to either side of the MaxPixX,MaxPixY location, it is assumed that the starting level was too low. In this case, CircleTestLevel is incremented by one and the test is re-initiated at the higher intensity level.

After the initial "edge" locations have been found, another search is then initiated at box 511 wherein each pixel location, in the horizontal pixel row through the MaxPixX, MaxPixY pixel location, and between the "edge" pixel locations just described above, is used as a starting point for searches along the vertical pixel columns (upward and downward from each starting point) which determine the pixel locations ("edge" pixels) on each vertical column of pixels where the pixel intensity values fall below the CircleTestLevel. The locations of these "edge" pixels are saved into corresponding arrays CircleX and CircleY, for their x and y coordinates. Another set of searches is then performed at box 513, this time using the pixel locations in the vertical column of pixels through the MaxPixX,MaxPixY pixel as the starting points for searches in both horizontal directions (across the rows) to find the "edge" pixels where the pixel intensity value first falls below the CircleTestLevel. This search also uses the vertically highest (lowest row number) and vertically lowest (highest row number) from the preceding search to set the upper and lower limits on the aforementioned vertical column of pixels to be used for this search. Again, the coordinates of the "edge" pixels located by this search are stored as additional points in the same CircleX, CircleY arrays as before.

After the peak "edges," for the specified CircleTestLevel have been located by the horizontal and vertical searches described just above, the average horizontal (x) and vertical (y) positions are calculated at box 515 for the "edge" pixel locations stored in the CircleX, CircleY arrays and this value (AvgX, AvgY) is stored as the first estimate of the center location of the pupillary aperture. Using this (AvgX, AvgY) location as the assumed center at box 517, the radius to each of the edge points in the CircleX,CircleY is determined, an average radius is calculated, the radial standard deviation of the "edge" points is determined, and the percentage of "edge" points within the user specified tolerance about the average radius (i.e., the PeakCircularity) is calculated at boxes 519 and 521. In order to obtain the best estimate of center, and to address the possibility that the starting intensity level was too low, the value of CircleTestLevel is incremented by a user-defined amount and the tests above are repeated at boxes 523, 525 and 527 but now using the initial estimate of the pupil center (AvgX, AvgY) determined as above as the starting pixel location (instead of the MaxPixX,MaxPixY location). Up to 20 iterations of this process are conducted in the present embodiment (more or fewer iterations may be used) to help insure the relevant range of intensity values is covered. The best values of PeakCircularity, and secondarily the best value of the radial standard deviation, along with the corresponding average radius and the intensity level at which these best values were found at boxes 529 and 531, and are stored as the principal outputs of this subroutine, which ends at box 533 when the number of iterations is completed, as typically counted by a counter routine (not shown).

Figure 14:
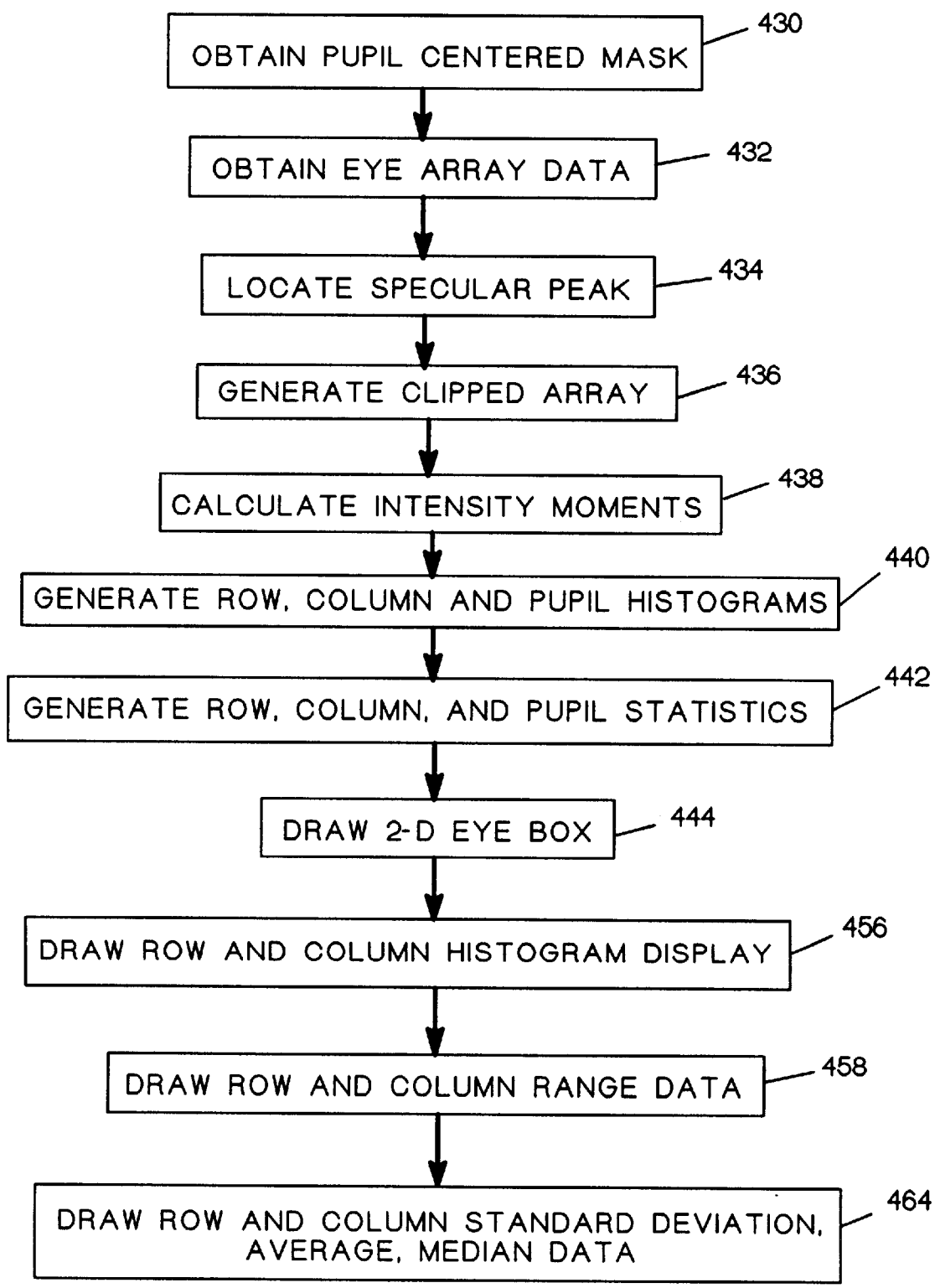
FIG. 14 is a flowchart of another embodiment of identifying and locating eyes of a subject.

Referring now to the flowchart of FIG. 14 and related drawings, after locating the eyes in the image generated by the reflex photometer of the referenced patent, or any other suitable reflex photometer, by one or more methods as described earlier, a pupil centered mask is generated by using the pupil radius from the peak circle test as described in the foregoing at box 430. The eye data, which may be an array of 128 by 128 pixels, as determined earlier by the FindEyes routine, and referred to herein as an eye array (or unclipped eye array), is selected at box 432 for further processing. This additional processing includes locating the specular peak indicative of the corneal reflection at box 434, creating a separate array, herein called a clipped eye array at box 436, wherein intensity values for pixels within the specular peak are replaced by pixel intensities representative of intensities associated with the retinal reflex as determined by interpolation of intensity values of pixels bordering the area of the specular peak as described in the foregoing. The clipped and unclipped eye arrays may then be subjected to further processing for determining various features and parameters for both the unclipped and the clipped arrays. The additional features and parameters include determining, for pixels within the pupillary aperture, (1) intensity moments for the specular peak itself, (2) intensity moments for the clipped array as shown at box 438, (3) pixel intensity histograms for each row and for each column of data within both the unclipped and clipped arrays (box 440), (4) other statistical parameters for each row and column including, in this embodiment, the range of intensity values, the average intensity, intensity standard deviation, and median intensity, for all pixels within the row or column, (5) a pupil intensity histogram at box 440 for all pixels within the pupillary aperture, (6) the range, average, standard deviation, and median intensities for all pixels within the pupillary aperture (box 442), and (7) the slopes, coefficients, and other parameters describing lines and curves which are determined from "curve fits" to the row-by-row and column-by-column average intensities (Box 442).

The specular peak is a region of high intensity values associated with the specular reflection of light generated by the light source within the reflex photometer of the subject invention, this peak being developed primarily by the tear film on the cornea as well as other surfaces (e.g., inner and outer surfaces of the cornea and of the lens) where the index of refraction changes. For each pixel within the specular peak, the total intensity recorded by the CCD camera is the intensity resulting from reflection of light from the retina through the pupillary aperture in addition to the specular reflection of light from the tear film and other surfaces of the cornea and lens.

Due to the difference in curvature of the cornea from the curvature of the rest of the eyeball, and the fact that the center of rotation for eye movements, as in changes of direction of view and fixation, is close to the center of curvature of the eyeball rather than the center of curvature of the cornea, in images generated by the instant invention, the location of the peak due to specular reflection shifts relative to the "geometric center" of the pupil as the viewing direction or point of fixation of the eye changes. This relative shift of the location of the specular peak may be exploited to help determine whether the binocular alignment of the eyes is normal or abnormal.

This relative shift of the location of the specular peak relative to the "geometric center" of the pupillary aperture is exploited in at least two methods as disclosed herein. The first method supports the automated processing and analysis of data to help determine the clinical conditions of eyes, and the second method supports the display presentation of eye image data in a manner which assists an untrained observer in recognizing abnormal eye conditions. Here, the "geometric center" of the pupillary aperture is defined as the center of a circle which encompasses the pupillary aperture in a "best fit" sense, with a radius approximating the radius of the pupillary aperture, as determined from the peak circularity test algorithm or the Hough transform as described above.

During processing, a search for the pixel of highest intensity is made within rectangular bounds, controlled by user inputs, centered on the estimate of the geometric center of the pupil determined as noted above. The highest pixel intensity value found within this rectangular search region is assumed to be associated with the specular peak. In the present embodiment, the boundary of the area of the specular peak (the regions where the pixel intensities are due primarily to the light reflected from the retina with little or no intensity contribution resulting from corneal reflections) are estimated by a sliding window sum of multiple pixels in several directions from the location of this pixel of highest intensity. The boundary of the area encompassing the specular peak in each direction is estimated as the center point of the sliding window sum where the sum exceeds some user controlled percentage Of the previous sum (progressing outwardly from the highest pixel), indicating a transition from the peak to flatter intensity regions. Once the edges of the specular peak has been determined thusly in four or more directions from the central peak, then two dimensional interpolations or spline fits or similar techniques may be used to estimate, for pixels within the area of the specular peak, their intensities based on light reflected from the retina as opposed to light reflected from the cornea. Pixel intensity values based on such interpolations are used to create the clipped array wherein the intensities of pixels within the specular peak are replaced with intensity values, interpolated or otherwise estimated, more representative of intensities reflected from the retina rather than the cornea. Values from this clipped array are then used in some of the additional processing to avoid undue influence of the intensities from the specular peak on other calculated parameters (e.g., intensity moments of the reflected light patterns associated with refractive errors, outputs from Fourier and other transforms).

In the present embodiment, the intensity moments of the specular peak are determined in three different ways. Using a Cartesian coordinate system centered on the geometric center of the pupillary aperture, the intensity moment of the pixel of highest intensity in the specular peak is calculated about the x and y axes respectively, as the pixel intensity times the distance, in pixels, from the x and y axes, respectively. Another moment, called the total intensity moment, about each of the x-axis and the y-axis, is calculated as the sum, for all the pixels within the area of the specular peak, of the products of the their respective total intensities times their distances from the x-axis and y-axis, respectively. The x and y coordinates of the center of total intensity are calculated by dividing the moments about the x and y axes, respectively, by the total intensity of all pixels within the area of the specular peak. A similar set of calculations are performed to determine moments about the x and y axes and the center of intensity based on the difference, for each pixel within the area of the specular peak, of the original intensity of the pixel minus the intensity of its corresponding pixel in the clipped array. The intensity moments and centers of intensity calculated as above correlate with the eye conditions such as esotropia and exotropia which result from an inability to point and fix both eyes on the same subject at the same time.

Additional sets of intensity moments are calculated based on the intensities of all the pixels, and subsets of pixels, for pixels within the pupillary aperture in the clipped array. Again, one set of moments are based on the total intensity for each pixel under consideration, and another set of moments are based on the difference of the total intensity for each pixel and some reference level (being in the present embodiment the average intensity of pixels in the iris region). These moments calculated from the clipped array correlate with the refractive states of the eye (e.g., normal, hyperopia, myopia).

Intensity histograms, for pixels within the pupillary aperture are then calculated for each row and subsequently for each column in both the unclipped and clipped arrays using an innovative, fast running, histogram algorithm. The histogram algorithm divides the intensity of each pixel by a user input quantity, which may be a power of 2 to minimize computational time, and then uses the result of this division as a pointer to indicate which "bin" in the histogram array should be incremented to reflect the addition of another pixel within its range. A logical mask (circular in the present embodiment with radius determined using the average radius from peak circle test) is used to determine which pixels within the row or column is also within the pupillary aperture.

For each row, and subsequently for each column, in both the unclipped and the clipped histogram array, the range of pixel intensity values, the average intensity, the standard deviation of the intensity, and the median intensity is conventionally determined for pixels which are also within the pupillary aperture.

The determination of which pixels are within the pupillary aperture (and therefore to be included in the row-by-row, or column-by-column histograms) is made based on the use of a circular mask. The center of the mask is located at the geometric center of the eye, determined as described above (e.g. by the peak circle test method of the FindEyes program, by use of a Hough transform, or other such method, as should be apparent to those skilled in the art), and the radius of the mask is established as a user controllable offset (typically two to three pixels) from the radius of the pupillary aperture as also returned by the peak circle test algorithms.

Additional histograms are generated for both the unclipped and clipped arrays based on all the pixels within the pupillary aperture. Additionally, the intensity range, average intensity, standard deviation of intensity, and the median intensity level are determined based on all pixels within the pupillary aperture. The distribution of light intensities within the pupillary aperture as indicated by the pupillary histogram is related to the uniformity of light received by the subject instrument which in turn is related to the uniformity of light transmission and reflection through the optical path of the eye. The uniformity of light transmission is affected by clinical conditions such as cataract and possibly by macular degeneration.

In addition to providing value in correlating image analysis parameters with the clinical status (abnormal or diseased conditions) in an automated processing and statistical correlation system, several of the parameters calculated above have also been incorporated into an innovative display which permits an observer to readily determine several clinical conditions, including abnormal refractive conditions (e.g., myopia or hyperopia), abnormal binocular fixation and alignment conditions (e.g., esotropia, exotropia), and other conditions associated with abnormal transmission of light through the optical path of the eye, such as a cataract or foreign object. Here, color encoding of the pixel intensity values for pixels in a region surrounding each eye, which may be the 128×128 pixel array described above, is used to generate at box 444 (FIG. 14) a 2-dimensional view 446 (FIG. 14*a*) of each eye, and herein called a 2-D eye box for each eye, with the pixel intensity patterns for each eye enhanced for viewing by the assignment of different colors to different intensity levels, resulting in easily discernable intensity contours and patterns. Separate 2-D eye boxes 446 are created side-by-side on the viewing screen with, in the present embodiment, a color scale bar 448 between the two boxes for indicating the order of assignment of colors to intensity levels. Since the pixels presented within the 2-D eye box for each array were selected to evenly surround the estimated geometric center of each eye as determined by the peak circle test algorithm described earlier, the estimated geometric center for each eye is placed within one pixel of the center of the 2-D box. Small tic marks 450 are added to outer and lower sides of the 2-D eye boxes to provide an additional visual reference for the geometric center of the box (and of the eye).

In the present embodiment, additional boxes 452 (herein called row histogram boxes) of the same size as the 2-D eye boxes are placed to either side of the 2-D eye boxes and other boxes 454 (called column histogram boxes) are placed vertically below each 2-D eye box for presentation of data from the row-by-row and column-by-column histogram and statistical analyses described above, respectively. Several display formats may be presented within these boxes, with the user being able to successively advance from one display format to the next format using the keyboard, mouse, or similar control mechanism.

Figure 14A:
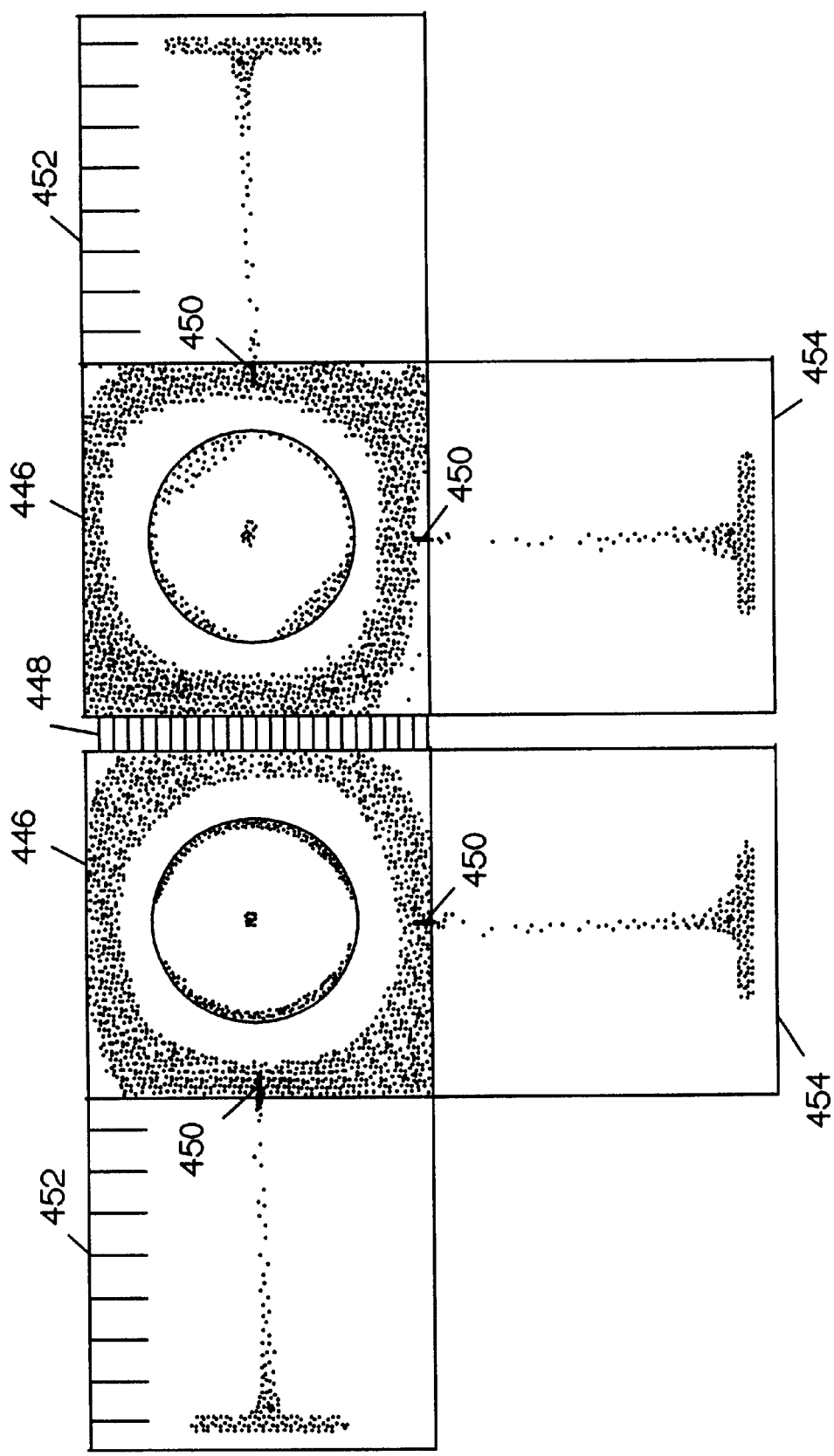
FIGS. 14*a*, 14*b*, and 14*c* are color graphic illustrations relating to particulars of the method of FIG. 14.

In one display format as shown in FIG. 14*a*, the row-by-row histogram data and the column-by-column histogram data are developed at box 456 of FIG. 14 and displayed as follows. For the row histogram boxes to either side of the 2-D eye boxes, the horizontal scale represents intensity levels, with the intensity level in each box increasing toward the 2-D boxes in the center of the screen, i.e., normal left to right increase in intensity for the leftmost box, but a right to left increasing intensity scale in the rightmost box. The rows in the row histogram boxes correspond to the rows in the 2-D eye boxes. For each row in the row histogram display, if the histogram array element (i.e., histogram bin) corresponding to a given intensity range is of a value greater than zero (indicating at least one pixel with the corresponding intensity level within the row), then the corresponding pixel in the corresponding row in the row histogram display is assigned the same color, corresponding to the intensity level, as used for the intensity level in the 2-D eye box. The resulting display is, in essence, a side-on view of the same intensity values as presented in the 2-D eye box for the corresponding eye, thereby making it easier to interpret the color contours presented within the 2-D eye boxes. A similar display is presented within the column histogram boxes drawn below the 2D eye boxes, but with the intensity scale increasing vertically upward (toward the 2-D eye boxes) for both column histogram boxes.

Figure 14B:
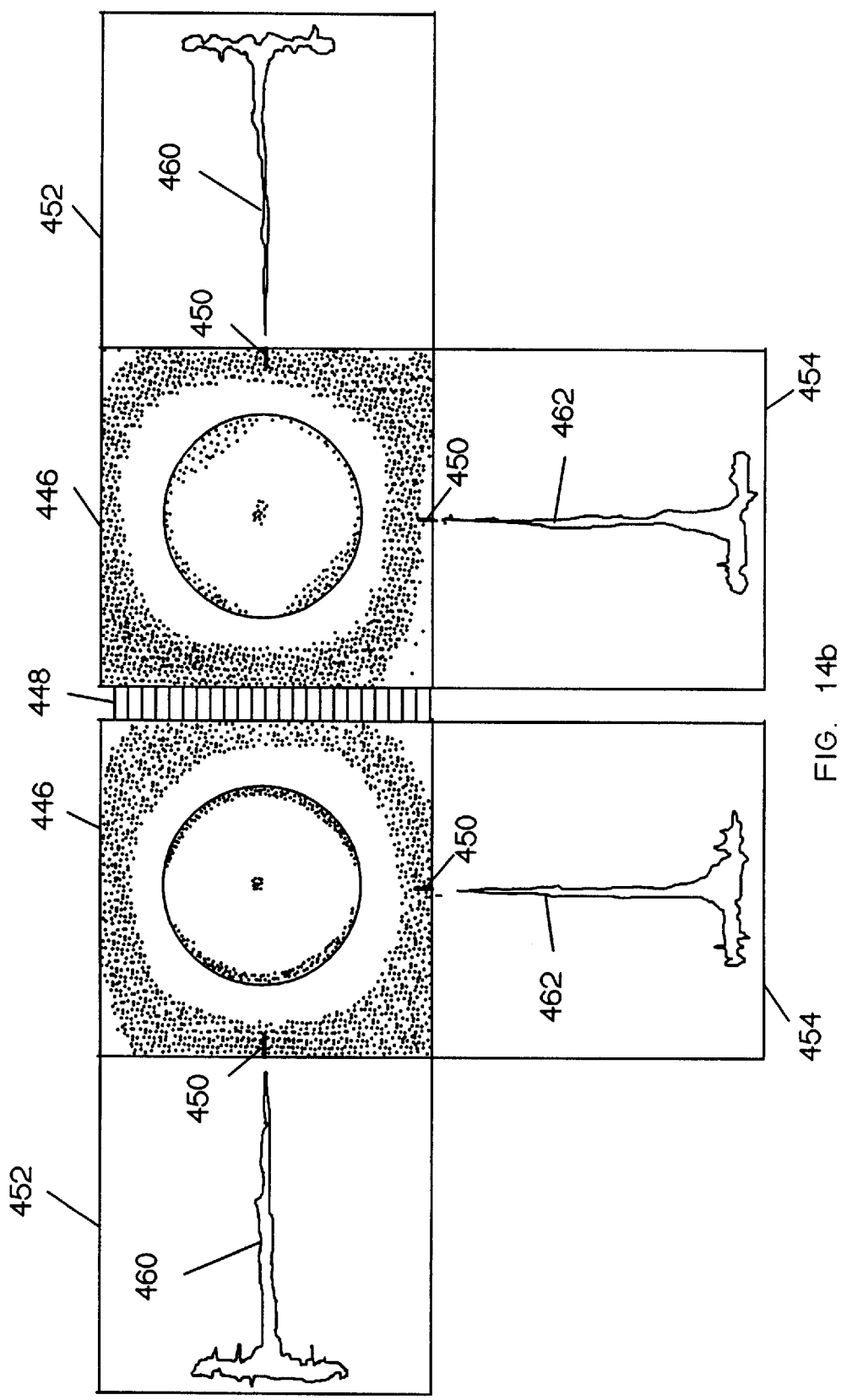

In another display format, as shown in FIG. 14*b*, the same background format is used as before for the row histogram boxes (i.e., horizontal intensity scale and rows corresponding to rows in the 2-D eye boxes), but in this display {a continuous color bar, using a color (dull green in the present implementation) different from the background color for the box (dull red in the present implementation), is drawn between the maximum and minimum intensity values for each row (box 458 of FIG. 14), thus representing the range of intensity values present within that row of data. This has the effect of outlining an envelope 460 defined by the range of intensities of each row. Similar displays 462 are presented in the column histogram boxes 454 below the 2-D eye boxes. These displays make it easy to immediately see the range of intensity values for each row or column of pixels within the pupillary aperture, and to also see the relative alignment of the specular peak with the geometric center of the eye, as described below.

For the scales, intensity bin sizes, and offsets presently used with the reflex photometer of the instant invention, the display of the range of values 460 and 462 for the specular peaking this display format, takes on the appearance and nature of a pointer, showing the relative alignment of the specular peak for each eye with the geometric center of the eye as indicated in the adjacent 2-D eye box by the aforementioned tic marks placed on the edges of the 2-D eye box to represent the geometric center of the pupillary aperture. This display format thereby provides a ready visual reference of the relative vertical alignment of the specular peak for each eye relative to the geometric center for the same eye as well as a visual reference of the corresponding position of the specular peaks, and relative vertical alignment and fixation, between the left and right eye. The intensity range for each column of pixels is presented in a similar format in the column histogram box just below and adjacent to the 2-D eye box for each eye. This display, in conjunction with the tic marks in the bottom edge of the 2-D eye boxes representing the horizontal center of the pupillary aperture for each eye, provides a relative visual reference for the horizontal alignment and fixation for each eye.

In the same display as described, for a normal eye, the range of intensity values, for each individual row is generally smaller than for eyes which have a refractive error or other abnormalities. Additionally, for normal eyes, the range of intensity values from row to row is similar, so that in the row histogram boxes, the signature for normal eyes takes on the appearance of a "T" on its side, with the base of the "T" pointed toward the center of the eye as shown in the corresponding 2-D eye box. For this aforementioned "T" on its side" display, a deviation from vertical of the nominally vertical cross-bar of the "T" is generally an indication of a refractive error in the eye, and a broadening in the thickness of this "T" crossbar generally corresponds to presence of a refractive error, a cataract, or a combination of abnormal conditions. In the similar display of the column-by-column histogram data, the "signature" for a normal eye is an inverted "T," with the base of the "T" pointing upward toward the 2-D eye box, and the crossbar of the "T" positioned horizontally below the upwardly pointing base of the "T." As before, deviations in the slope and thickness of the crossbar of the "T" are indicators of refractive error or cataracts or other abnormal conditions, respectively.

Figure 14C:
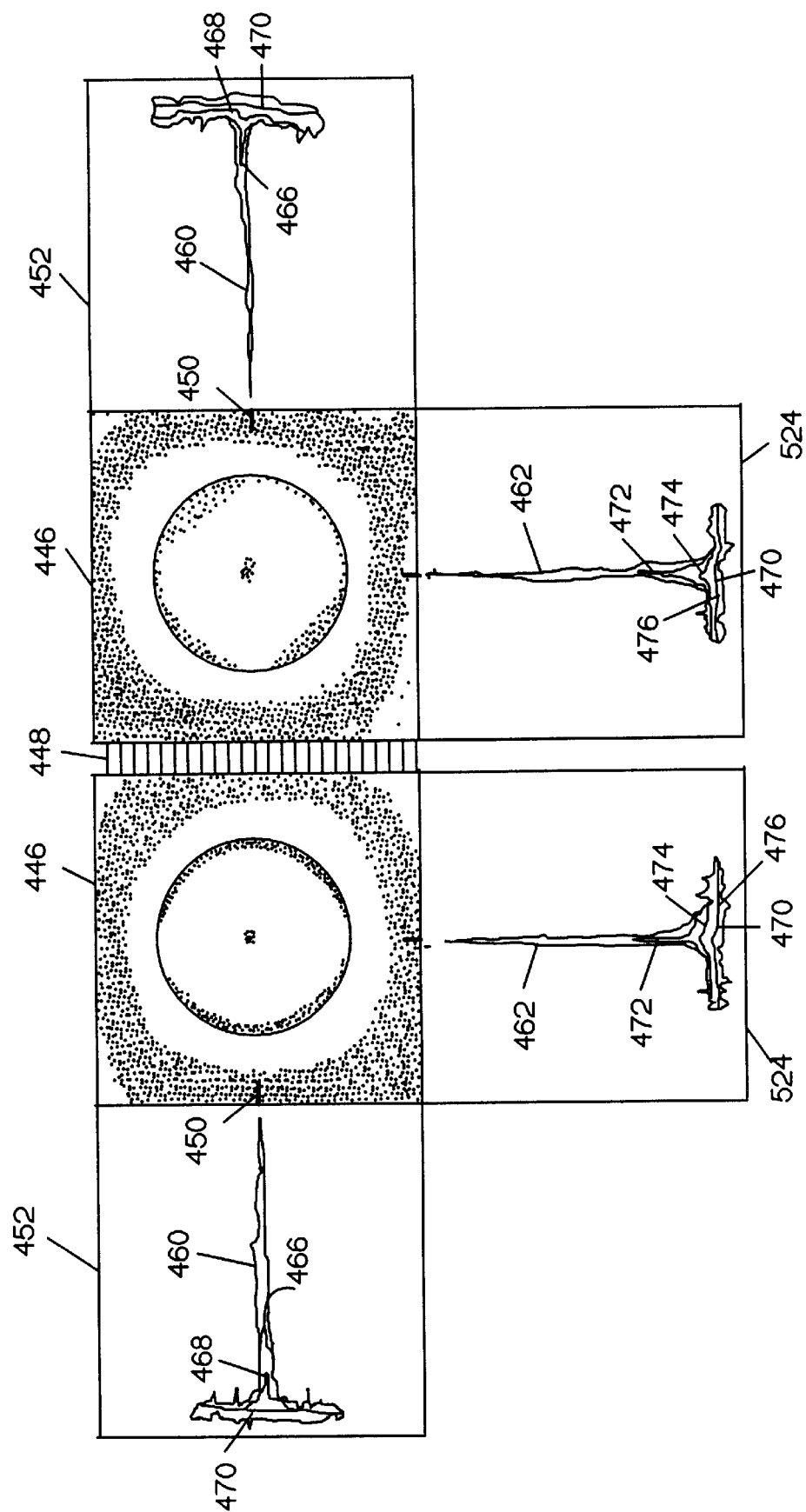

In a related modified version of the display just described, and referring now to FIG. 14*c*, the standard deviation of the range of intensities about the average intensity for each row is drawn at box 464 of FIG. 14 in a different color (yellow in the present implementation, and which appears at 466 generally in the crossbar region of the "T" earlier described) on top of the row intensity range display just described. Then, the average intensity for each row is added to the display by drawing a line 468 (bright red in the present implementation) connecting the pixels corresponding (on the aforementioned horizontal scale) to the average intensity value for each row. Similarly, a line 470 is added in a different color (blue in the present implementation) connecting the points representing the median intensity for each row. This modified display provides enhanced visual feedback related to the variation of intensity values across each row of pixels in the pupillary aperture, as well as the general slope or shape of the line or curve connecting the average intensity points for each row. Similar and corresponding modifications 472, 474, 470 are made to the displays of the column histograms and statistics in the aforementioned column histogram boxes 524 below the 2-D eye boxes described earlier.

With the addition of the color representing the standard deviation of the intensity values for pixels in the pupillary aperture for each row, the modified display now takes on the appearance, for a normal eye, of a sword, with the point of the sword pointing generally toward the center of the eye in the adjacent 2-D eye box, corresponding to the base of the "T" as described earlier, and the hilt of the "sword" corresponding to the crossbars in the "T" as also described earlier. The apparent "handle" of the "sword" results from the extension of the standard deviation in the rows containing the specular peak, so that the color range associated with the standard deviation in the rows containing the specular peak extends typically below the true range of intensity values for the same rows, thereby providing the "handle" for the sword. For a normal eye, the characteristic or signature display is that of a symmetric sword with a relatively thin "hilt" perpendicular to the blade of the sword. Tilting of the hilt from being perpendicular to the blade of the sword is an indicator of a refractive error in the eye (e.g., hyperopia or myopia) and an increase in the thickness of the hilt can be an indicator of cataract or other abnormal conditions in addition to refractive errors. Significant misalignment between the point of the sword and the tic marks representing the geometric center of the eye can be an indicator of an abnormal binocular alignment or fixation problem between the eyes (e.g., esotropia or exotropia). Shifts in the relative position of the hilt along the length of the sword may be indicative of abnormal obstruction of light transmission into and out of the eye.

Figure 15:
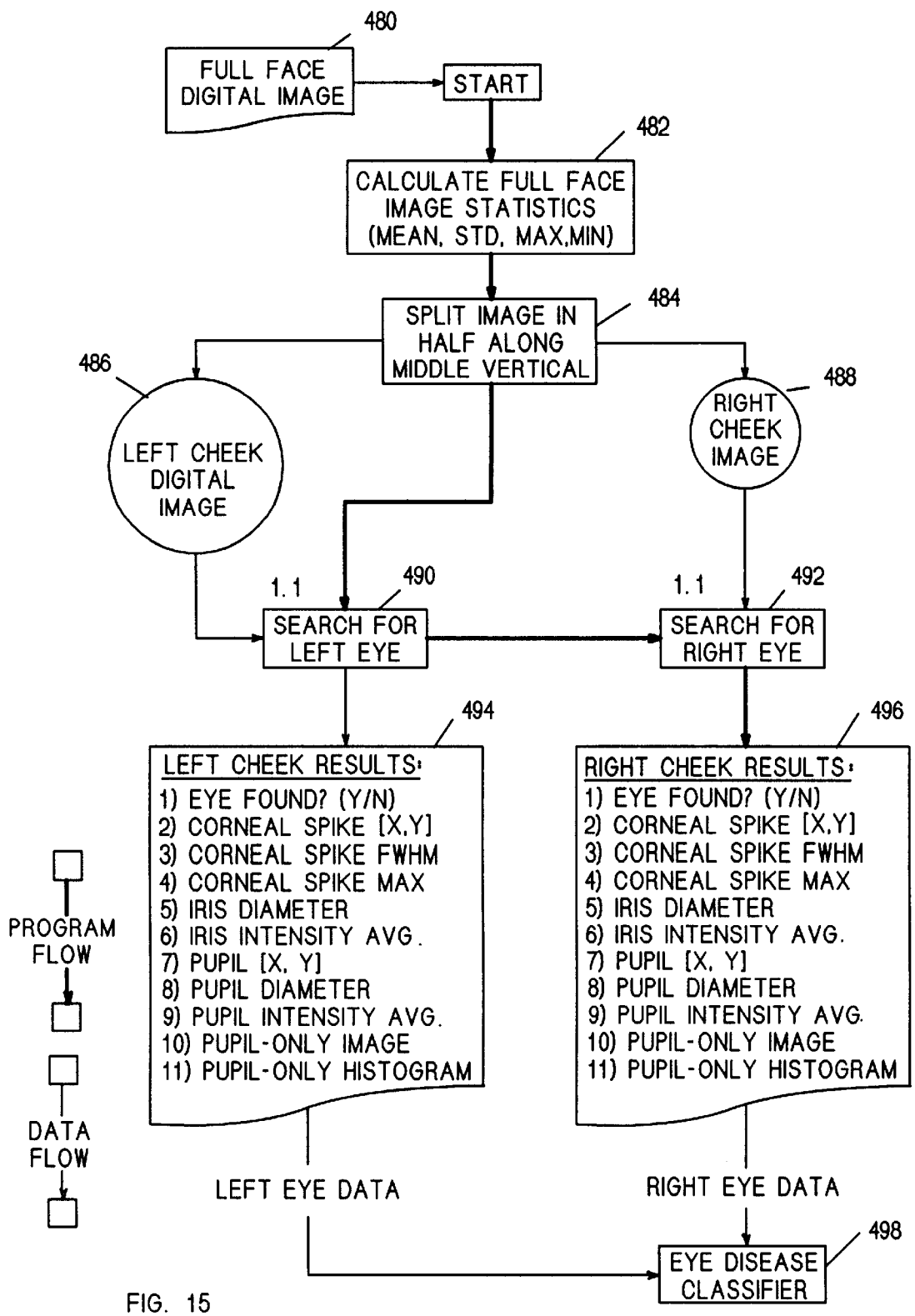
FIG. 15 is a high level flowchart of yet another method for identifying and locating eyes of a subject.

In yet another method for locating the eye, reference is made to the flowcharts and associated drawings beginning with FIG. 15. In these flowcharts, data is represented as being in circles, with data flow designated by thin lines. Descriptions of the program are represented in rectangular or other conventionally shaped boxes, with program flow being connected by thicker lines. Additionally, to assist in tracing interconnections of the flowcharts, further delineations of boxes in a higher level flowchart are designated by a series of numbers, with the delineated, lower level flowchart being headed by the designated number. For instance, in FIG. 1 boxes 490 and 492 are also labeled 1.1, indicating that the processes of these boxes are further described in the flowchart headed by 1.1 (FIG. 15*a*).

Initially, FIG. 15 is a high level flowchart of an embodiment wherein at box 480 a full face digital image from the camera is parsed into computer memory. At box 482 certain full face image parameters are calculated, these parameters including mean and standard deviation of intensity values, and maximum and minimum intensity values registered by pixels in the full face array. At box 484 the full face image is divided vertically to develop half face images 486 and 488 as shown and described for FIG. 1*a* so that each half of the full face image contains one of the eyes of a subject. At boxes 490 and 492 a search algorithm is employed to locate the left and right eyes, this algorithm being the same for both eyes and beginning with the left eye. At boxes 494 and 496 a number of parameters are provided as outputs from boxes 490 and 496, these parameters to be provided to an eye disease classifier 498, which is beyond the scope of this disclosure. Additionally, the data calculated at boxes 494 and 496 may be used in conjunction with any of the graphical displays described above.

Figure 15A:
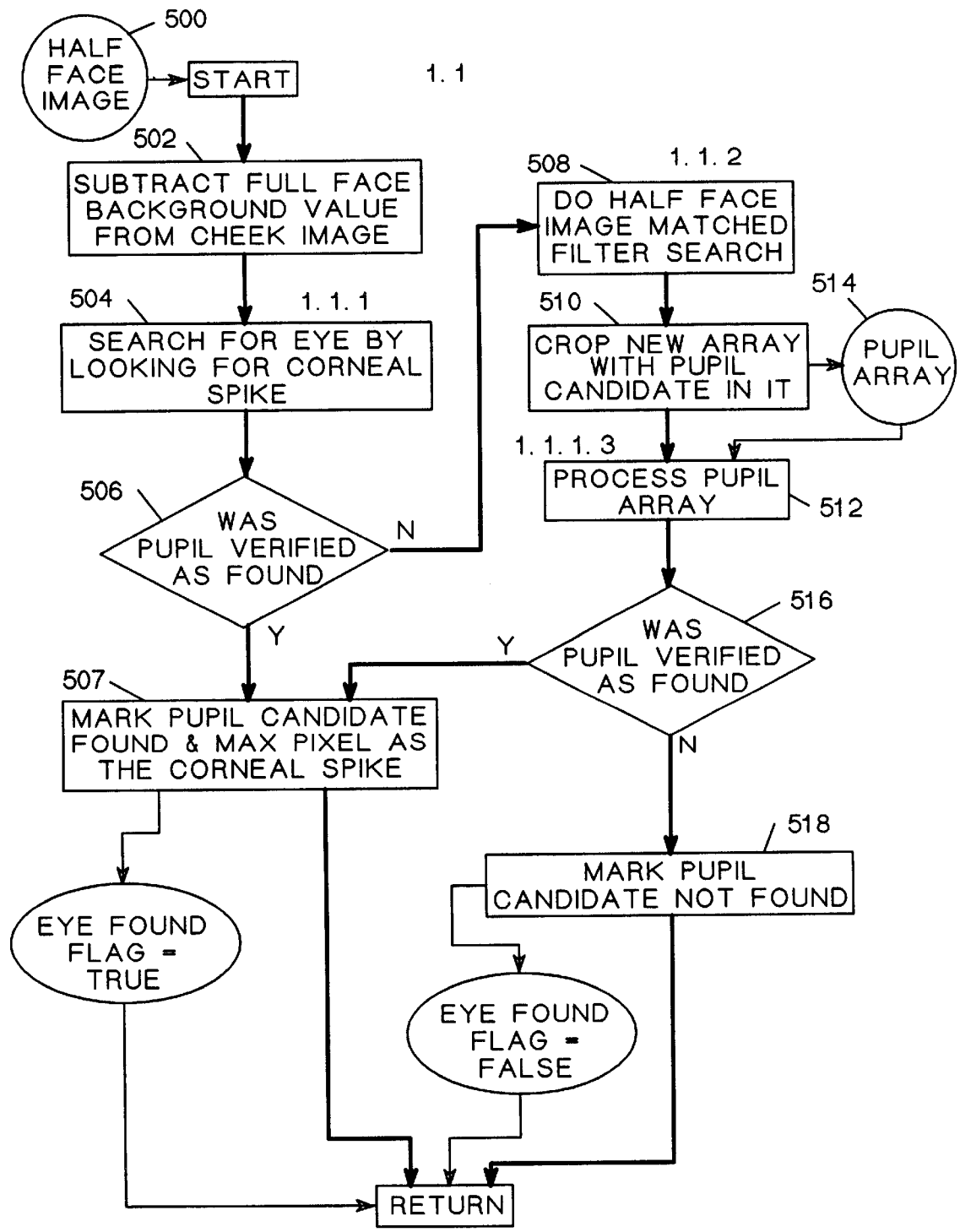
FIG. 15*a* is a flowchart illustrating a portion of the flowchart of FIG. 15 wherein a pupil is located.

Turning now to the flowchart of FIG. 15*a,* a flowchart for locating the eyes at boxes 490 and 492 of FIG. 15 is shown. Initially, the half face image is provided at box 500, and at box 502 background noise, or a bias value representative of the "dark frame" image described above, is subtracted from the half face image to eliminate components of the "dark frame" image from the face image. Next, at box 504 attempts are made to locate the pupil of the eye by identification and analysis of the corneal spike. At box 506 the inquiry is made as to whether or not the pupil was located at box 504, and the program takes one of two branches depending on the outcome of the inquiry. If the pupil was located, then a flag is set at box 507 indicating that the pupil was found, the pupil array and maximum intensity pixel in the corneal spike is stored and the program returns to a respective one of boxes 494 and 496 of FIG. 1. As noted by the data flow lines in FIG. 15, attempts are made to locate the left pupil first and then the right pupil, although the reverse order may also be used. In a parallel processor or process, the search for both pupils may occur simultaneously.

Where analysis of the corneal spike did not result in locating the pupils, then a matched filter search of the half face image for a pupil is done at box 508, as will be further explained. Where a candidate pupil is located at box 508, then the candidate pupil is cropped from the half face array in a 96 by 96 square array at box 510, the array stored at box 514 and at box 512 processing of the 96 by 96 array is done to verify whether a valid pupil was located. At box 516 an inquiry is made as to whether the pupil was verified, and if so then the program returns via box 507 to a respective one of boxes 490 or 492 of FIG. 15. If the pupil is verified as not found at box 516 then a flag indicating the pupil was not found is set at box 518, and the program exits to either box 494 or 496 of FIG. 15 where values or flags of the parameters of these boxes are set to default values. As such, at boxes 494 and 496 the EYE FOUND flag will be set to NO, the corneal spike X, Y coordinates will be set to 0,0, the corneal spike half maximum value will be 0, etc. The path of boxes 502–507 is tried first because it is less computationally intensive, and locates the pupil in most instances. Where the pupil is not located by the process of boxes 502–507, then the process of boxes 508–516 is used, which more reliably locates the pupil but is more computationally intensive.

Figure 15B:
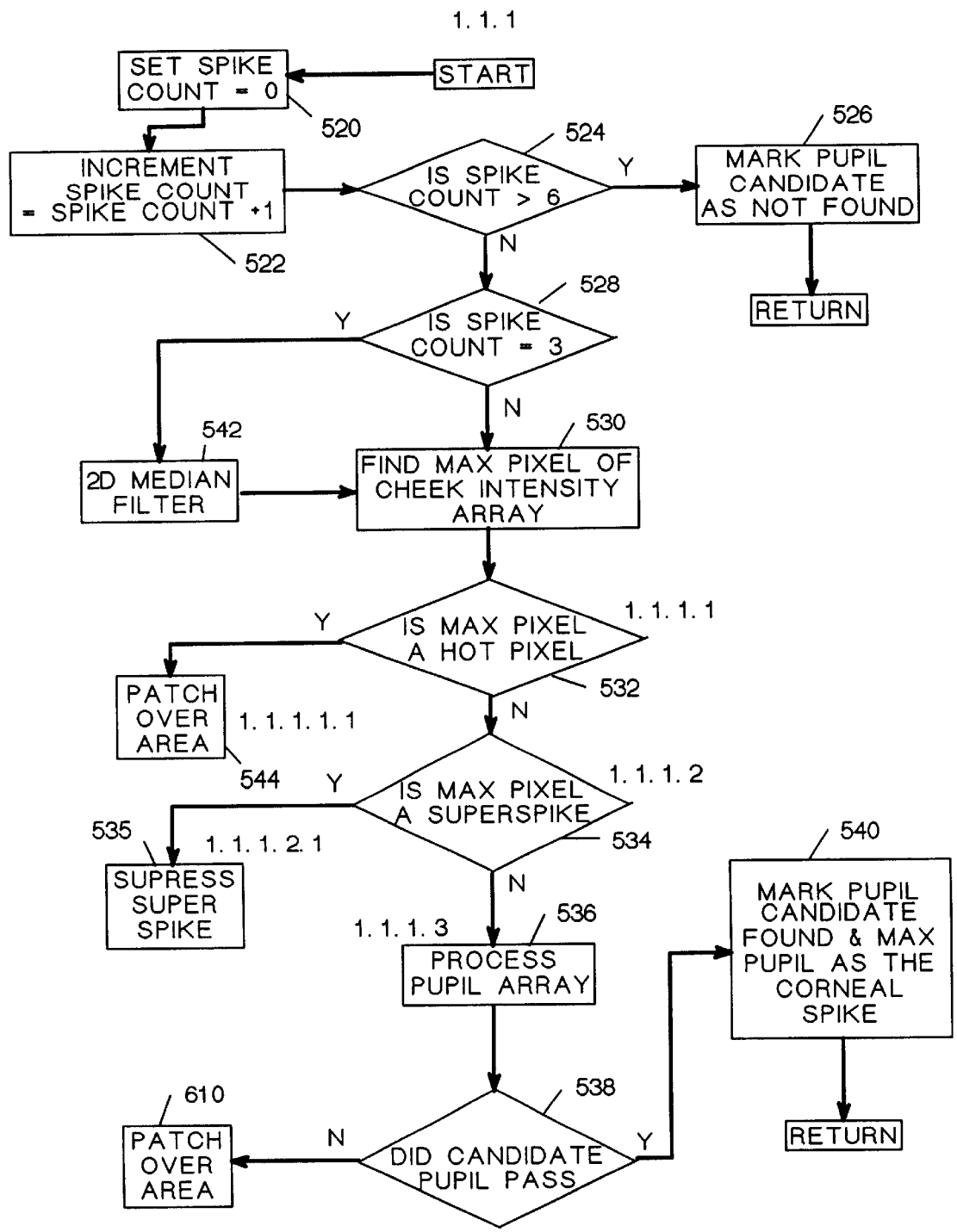
FIG. 15*b* is a flowchart illustrating a method for analyzing high intensity spikes in a search for a corneal spike.

The flowchart of FIG. 15*b* illustrates the process of box 504 of FIG. 15*a* wherein the attempt is made to locate the pupil by finding the corneal spike. This analysis is essentially a loop wherein a maximum of six spikes are examined for characteristics of a corneal spike, with a spike registering a highest intensity being tested first. As such, where a determination has been made that a spike is not the corneal spike, then the program eliminates the tested spike from further consideration and moves on to test the next highest intensity spike. Thus, in FIG. 15*b,* and initially during the process, a spike counter is initialized to 0 at box 520, and incremented to a 1 at box 522 where the loop is entered. Alternately, the loop may be entered with the spike counter initialized to 0 and incremented by one at each iteration of the loop. At box 524 the inquiry is made as to whether the count is greater than 6, indicating that 6 corneal spikes have been tested without finding the pupil. At this point, the program exits from box 526 to box 506 of FIG. 15*a,* where a more robust, but more computationally intensive, examination of the array is undertaken. While 6 attempts are made in this embodiment to locate the pupil, the pupil is usually found after 2–4 attempts. If the answer at box 524 is NO, indicating that less than 6 spikes have been tested, then the program flow is directed to box 528, where the inquiry is made as to whether the spike counter has reached a count of 3. Where the answer here is NO, then the program falls through to box 530 where the maximum intensity pixel is found in the array. This highest intensity pixel is tested at box 532, as will be further explained, as to whether it is a "hot" pixel, i.e. a malfunctioning pixel registering an inappropriately high intensity level, and if not then at box 534 the test is made as to whether the selected pixel is a "super spike" pixel, such as a spike developed from eyeglasses, a tear duct, etc. Where the spike is determined to be a superspike, then at box 535 the superspike is clipped, as will be further explained. If the answer to the test of box 534 is NO, then the program conducts the pupil matched filter test at box 536 wherein an iris-sized array is cropped, which in this instance is 96 y 96 pixels square, around the selected highest intensity pixel and performs a pupil matched filter test on this subarray in an attempt to locate a pupil. At box 538 the inquiry is made as to whether the pupil was verified as being located, and if so then the program proceeds to box 540, where the subarray is marked as containing the pupil and the maximum intensity pixel is marked as being the corneal spike. If, at box 538 the pupil matched filter indicated that the selected spike was not a corneal spike, then the answer at box 538 is NO, and the program patches over the spike as described above, eliminating that spike from further consideration. After patching the spike, the program loops back to box 522, where the spike counter is incremented by one, and the program proceeds once more to select the next highest intensity spike remaining in the half face image for consideration as to whether that spike is the corneal spike.

If the corneal spike has not been located during the first and second loops, then on the third loop, the answer at box 528 is YES, and the program proceeds to box 542 where a two dimensional median filter array is applied to the half face image. Such a filter may be found in MATLAB5 in the Image Processing Toolbox portion, the function titled MEDFILT2. This filter has the effect of a nonlinear low pass filter that lowers isolated pixels that are excessively higher in intensity than an average intensity in the half face array, affording a greater chance of locating the pupil during the following loops of the program.

Figure 15C:
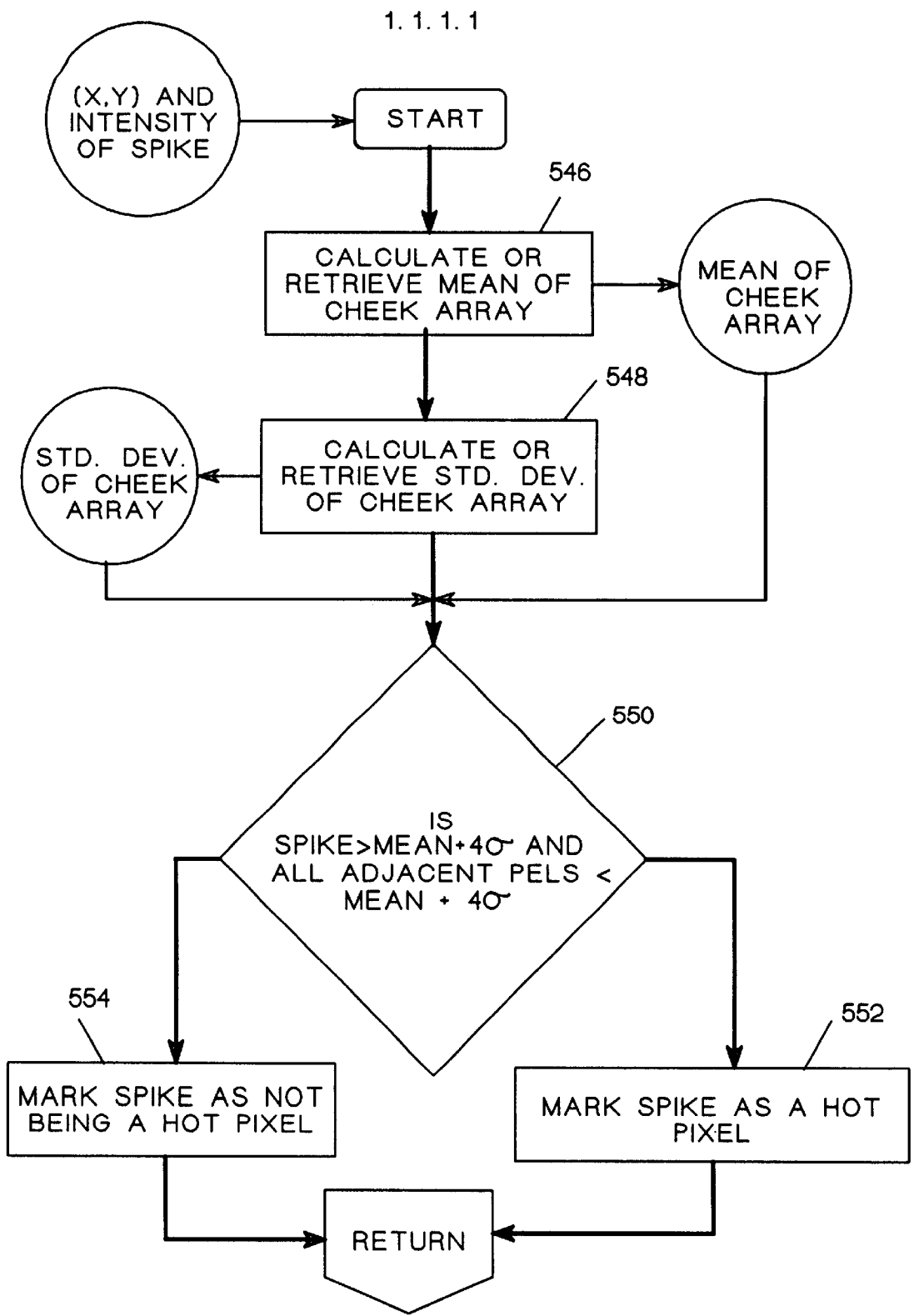
FIGS. 15*c*, 15*d*, 15*e*, 15*f* and 15*g* are flowcharts illustrating particulars of the flowchart of FIG. 15*b*.
Figure 15D:
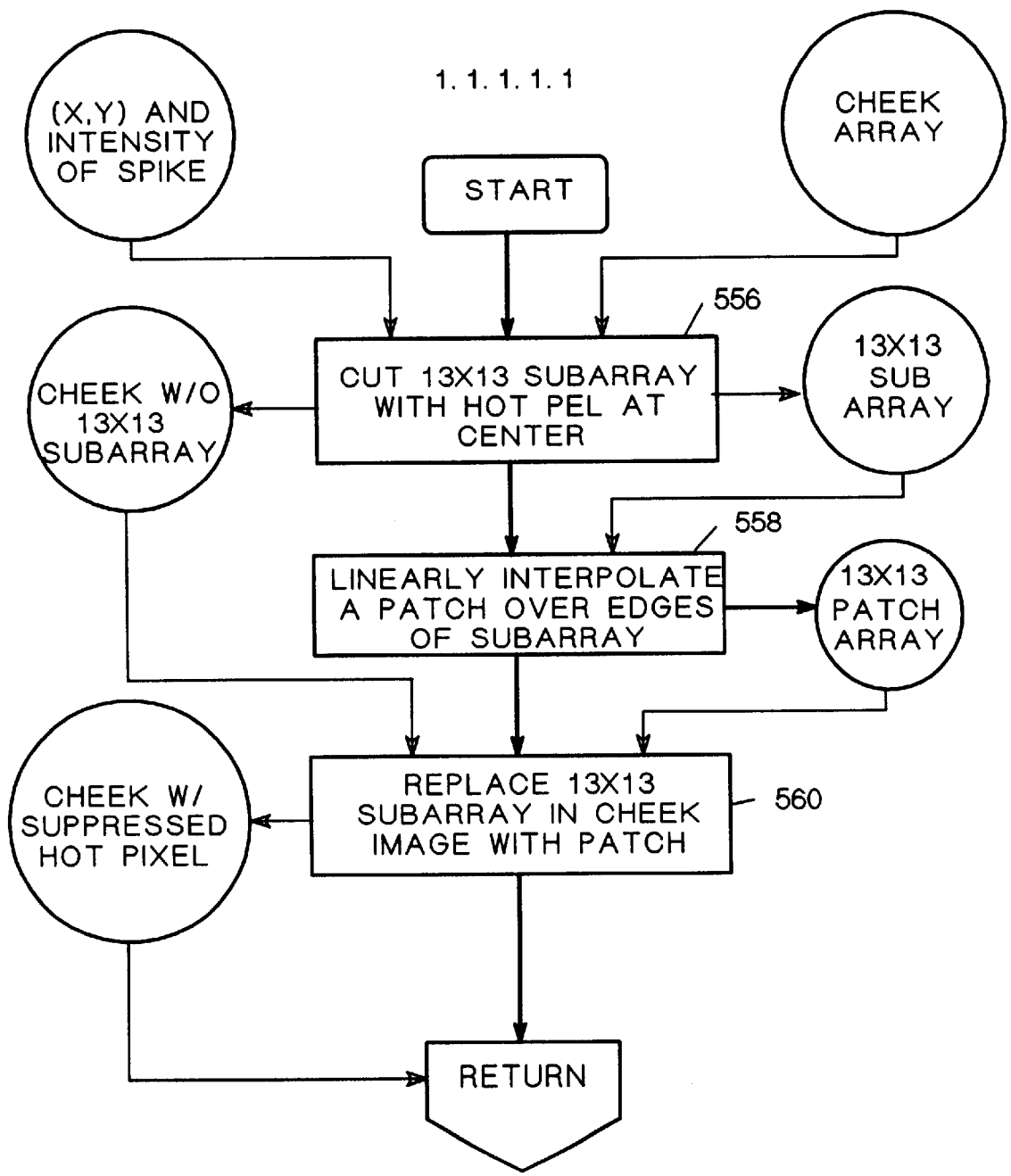

The "hot pixel" test at box 532, which determines whether or not a pixel under consideration is a hot pixel, is shown in greater detail in the flowchart of FIG. 15c. Here, at boxes 546 and 548, the mean and standard deviation of intensity values in the original half face array are calculated, or retrieved if they were earlier calculated. The question is then asked at box 550 whether the intensity of the selected pixel is greater than the mean plus 4 standard deviations and whether all the adjacent pixels to the selected pixel are all less than the mean plus 4 standard deviations. While 4 standard deviations has been determined through experimentation to work well, a range of from about 2.5 to 4.5 standard deviations would probably be adequate. Depending on the outcome of this test, the pixel is marked as a hot pixel at box 552 or not a hot pixel at box 554, and the program returns to box 544 (FIG. 15b) where a patch such as the 13 by 13 linearly interpolated patch as shown and described for FIG. 3c is placed over the area containing the hot pixel. This patching process is again shown in the flowchart of FIG. 15d, where at box 556 a small subarray, such as a 13 by 13 pixel subarray, is centered on the pixel of interest, the hottest pixel, and at box 558 a patch is linearly interpolated over the edge pixels. The intensity values of pixels in the 13 by 13 array are then replaced by the interpolated values, as shown at box 560.

Figure 15E:
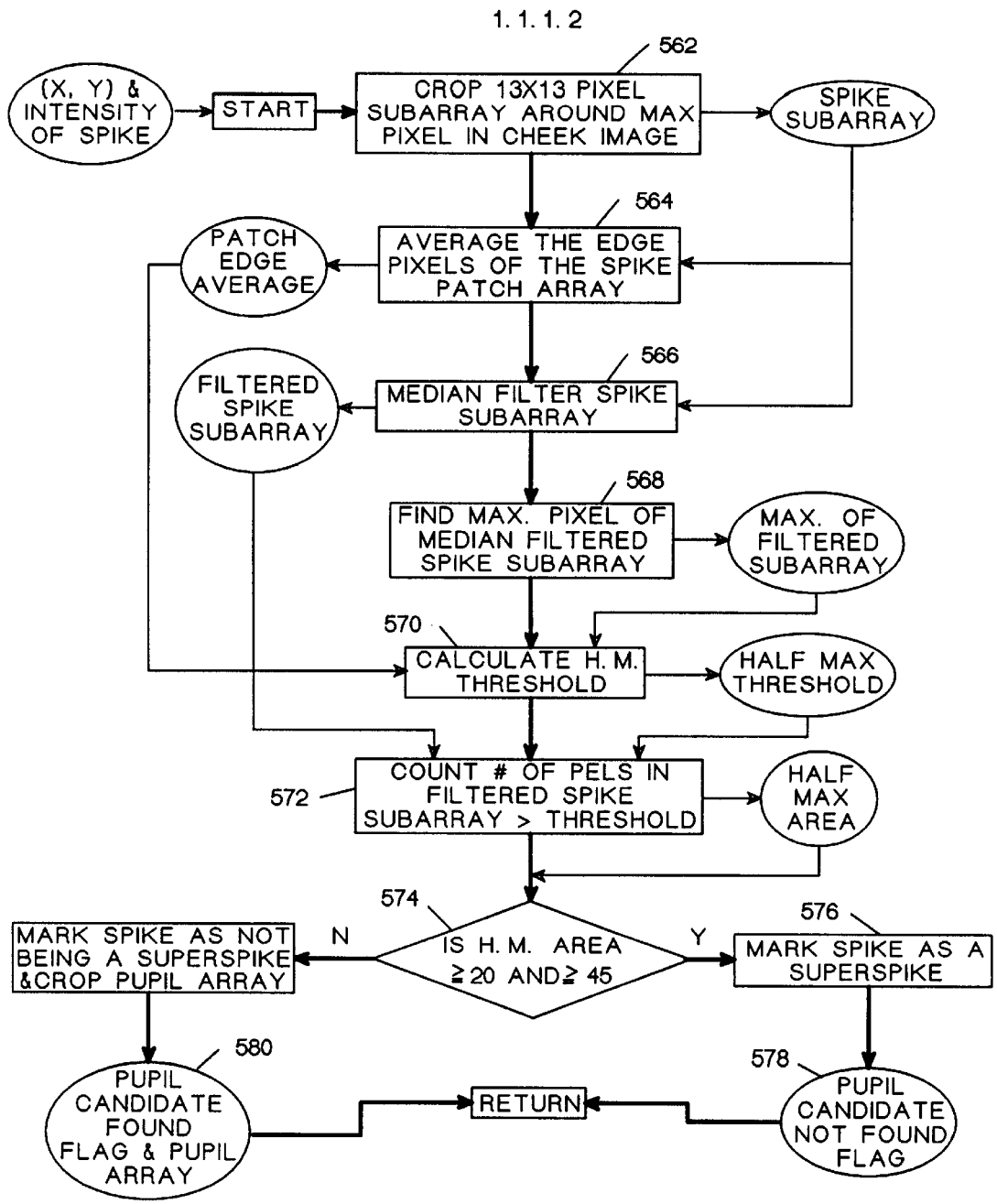
Figure 15F:
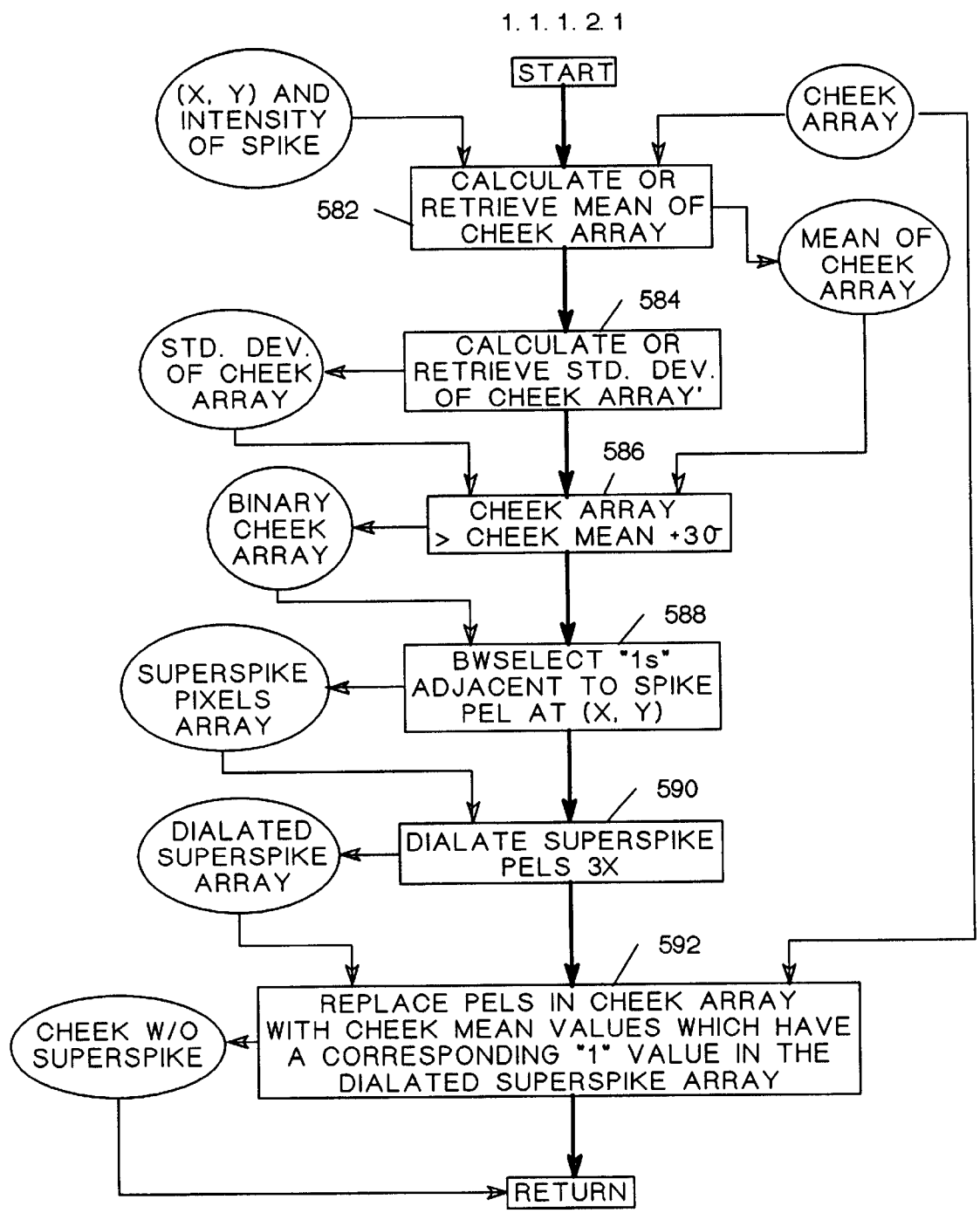

As described, a test is made for superspikes at box 534 (FIG. 15b), these superspikes being reflections from areas generally larger than an area encompassed by a corneal spike. Initially, referring to FIG. 15e, at box 562 a small array, such as a 13 by 13 pixel array, is centered on a pixel registering the highest intensity of the superspike. At box 564 intensity values of the edge of the 13 by 13 array are averaged, this average defining a bottom of the superspike from which the half maximum of the superspike is calculated at box 570. At box 566 a median filter is applied to the 13 by 13 array. This median filter may be as described above for box 542 of FIG. 15b, and thus has the effect of clipping any individual pixels in the spike having intensity values that are inordinately high. The highest intensity value is then located in this clipped spike at box 568, and at box 570 a half maximum value is calculated between the peak value and base value of box 564, this value used as a threshold. This half maximum value is basically the intensity value that is of a value ½ the highest intensity registered in the clipped spike. The number of pixels above the half maximum threshold are then counted at box 572, and at box 574 the inquiry is made as to whether the number of pixels above the half maximum threshold is greater than or equal to 20 but less than or equal to 45, these values being determined empirically from a database of superspikes. Here, after the processing of boxes 562–572, it has been found that a normal corneal spike will generally contain about 15 pixels. Where there are more than 20 pixels registering intensity values greater than the half maximum threshold, then the spike is marked as a superspike. Areas registering greater than the half maximum of 45 pixels most often indicate a broad, nonpupil high intensity area such as a cheekbone area of the half face image, although such an area may also indicate an abnormally high pupillary reflection with an intensity higher than the corneal spike. If the answer at box 574 is YES, then at box 576 the spike is marked as a superspike and at box 578 the program sets a flag indicating a candidate pupil was not located. If the answer is NO, then at box 580 the spike is assumed to be the corneal spike and a 96 by 96 candidate pupil array is cropped centered about the spike.

Where it is determined that the spike is a superspike, and for suppressing the superspike, reference is made to box 535 of FIG. 15b and FIG. 15f. Here, the mean and standard deviation of the half face image are either calculated or retrieved at boxes 582 and 584, respectively. At box 586 the half face image is scanned for pixels registering light intensities greater than the mean value plus 3 standard deviations, this value used as a threshold. While 3 standard deviations is disclosed herein by way of example, a range of from, say about 2 to 4 standard deviations may also work to threshold areas of superspike pixels. Additionally, parameters other than the mean, such as the median, may also be used in conjunction with other values of standard deviation to threshold superspike areas. In any case, pixels above the selected threshold are set to a ONE value, and pixels below the threshold are set to a ZERO value, developing a binary mask. At box 588 a BWSELECT (black and white select), a MATLAB Image Processing Toolbox function, is performed. This has the effect of isolating the superspike and any adjacent pixels over the threshold value. A DILATE operation as described above is then performed 3 times at box 590, expanding the selected superspike area by 3 pixels around its border. At box 592 all pixels of a ONE value, i.e. the superspike pixels, are then replaced with intensity values representative of the mean value in the half face image. This image, or mask, of just the dilated area containing the superspike with all intensity values therein being the mean value of the half face image replaces the superspike area in the half face image, eliminating the superspike area from further consideration in locating the pupil. After elimination of this particular superspike, the program returns to box 522 of FIG. 15*b* where the spike counter is again incremented and the program proceeds to box 524.

Figure 15G:
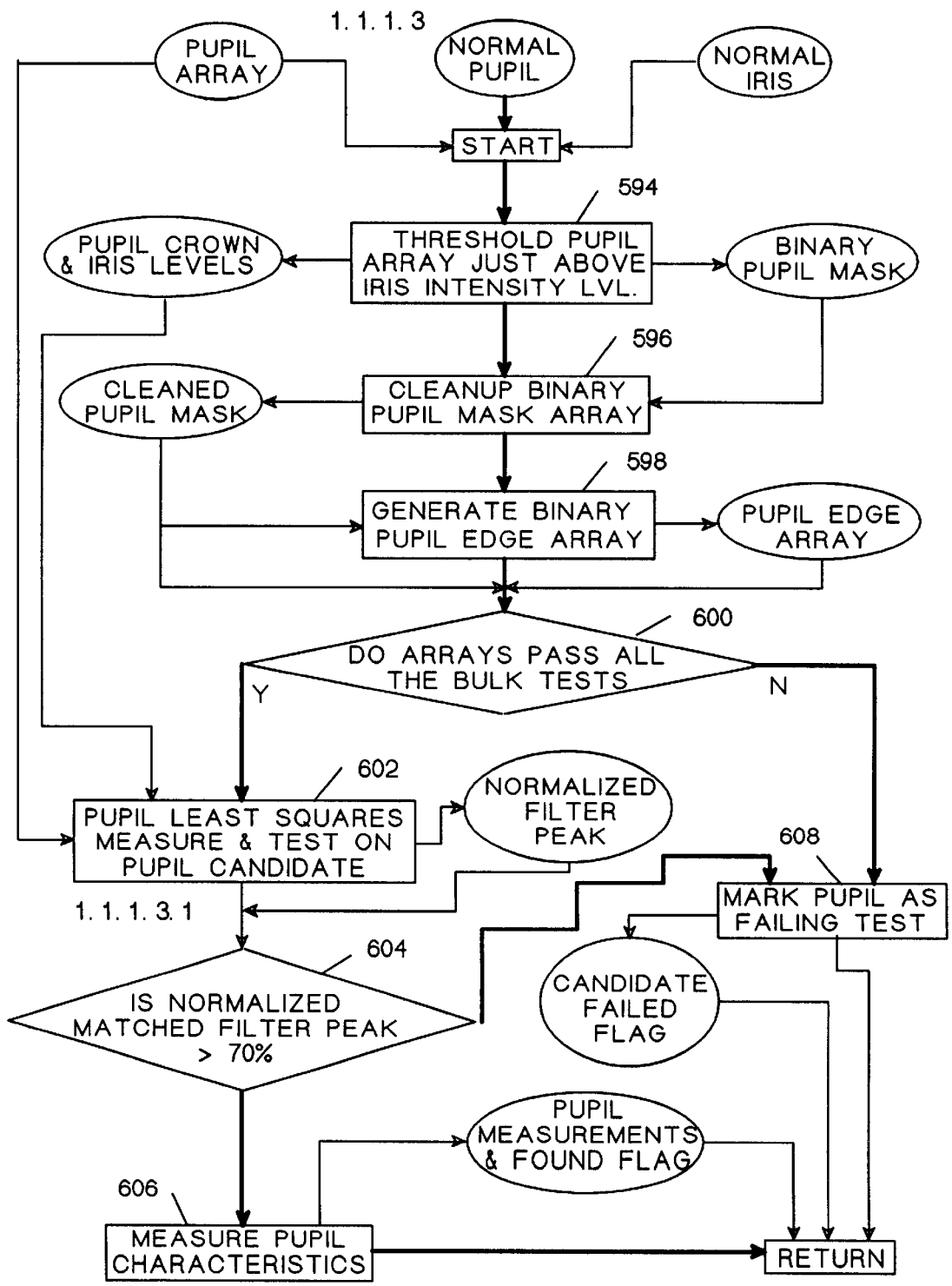

Once the corneal spike is located, an array for containing the pupil, such as a 96 by 96 pixel array, is cropped (not shown) at box 536 of FIG. 15*b*, with the corneal spike centered in the array. This array is fed as inputs to the pupil processing (box 536 of FIG. 15*b*) as the cropped candidate pupil array containing the suspected corneal spike, as will be disclosed in FIG. 15*g*. At box 536 of FIG. 15*b* and subsequently box 512 of FIG. 15*a*, the pupil array is processed as shown in FIG. 15*g*. Initially, average radius, minimum radius and maximum radius of a normal iris and normal pupil are retrieved from memory, these characteristics being obtained from a statistically significant number of normal eyes. At box 594 a threshold value is determined that is just above the iris intensity level for the candidate pupil and pixels having intensity values above this level assigned a binary ONE value. As the pupillary disk is of higher intensity than the iris, this yields a binary pupil mask wherein the pupil is shown by ONES, as described above. This mask is "cleaned" at box 596 using morphological operations similar to those used in FIG. 5*b* as described above, eliminating spurious pixels, spurs, etc. to obtain a cleaned binary pupil mask. At box 598 a pupil edge array is developed as described above from the cleaned binary pupil mask. At box 600 a series of bulk tests similar to those described for FIG. 5 as described above are performed on the pupil edge array. These bulk tests are probably not necessary in the instant invention, but may occasionally reject a candidate pupil array that passed the other previous tests, and thus are retained. Where the candidate array passes the bulk tests of box 600, then at box 602 a pupil least squares measurement and matched filter test of the candidate array is performed, as will be further described. From the least squares test, a normalized matched filter is obtained which is compared at box 604 to the normal pupil and iris. If the comparison is greater than about 70%, a percentile that has been found to work well in this application, then the pupil candidate passes the least squares test of box 602. In this instance, the program passes to box 606 where characteristics of the pupil are measured and stored. These characteristics are indicated at box 494 and 496 of FIG. 15, and further include the pupil crown intensity level, pupil intensity moments and standard deviation of the pupil intensity levels. As described earlier, these statistics and measurements may be used to develop graphical presentations for an operator and may also be used in diagnosing disease processes and opacities in the eyes.

Where the normalized matched filter at box 604 is less than about 70%, or if the candidate array fails the bulk tests, then the program passes to box 608, where the candidate array is marked as failing either the bulk tests or the pupil least squares measurement and matched filter test. The program then returns to box 508 of FIG. 15*b*, or 518 if called from 512.

Figure 15H:
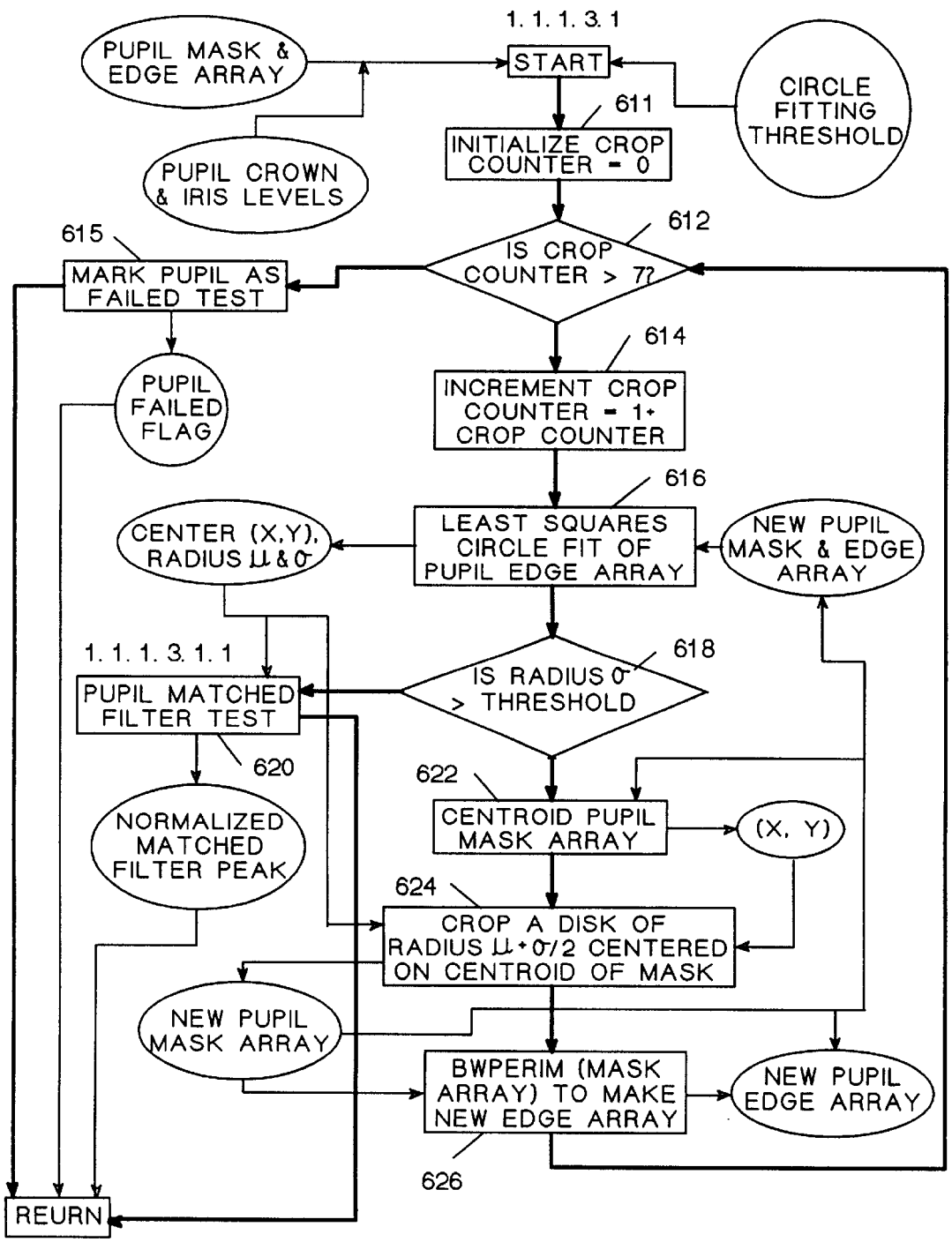
FIG. 15*h* is a flowchart illustrating particulars of the flowchart of FIG. 15*g*.

FIG. 15*h* illustrates the process by which the least squares measurement and matched filter test is done. Data used here are the pupil mask and pupil edge array, the pupil crown level, pupil iris level and a circle fitting threshold. This latter parameter is a standard deviation of the pupil radius, and establishes how accurately circularity of the pupil is to be measured. The program of FIG. 15*h* runs in a loop, so at box 611 a crop counter is initialized to a 0 value, and at box 612 the query is made as to whether the crop counter is greater than 7. If the answer is NO, then the program falls through to box 614 where the crop counter is incremented by one. If the answer is YES, then the program proceeds to box 615 where the pupil test is marked as failed, and the program returns to box 536 of FIG. 15*b* or to box 602 of FIG. 15*g*, depending on where the subroutine call was made from, as described above. In the instance where the crop counter has not reached a count of 7 (box 612), then at box 616 a least squares circle fit of the pupil edge array is performed. This test indicates whether there is a circle representative of a pupil, and also indicates a radius and center of the pupil and a standard deviation of the radius. If the fit of the least squares circle is close to that of the pupil, then the standard deviation of the radius of the pupil will be relatively small. At box 618 the query is made as to whether the radius standard deviation is greater than an empirically derived threshold of about 1.5 pixels, and if the answer is YES, indicating that the least squares circle fit is relatively good, then the program proceeds to box 620, where a matched pupil filter test is done. Data from box 616 provided to the process of box 620 is a center coordinate and a radius of the best matching circle. If the standard deviation is greater than the threshold then the program proceeds to box 622 where a centroid of the pupil mask array is found. At box 624 a disk is cropped from the array of a radius $\mu+\sigma/2$ centered on the previously described centroid resulting in a revised pupil mask array, and at box 626 a revised pupil edge array is created using a BWPERIM algorithm from MATLAB from the array developed at box 624. The new pupil mask array and new pupil edge array from boxes 624 and 626 are then applied to box 616 where the process is repeated. This process of boxes 618–626 eliminates artifacts exterior to the actual pupil as contained in the original pupil mask and edge array applied to box 611. The program then again loops back to box 612, where the least square fit is better than in the previous loop, with a better chance that the program will exit the loop at box 620. Generally, where a well defined pupil is not present, the program will loop through boxes 622–626 2 or 3 times before the radius error is less than the threshold at box 618. If the pupil cannot be found by the 7th loop, then the program exits at box 612 as described above. While 7 loops are disclosed, any number of from about 4–8 loops may also be used. A similar process may be used to measure the iris radius.

Figure 15I:
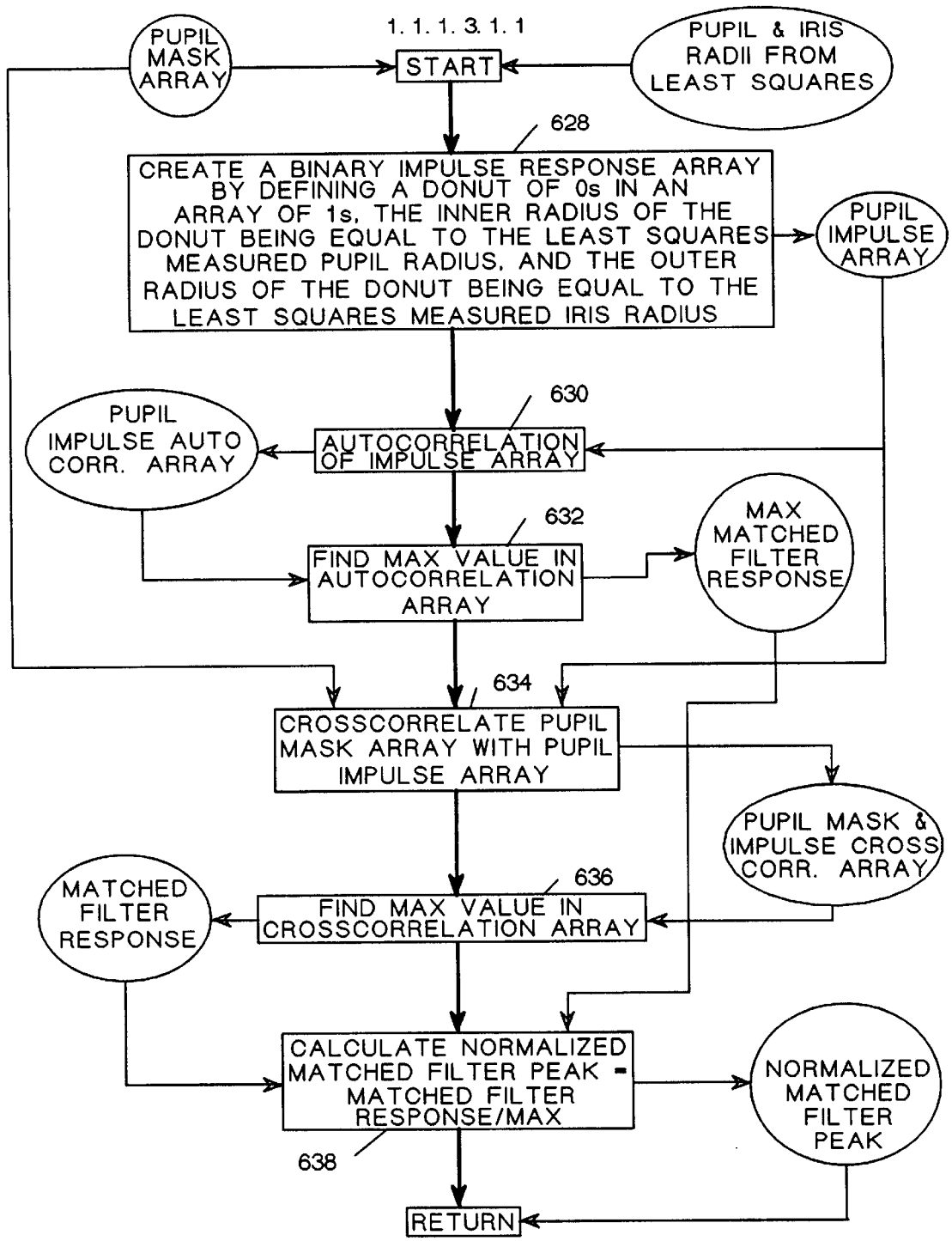
FIG. 15*i* is a flowchart illustrating particulars of the flowchart of FIG. 15*h*.
Figure 15J:
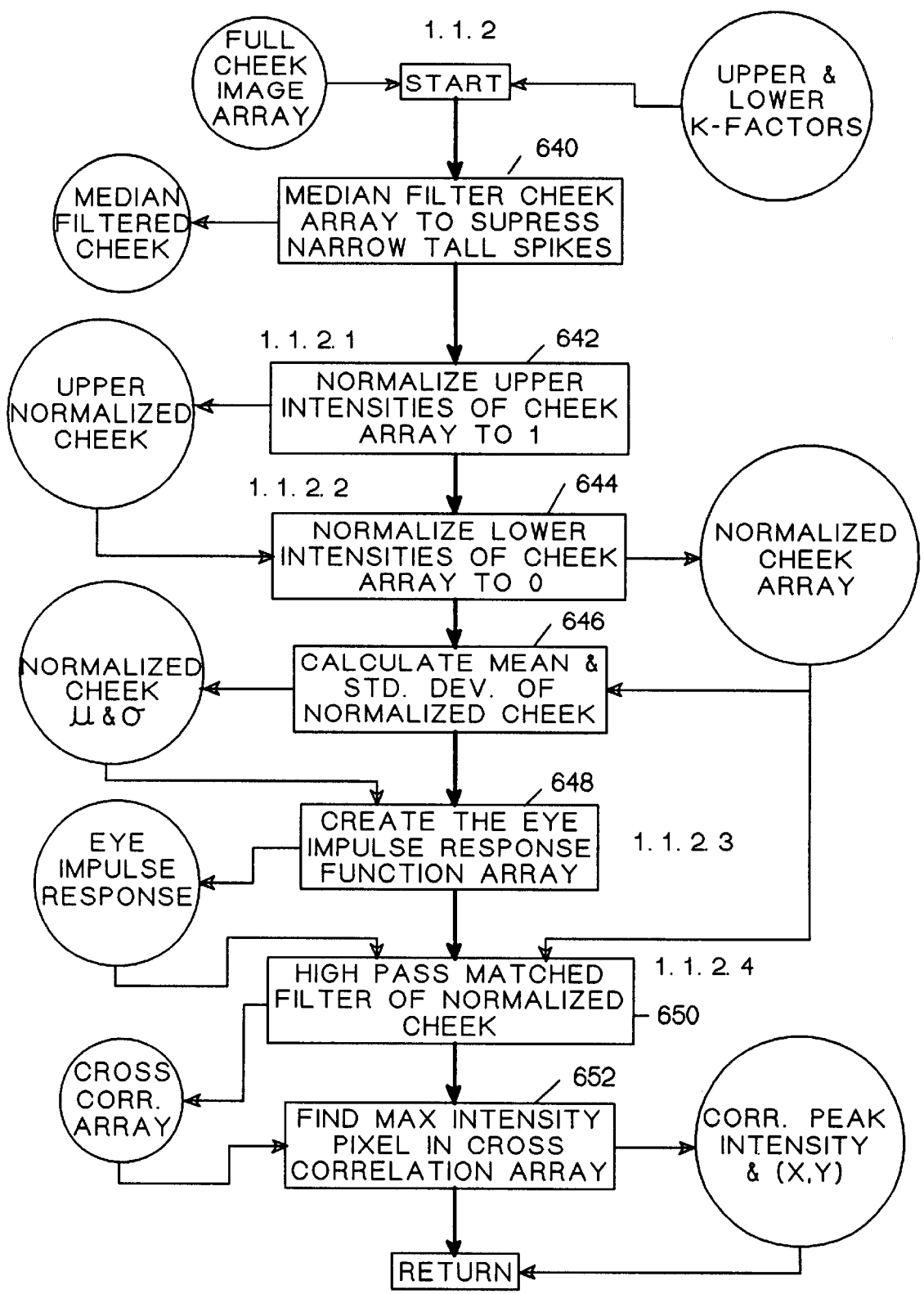
FIG. 15*j* is a flowchart illustrating particulars of the flowchart of FIG. 15*a*.

Once the candidate pupil is found, then a matched filter correlation is performed at box 620. Referring to FIG. 15*i*, a pupil binary impulse response array is developed at box 628 from the pupil mask array and the pupil and iris radii from box 616 of FIG. 15*h*. This results in an annular array of ZEROs in an array of ONEs, with the inner radius of the annulus, or donut-shaped area of ZEROs, equal to the least squares measured pupil radius in pixels and the outer radius of the annulus equal to the least squares measured iris radius in pixels. An autocorrelation of the pupil impulse response array is performed at box 630, resulting in an autocorrelation array, and at box 632 a maximum value of the autocorrelation peak in the autocorrelation array is found. This maximum value is the maximum possible matched filter response for the given pupil impulse response array. The pupil impulse response array is then crosscorrelated at box 634 with the pupil mask array to develop a pupil mask and impulse cross correlation array. The maximum crosscorrelation peak value is then found in the cross correlation array at box 636, this maximum value being the matched filter response, and at box 638 the matched filter response is divided by the maximum possible matched filter response from box 632 to calculate a ratio between the two. This ratio is the normalized matched filter peak. At this point the program returns to box 620 of FIG. 15*h,* and subsequently to box 504 and then to box 506 of FIG. 15*a* or box 602 of FIG. 15*g* (depending from where the call was made from) where the inquiry is made as to whether the normalized matched filter peak is greater than 70%.

Where the normalized matched filter peak is not greater than 70% at box 604 of FIG. 15*g,* then the program sets a flag at box 608 indicating that the pupil has not been found. The program then returns to box 506 of FIG. 15*a*. Also, the program may return to box 516 of FIG. 15*a* if the subroutine call was made at box 512 of FIG. 15*a*. At box 508 of FIG. 15*a,* the search for the pupil using the corneal spike has not succeeded in finding the pupil, so the program proceeds to the full cheek image matched filter search as illustrated in the flowchart of FIG. 15*j*. Here, at box 640 the half face image and upper and lower K-factors, which are simply multiplication factors for the standard deviation, are input to the process of FIG. 15*j*. The K factors are generally about 1.5, being empirically derived from a database of eyes. Initially, a median filter is applied to the half face array to clip any tall narrow spikes that may exist in the array that may overly bias the array statistics. Next, at box 642 large areas of higher intensity pixels in the half face array, which are usually found in large areas of the cheek and skin areas around the eyes, are normalized to a ONE value. At box 644 the lower value pixels, such as areas in shadows around the eye and eyelid, are normalized to a ZERO value, as will be further explained. This provides a normalized cheek array wherein pixel values are compressed into a dynamic range of pixel values to between ONE and ZERO. At box 646 the mean and standard deviation of the normalized half face image from boxes 642 and 644 is calculated, and an eye impulse response function array is created at box 648. This eye impulse response function array is similar to that described above for the pupil, except it is customized to the compressed dynamic range of the half face image. A high spectral frequency pass band filtered matched filter is applied to the normalized half face image to develop a matched filter response of the normalized half face image. At box 652 the maximum intensity of the cross correlation array is found, and the location of this correlation peak in the half face image should be the location of the eye. The program then exits to box 510 of FIG. 15*a* where a 96 by 96 pixel pupil array is cropped around the correlation spike located at box 652 of FIG. 15*j,* and the pupil is processed as described for FIG. 15*g*.

The half face matched filter search of FIG. 15*j* is more effective at locating the pupil than analysis of the corneal spike or the other disclosed methods for locating the pupil, but as stated is more computationally intensive than the other methods for locating the eye. Thus, the method of FIG. 15*j* is reserved for use only when the other methods are unable to locate the pupil. As microcomputers advance to a point where use of a computationally intensive subroutine such as that of FIG. 15*j* is feasible, then such a subroutine may be initially used to locate the eye without resorting to less intensive but less robust routines.

Figure 15K:
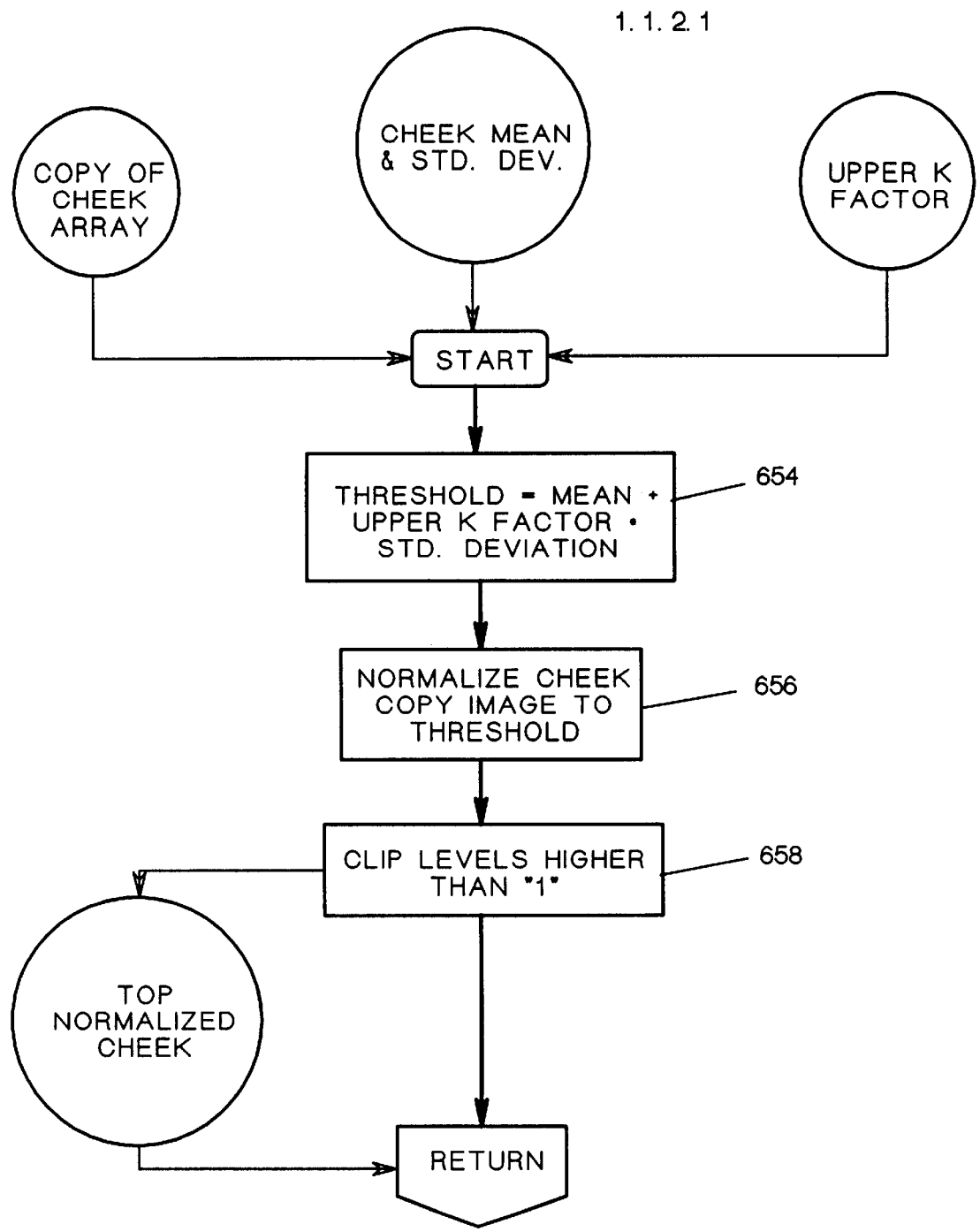
Figure 151:
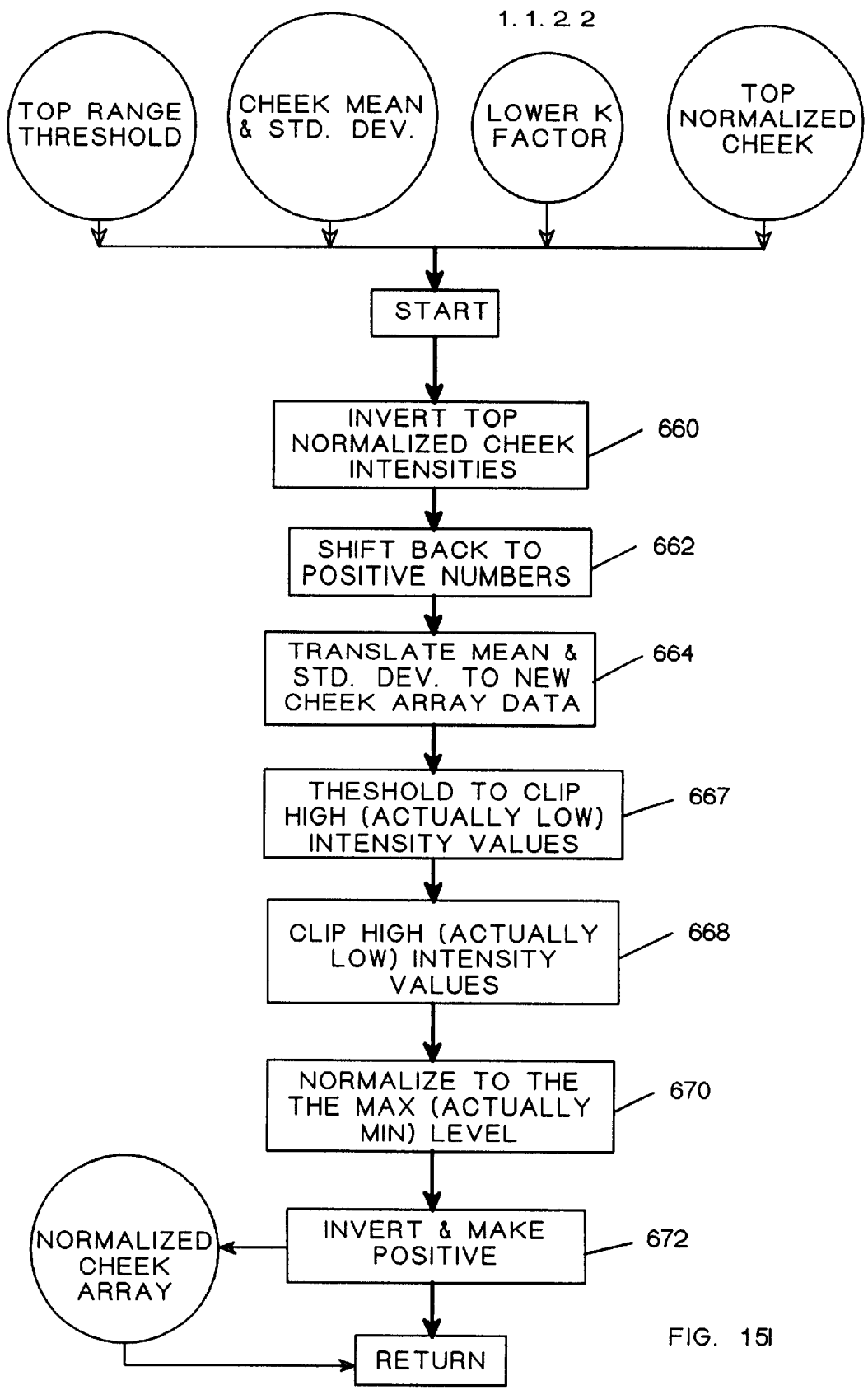

FIG. 15*k* shows the process of box 642 of FIG. 15*j,* i.e. setting (or normalizing) the higher intensity pixels in the median filtered array to ONE. In this subroutine, a copy of the cheek array, the cheek mean and standard deviation and the upper K factor from FIG. 15J are used. Here, the standard deviation changes for each different subject image depending on differences of intensity levels between different images. A threshold is established at box 654, this threshold being the mean of intensity values in the half face array plus the standard deviation of the pixel intensities of the half face array multiplied by the upper K factor. As such, at box 656 pixel intensities in the half face array above the threshold are set to ONE and pixel intensities below the threshold are scaled between 0 and 1. This develops a normalized half face image, and at box 658 pixel intensities greater than 1 are set to 1. At this point the program returns to box 644 of FIG. 15*j* and the program continues as described.

FIG. 15*l* shows a subroutine for normalizing the lower pixel intensities at box 644 of FIG. 15*j*. Parameters used for this process are the normalized half face array from box 658 of FIG. 15*k,* a lower K factor which is empirically derived (about 1.5), the original half face array mean and standard deviation, and the top range threshold from box 654 of FIG. 15*k*. Initially, at box 660, pixel intensity values of the normalized half face array from box 658 are inverted so that the highest intensity value becomes –1, with lowest intensity values corresponding to 0. Negative numbers are shifted to positive numbers at box 662 by adding 1 to all intensity values, and at box 664 the mean and standard deviation of intensity values in the original, non-normalized half face array are translated to the 0–1 scale by dividing the mean of FIG. 15*k* by the threshold of 15*k* and subtracting this from 1. This gives a normalized mean translated into the 0–1 scale. The standard deviation for the 0–1 scale is obtained in the same manner, providing a normalized standard deviation. At box 667 a new threshold is established as described for FIG. 15*k* by adding the normalized mean to the normalized standard deviation multiplied by the lower K factor, and this threshold applied to the inverted half face array so that intensity values higher than 1 are clipped at box 668 and intensity values between 0 and 1 are scaled an d compressed in a similar manner at box 670 as described for FIG. 15*k*. At box 672 the array is again inverted and the numbers made positive so that the low intensity values are normalized in a like manner as the high intensity values were normalized in FIG. 15*k*. The processes of FIGS. 15*k* and 15*l* thus clips intensity levels above and below a k factor multiplied by the standard deviation of the mean and normalized the intensity values to be between 1 and 0.

Figure 15M:
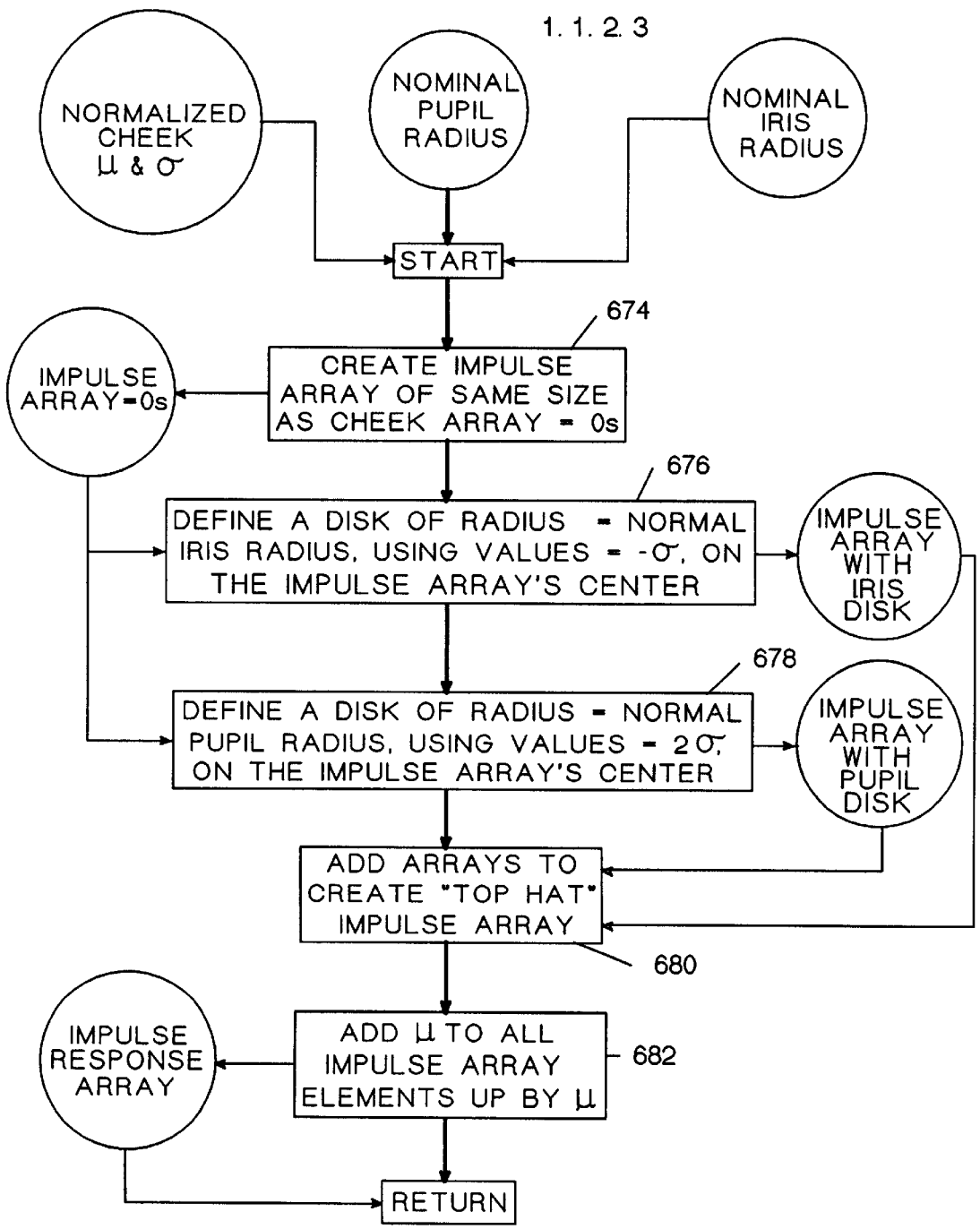

FIG. 15*m* illustrates a subroutine for developing the eye impulse response function array of box 648 of FIG. 15*j*. Parameters for this subroutine are the normalized standard deviation and normalized mean, the normal pupil radius and normal iris radius. At box 674 an impulse array is developed and initially populated by ZEROES, this array being the same size as the full face array. A disk is centered in the array of ZEROs at box 676, the disk having a radius equal to the normal iris radius and wherein intensity values of the disk are set to the negative of the normalized standard deviation from box 664 of FIG. 15*l*. At box 678 a second array populated by ZEROs is developed centered about a disk defined by the radius of a normal pupil. Intensity values of this pupil disk are set to intensity values of double the normalized standard deviation. At box 680 the two arrays are added together, and at box 682 the mean is added so as to form an impulse response array having intensity values wherein a cross section through the pupil has a characteristic shape of a "top hat" , as shown in FIG. 3*e* but scaled so the top is $\mu+\sigma$ and the bottom is $\mu-\sigma$. This "top hat" configuration represents a normal eye normalized to the new scale, and is the desired response in the normal eye cheek array.

In the flowchart of FIG. 15*n,* which illustrates a high pass matched filter of the normalized half face image, a fast Fourier transform is performed on the pupil impulse response array of the normalized half face image of FIG. 15*l* and the normalized cheek array from FIG. 15m at boxes 684 and 686, respectively. At box 688 an element by element product of the arrays is performed, which in turn provides a fast Fourier cross correlation array. This cross correlation array is applied to the high pass filter of box 690, which in turn provides a fast Fourier filtered cross correlation array. An inverse fast Fourier transform is performed at box 692 to obtain a filtered cross correlation array, after which the program returns to box 652 of FIG. 15j. Here, the maximum intensity pixel in the filtered cross correlation array is located, this maximum intensity location indicating location of the eye. This location is provided to box 510 of FIG. 15a, where a new array is cropped about the pupil and this new array processed for a pupil.

We claim:

1. A method for processing an image including eyes of a subject registered by a reflex photometer comprising the steps of:

1) obtaining at least a partial image of a face of a subject containing eyes of said subject, 2) dividing said image into a first half and a second half so that said first half and said second half each contain an image of one of said eyes, 3) processing said first half and said second half to at least determine a position of a pupil of a one of said eves in said first half and said second half.

2. A method as set forth in claim 1 further comprising the step of excluding an area around an eye in each of said first half and said second half prior to initiating a search for said pupils of said eyes.

3. A method as set forth in claim 2 further comprising the step of sequentially applying a series of tests to each pixel in a searched area of each said first half and said second half to determine if the pixel under test has characteristics of a pupil of an eye.

4. A method as set forth in claim 3 wherein one of said tests further comprises the step of testing a said pixel under test to determine if it exceeds an intensity threshold of a lowest expected intensity value of a pixel registering a pupil.

5. A method as set forth in claim 3 wherein one of said tests further comprises the step of testing a said pixel under test to determine if it is a hot pixel.

6. A method as set forth in claim 3 wherein one of said tests further comprises the step of testing an area immediately around a said pixel under test to determine if said area is of an intensity value generally greater than an overall pixel intensity value in a respective said half said pixel under test is in.

7. A method as set forth in claim 3 wherein one of said tests further comprises the step of determining if circular structures exist in a region around the pixel under test.

8. A method as set forth in claim 7 further comprising the steps of:

establishing a reference intensity level that is generally lower than intensity levels of a pupil of an eye, beginning at a pixel having an intensity value characteristic of a corneal spike, successively comparing pixel intensities in radially opposed directions from said pixel having an intensity value characteristic of a corneal spike with said reference intensity level until pixels having a lower intensity value than said reference value are detected, in a plurality of lines generally perpendicular to said radially opposed directions, sequentially testing pixels until first transition intensities lower than said reference intensity level are located, storing pixel locations registering said first transition intensities.

9. A method as set forth in claim 8 further comprising the step of sequentially testing pixels in directions normal to each said plurality of lines until second transition intensities lower than said reference intensity level are located, storing pixel locations registering said second transition intensities.

10. A method as set forth in claim 9 further comprising the step of averaging said pixel locations of said first transition intensities and said second transition intensities to obtain an approximate location of a center of said pupil.

11. A method as set forth in claim 10 further comprising the steps of:

developing a 2 dimensional eye array for each eye of a subject, each said eye array including a pupil and at least a portion of an iris of a respective said eye, with each said pupil generally centered within an associated said eye array, for each said 2 dimensional eye array, developing a first histogram array of intensity values developed from rows of pixels across at least said pupil in each said 2 dimensional eye array, for each said eye array, developing a second histogram array of intensity values developed from columns of pixels across at least said pupil in each said 2 dimensional eye array, locating said first histogram array horizontally aligned with respect to an associated said eye array, locating said second histogram array vertically aligned with respect to an associated said eye array, dividing pixel intensities into a range of equally separated ranges and assigning a particular color to each said range.

12. A method as set forth in claim 11 further comprising the steps of:

locating a geometric center of said pupil at a center of each said eye array, providing at least one indica on two adjacent sides of each said eye array, said indica showing a geometric center of said pupil and said eye array, comparing a position of a corneal spike in said first histogram array and said second histogram array to respective said indica to determine vertical and horizontal deviation of an eye imaged in each said eye array.

13. A method as set forth in claim 11 further comprising the step of developing said first histogram array and said second histogram array in the form of envelopes each showing an outline of said histogram arrays.

14. A method as set forth in claim 13 further comprising the step of indicating data including average intensity value, standard deviation, and a median value within each said envelope.

15. A method as set forth in claim 7 further comprising the step of determining pixel intensity values along radial lines extending from the pixel under test.

16. A method as set forth in claim 15 further comprising the step of detecting a drop of said pixel intensity values along said radial lines to locate an edge of said pupil.

17. A method as set forth in claim 16 further comprising the step of testing said pixel intensity values along said radial lines to locate pupil to iris transitions along each said radial line.

18. A method for displaying eyes of a subject imaged by a reflex photometer and comprising the steps of:

vertically dividing an image of said eyes into a first half and a second half, developing a two-dimensional plot of said first half and said second half, dividing light intensity values of pixels in said first half and said second half into a plurality of predetermined ranges, assigning a different color for each of said predetermined ranges to develop a two-dimensional plot for each said first half and said second half.

19. A method as set forth in claim 18 further comprising the step of developing a histogram of intensity values of said first half and said second half.

20. A method as set forth in claim 18 further comprising the step of designating the range of intensity values including a highest number of pixels as a most probable intensity value.

21. A method as set forth in claim 18 further comprising the step of narrowing a span of said predetermined ranges of intensity values just above said most probable intensity values so that said predetermined ranges of intensity values just above said most probable intensity value is of a greater resolution.

22. A method as set forth in claim 18 further comprising the step of including a light intensity range between the most probable intensity value and approximately 10% of the highest intensity value.

23. A method as set forth in claim 18 wherein a three-dimensional plot of said first half and said second half is developed by vertically and horizontally offsetting light intensity values for each row of pixels.

24. A method as set forth in claim 23 further comprising the step of storing said two dimensional plot and said three dimensional plot for further analysis.

25. A method as set forth in claim 18 wherein a portion of said first half and said second half containing said eyes of the subject are transmitted to a different location for processing.

26. A method as set forth in claim 25 further including the steps of:

transmitting coordinates of the eyes in the full-face image, transmitting interpupillary distance between said pupils of said eyes.

27. A method as set forth in claim 18 further comprising the steps of:

locating a predetermined number of groups of pixels registering higher levels of light intensity, performing a series of tests to determine if the region around each group of pixels has characteristics of at least a pupil.

28. A method as set forth in claim 18 further comprising the steps of:

1) scanning each said array for pixels registering light intensity peaks, 2) applying a series of tests to determine whether any of said light 3) After a pupil is located, storing light intensity values of a small array just around the pupil.

29. A method as set forth in claim 28 further comprising the step of developing 2 dimensional and three dimensional images of said small array of pixels.

30. A method as set forth in claim 27 wherein one of said series of tests comprises the step of, for each of said predetermined number of groups of pixels registering higher levels of light intensity, testing pixel intensity values along a predetermined number of radial lines beginning from said group of pixels until light intensities representative of an edge of said pupil is found.

* * * * *